(12) United States Patent
Crowder et al.

(10) Patent No.: US 11,064,926 B2
(45) Date of Patent: Jul. 20, 2021

(54) SYSTEMS AND METHODS FOR ASSESSING THE EFFECTIVENESS OF A THERAPY INCLUDING A DRUG REGIMEN USING AN IMPLANTABLE MEDICAL DEVICE

(71) Applicant: NeuroPace, Inc., Mountain View, CA (US)

(72) Inventors: Tara L. Crowder, Woodside, CA (US); Brett M. Wingeier, San Francisco, CA (US); Martha J. Morrell, Portola Valley, CA (US); Felice Sun, Palo Alto, CA (US); Thomas Tcheng, Pleasant Hill, CA (US)

(73) Assignee: NeuroPace, Inc., Mountain View, CA (US)

( * ) Notice: Subject to any disclaimer, the term of this patent is extended or adjusted under 35 U.S.C. 154(b) by 755 days.

(21) Appl. No.: 15/817,160

(22) Filed: Nov. 17, 2017

(65) Prior Publication Data

US 2018/0085015 A1 Mar. 29, 2018

Related U.S. Application Data

(62) Division of application No. 13/539,301, filed on Jun. 30, 2012, now abandoned.

(Continued)

(51) Int. Cl.
*A61B 5/00* (2006.01)
*A61B 5/24* (2021.01)
(Continued)

(52) U.S. Cl.
CPC .............. *A61B 5/24* (2021.01); *A61B 5/0002* (2013.01); *A61B 5/377* (2021.01); *A61B 5/4848* (2013.01);
(Continued)

(58) Field of Classification Search
None
See application file for complete search history.

(56) References Cited

U.S. PATENT DOCUMENTS

| 7,209,787 B2 | 4/2007 | Dilorenzo |
| 7,231,254 B2 | 6/2007 | Dilorenzo |

(Continued)

FOREIGN PATENT DOCUMENTS

WO 2010083228 A2 7/2010

OTHER PUBLICATIONS

Li Y, Mogul DJ. "Electrical control of epileptic seizures". J Clin Neurophysiol 2007; 24: 197-204.

(Continued)

*Primary Examiner* — Etsub D Berhanu
(74) *Attorney, Agent, or Firm* — Loza & Loza, LLP; David S. Sarisky

(57) ABSTRACT

Systems and methods rely on feedback from an active medical device or devices (e.g., neurostimulator coupled to sensing and stimulation elements such as electrodes) to assess the effectiveness of a patient's drug regimen. Such reliance may include analyzing characteristics in physiological data acquired by the medical device(s), for example, in the form of responses evoked from the patient by electrical stimulation waveforms. Systems and methods further involved adjusting one or more parameters according to which a combination therapy consisting of at least a drug regimen and an electrical stimulation therapy are delivered to a patient, in an effort to optimize the therapeutic effect of the combination. The adjustments may be automatically by one or more implanted or external hosts working together or alone, and/or with the input of a physician.

29 Claims, 20 Drawing Sheets

Related U.S. Application Data

(60) Provisional application No. 61/504,164, filed on Jul. 1, 2011.

(51) Int. Cl.
*A61B 5/377* (2021.01)
*A61B 5/145* (2006.01)
*A61B 5/1455* (2006.01)

(52) U.S. Cl.
CPC ......... *A61B 5/0022* (2013.01); *A61B 5/14539* (2013.01); *A61B 5/14553* (2013.01); *A61B 5/4082* (2013.01); *A61B 5/4094* (2013.01)

(56) References Cited

U.S. PATENT DOCUMENTS

| | | |
|---|---|---|
| 7,242,984 B2 | 7/2007 | Dilorenzo |
| 7,266,412 B2 | 9/2007 | Stypulkowski |
| 7,277,758 B2 | 10/2007 | Dilorenzo |
| 7,280,867 B2 | 10/2007 | Frei |
| 7,324,851 B1 | 1/2008 | Dilorenzo |
| 7,403,820 B2 | 7/2008 | Dilorenzo |
| 7,529,582 B1 | 5/2009 | Dilorenzo |
| 7,542,803 B2 | 6/2009 | Heruth |
| 7,599,736 B2 | 10/2009 | Dilorenzo |
| 7,623,928 B2 | 11/2009 | Dilorenzo |
| 7,676,273 B2 | 3/2010 | Goetz |
| 7,747,325 B2 | 6/2010 | Dilorenzo |
| 7,787,945 B2 | 8/2010 | Greene |
| 7,801,618 B2 | 9/2010 | Pless |
| 7,813,811 B2 | 10/2010 | Wingeier et al. |
| 7,822,481 B2 | 10/2010 | Gerber |
| 7,853,322 B2 | 12/2010 | Bourget |
| 7,853,329 B2 | 12/2010 | Dilorenzo |
| 7,894,903 B2 | 2/2011 | John |
| 7,899,545 B2 | 3/2011 | John |
| 7,930,035 B2 | 4/2011 | Dilorenzo |
| 7,957,797 B2 | 6/2011 | Bourget |
| 7,957,809 B2 | 6/2011 | Bourget |
| 7,974,696 B1 | 7/2011 | Dilorenzo |
| 8,027,730 B2 | 9/2011 | John |
| 8,126,567 B2 | 2/2012 | Gerber |
| 8,140,150 B2 | 3/2012 | Greene |
| 8,140,151 B2 | 3/2012 | Greene |
| 8,160,720 B2 | 4/2012 | Wingeier et al. |
| 8,190,270 B2 | 5/2012 | Wingeier et al. |
| 8,224,434 B2 | 7/2012 | Greene |
| 8,543,214 B2 | 9/2013 | Osorio |
| 8,543,217 B2 | 9/2013 | Stone |
| 8,694,115 B2 | 4/2014 | Goetz |
| 8,731,656 B2 | 5/2014 | Bourget |
| 8,903,486 B2 | 12/2014 | Bourget |
| 2003/0018367 A1 | 1/2003 | Dilorenzo |
| 2003/0135128 A1 | 7/2003 | Suffin et al. |
| 2003/0171789 A1 | 9/2003 | Malek |
| 2004/0059599 A1 | 3/2004 | McIvor |
| 2004/0199217 A1 | 10/2004 | Lee |
| 2004/0199218 A1 | 10/2004 | Lee |
| 2004/0215286 A1 | 10/2004 | Stypulkowski |
| 2004/0267330 A1 | 12/2004 | Lee |
| 2005/0021103 A1 | 1/2005 | Dilorenzo |
| 2005/0021104 A1 | 1/2005 | Dilorenzo |
| 2005/0060007 A1 | 3/2005 | Goetz |
| 2005/0060008 A1 | 3/2005 | Goetz |
| 2006/0094970 A1 | 5/2006 | Drew |
| 2007/0026440 A1* | 2/2007 | Broderick ............ A61B 5/1468 435/6.11 |
| 2007/0032734 A1 | 2/2007 | Najafi |
| 2007/0073169 A1 | 3/2007 | Averina |
| 2007/0073355 A1 | 3/2007 | Dilorenzo |
| 2007/0142862 A1 | 6/2007 | Dilorenzo |
| 2007/0142874 A1 | 6/2007 | John |
| 2007/0162086 A1 | 7/2007 | Dilorenzo |
| 2007/0167991 A1 | 7/2007 | Dilorenzo |
| 2007/0208212 A1 | 9/2007 | Dilorenzo |
| 2007/0213620 A1 | 9/2007 | Reisfeld |
| 2007/0249954 A1* | 10/2007 | Virag ................... A61B 5/7275 600/544 |
| 2007/0287931 A1 | 12/2007 | Dilorenzo |
| 2008/0058773 A1 | 3/2008 | John |
| 2008/0061961 A1 | 3/2008 | John |
| 2008/0071314 A1 | 3/2008 | John |
| 2008/0109005 A1 | 5/2008 | Trudeau |
| 2008/0119900 A1 | 5/2008 | Dilorenzo |
| 2008/0167571 A1 | 7/2008 | Gevins |
| 2008/0208013 A1* | 8/2008 | Zhang ................ A61B 5/1455 600/301 |
| 2008/0319511 A1 | 12/2008 | Pless |
| 2009/0018609 A1 | 1/2009 | Dilorenzo |
| 2009/0082641 A1* | 3/2009 | Giftakis ............. G06F 19/3456 600/300 |
| 2009/0082829 A1 | 3/2009 | Panken et al. |
| 2009/0099468 A1 | 4/2009 | Thiagalingam et al. |
| 2010/0023089 A1 | 1/2010 | Dilorenzo |
| 2010/0121215 A1* | 5/2010 | Giftakis ............. A61N 1/36082 600/544 |
| 2010/0217348 A1 | 8/2010 | Dilorenzo |
| 2010/0241183 A1 | 9/2010 | Dilorenzo |
| 2010/0249859 A1 | 9/2010 | Dilorenzo |
| 2010/0286549 A1 | 11/2010 | John |
| 2011/0098767 A1 | 4/2011 | Sugimachi |
| 2011/0307030 A1 | 12/2011 | John |

OTHER PUBLICATIONS

Lyseng-Williamson KA. "Levetiracetam: a review of its use in epilepsy". Drugs 2011; 71: 489-514.

Masuda Y, Utsui Y, Shiraishi Y, Karasawa T, Yoshida K, Shimizu M. "Relationships between plasma concentrations of diphenylhydantoin, phenobarbital, carbamazepine, and 3-sulfamoylmethyl-1,2-benzisoxazole (AD-810), a new anticonvulsant agent, and their anticonvulsant or neurotoxic effects in experimental animals". Epilepsia 1979; 20: 623-633.

Mohammad-Zadeh M, Mirnajafi-Zadeh J, Fathollahi Y et al. "Effect of low frequency stimulation of perforant path on kindling rate and synaptic transmission in the dentate gyrus during kindling acquisition in rats". Epilepsy Res. 2007; 75: 154-161.

Morrell M. "Brain stimulation for epilepsy: can scheduled or responsive neurostimulation stop seizures?". Curr. Opin.Neurol. 2006; 19: 164-168.

Morrell MJ. "Antiepileptic medications for the treatment of epilepsy". Semin.Neurol. 2002; 22: 247-258.

Morrell MJ. "Responsive cortical stimulation for the treatment of medically intractable partial epilepsy". Neurology 2011; 77: 1295-1304.

Motamedi M, Nguyen DK, Zaatreh M et al. "Levetiracetam efficacy in refractory partial-onset seizures, especially after failed epilepsy surgery". Epilepsia 2003; 44: 211-214.

Okie S. "Traumatic brain injury in the war zone". N.Engl.J Med 2005; 352: 2043-2047.

Oommen J, Morrell M, Fisher RS. "Experimental Electrical Stimulation Therapy for Epilepsy". Curr.Treat. Options.Neurol. 2005; 7: 261-271.

Penfield W, Jasper H. Electrocorticography. Epilepsy and the Functional Anatomy of the Human Brain. Boston: Little, Brown, 1954: 692-738.

Peters TE, Bhavaraju NC, Frei MG, Osorio I. "Network system for automated seizure detection and contingent delivery of therapy". J.Clin.Neurophysiol. 2001; 18: 545-549.

Pitkanen A, Immonen RJ, Grohn OH, Kharatishvili I. "From traumatic brain injury to posttraumatic epilepsy: what animal models tell us about the process and treatment options". Epilepsia 2009; 50 Suppl 2: 21-29.

Rajdev P, Ward M, Irazoqui P. "Effect of stimulus parameters in the treatment of seizures by electrical stimulation in the kainate animal model". Int J Neural Syst. 2011; 21: 151-162.

Ryvlin P, Kahane P. "Does epilepsy surgery lower the mortality of drug-resistant epilepsy?". Epilepsy Res. 2003; 56: 105-120.

(56) References Cited

OTHER PUBLICATIONS

Salazar AM, Jabbari B, Vance SC, Grafman J, Amin D, Dillon JD. "Epilepsy after penetrating head injury. I. Clinical correlates: a report of the Vietnam Head Injury Study". Neurology 1985; 35: 1406-1414.
Sayer NA, Chiros CE, Sigford B et al. "Characteristics and rehabilitation outcomes among patients with blast and other injuries sustained during the Global War on Terror". Arch Phys.Med Rehabil. 2008; 89: 163-170.
Scharfman HE, Goodman JH, Sollas AL, Croll SD. "Spontaneous limbic seizures after intrahippocampal Infusion of brain-derived neurotrophic factor". Exp.Neurol. 2002; 174: 201-214.
Schierhout G, Roberts I. "Prophylactic antiepileptic agents after head injury: a systematic review". J Neurol.Neurosurg.Psychiatry 1998; 64: 108-112.
Schiller Y, Bankirer Y. "Cellular mechanisms underlying antiepileptic effects of low- and high-frequency electrical stimulation in acute epilepsy in neocortical brain slices in vitro". J Neurophysiol. 2007; 97: 1887-1902.
Schmidt D, Baumgartner C, Loscher W. "The chance of cure following surgery for drug-resistant temporal lobe epilepsy. What do we know and do we need to revise our expectations?". Epilepsy Res. 2004; 60:187-201.
Shank RP, Gardocki JF, Streeter AJ, Maryanoff BE. "An overview of the preclinical aspects of topiramate: pharmacology, pharmacokinetics, and mechanism of action". Epilepsia 2000; 41 Suppl 1: S3-S9.
Spencer SS. "When should temporal-lobe epilepsy be treated surgically?". Lancet Neurol. 2002; 1: 375-382.
Spencer SS, Berg AT, Vickrey BG et al. "Initial outcomes in the Multicenter Study of Epilepsy Surgery". Neurology 2003; 61: 1680-1685.
Sramka M, Chkhenkeli SA. "Clinical experience in intraoperational determination of brain inhibitory structures and application of implanted neurostimulators in epilepsy". Stereotact.Funct.Neurosurg 1990; 54-55: 56-59.
Tellez-Zentano JF, McLachlan RS, Parrent A, Kubu CS, Wiebe S. "Hippocampal electrical stimulation in mesial temporal lobe epilepsy". Neurology, Published online before print Mar. 22, 2006.
Ullal GR, Ninchoji T, Uemura K. "Low frequency stimulation induces an increase in after-discharge thresholds in hippocampal and amygdaloid kindling". Epilepsy Res. 1989; 3: 232-235.
Urino T, Hashizume K, Maehara M et al. "Epileptic focus stimulation and seizure control in the rat model of kainic acid-induced limbic seizures". Neurol.Med Chir (Tokyo) 2010; 50: 355-360.
Velisek L, Veliskova J, Moshe SL. "Electrical stimulation of substantia nigra pars reticulata is anticonvulsant in adult and young male rats". Exp.Neurol. 2002; 173: 145-152.
Vonck K, Boon P, Claeys P, Dedeurwaerdere S, Achten R, Van Roost D. "Long-term deep brain stimulation for refractory temporal lobe epilepsy". Epilepsia 2005; 46 Suppl 5: 98-99.
Warren RJ, Durand DM. "Effects of applied currents on spontaneous epileptiform activity induced by low calcium in the rat hippocampus". Brain Res. 1998; 806: 186-195.
Wyckhuys T, De ST, Claeys P et al. "High frequency deep brain stimulation in the hippocampus modifies seizure characteristics in kindled rats". Epilepsia 2007; 48: 1543-1550.
Yamamoto J, Ikeda A, Satow T et al. "Low-frequency electric cortical stimulation has an inhibitory effect on epileptic focus in mesial temporal lobe epilepsy". Epilepsia 2002; 43: 491-495.
Zhu-Ge ZB, Zhu YY, Wu DC et al. "Unilateral low-frequency stimulation of central piriform cortex inhibits amygdaloid-kindled seizures in Sprague-Dawley rats". Neuroscience 2007; 146: 901-906.
Albensi BC, Ata G, Schmidt E, Waterman JD, Janigro D. "Activation of long-term synaptic plasticity causes suppression of epileptiform activity in rat hippocampal slices". Brain Res. 2004; 998: 56-64.
Babb TL, Kupfer WR, Pretorius JK, Crandall PH, Levesque MF. "Synaptic reorganization by mossy fibers in human epileptic fascia dentata". Neuroscience 1991; 42: 351-363.

Barbarosie M, Avoli M. "CA3-driven hippocampal-entorhinal loop controls rather than sustains in vitro limbic seizures". J Neurosci. 1997; 17: 9308-9314.
Bazil CW, Rose A, Resor S, Yapicular B, Hirsch LJ. "Levetiracetam may be more effective for late-onset partial epilepsy". Arch Neurol. 2002; 59: 1905-1908.
Begley CE, Famulari M, Annegers JF et al. "The cost of epilepsy in the United States: an estimate from population-based clinical and survey data". Epilepsia 2000; 41: 342-351.
Bikson M, Lian J, Hahn PJ, Stacey WC, Sciortino C, Durand DM. "Suppression of epileptiform activity by high frequency sinusoidal fields in rat hippocampal slices". J Physiol 2001; 531: 181-191.
Boon P, Vonck K, De Herdt, V et al. "Deep brain stimulation in patients with refractory temporal lobe epilepsy". Epilepsia 2007; 48: 1551-1560.
Bragin A, Wilson CL, Engel J, JR. "Rate of interictal events and spontaneous seizures in epileptic rats after electrical stimulation of hippocampus and its afferents". Epilepsia 2002; 43 Suppl 5: 81-85.
Brodie MJ, Dichter MA "Antiepileptic drugs". N.Engl.J Med 1996; 334: 168-175.
Carrington CA, Gilby KL, McIntyre DC. "Effect of focal low-frequency stimulation on amygdala-kindled afterdischarge thresholds and seizure profiles in fast- and slow-kindling rat strains". Epilepsia 2007; 48: 1604-1613.
Cavalheiro EA, Leite JP, Bortolotto ZA, Turski WA, Ikonomidou C, Turski L. "Long-term effects of pilocarpine in rats: structural damage of the brain triggers kindling and spontaneous recurrent seizures". Epilepsia 1991; 32: 778-782.Brodie MJ, Dichter MA. "Antiepileptic drugs". N.Engl.J Med 1996; 334: 168-175.
Caveness WF, Walker AE, Ascroft PB. "Incidence of posttraumatic epilepsy in Korean veterans as compared with those from World War I and World War II". J Neurosurg. 1962; 19: 122-129.
Chen JW, Ruff RL, Eavey R, Wasterlain CG. "Posttraumatic epilepsy and treatment". J Rehabil.Res.Dev. 2009; 46: 685-696.
Chkhenkeli SA, Chkhenkeli IS. "Effects of Therapeutic Stimulation of Nucleus Caudatus on Epileptic Electrical Activity of Brain in Patients with Intractable Epilepsy". Stereotact.Funct.Neurosurg. 1997; 69: 221-224.
Curia G, Longo D, Biagini G, Jones RS, Avoli M. "The pilocarpine model of temporal lobe epilepsy". J Neurosci.Methods 2008; 172: 143-157.
D'Ambrosio R, Fender JS, Fairbanks JP et al. "Progression from frontal-parietal to mesial-temporal epilepsy after fluid percussion injury in the rat". Brain 2005; 128: 174-188.
Dedeurwaerdere S, Vonck K, De Herdt, V et al. "Neuromodulation with levetiracetam and vagus nerve stimulationin experimental animal models of epilepsy". Acta Neurol.Belg. 2006; 106: 91-97.
Diaz-Arrastia R, Agostini MA, Frol AB et al. "Neurophysiologic and neuroradiologic features of intractable epilepsy after traumatic brain injury in adults". Arch Neurol. 2000; 57: 1611-1616.
Doheny HC, Whittington MA, Jefferys JG, Patsalos PN. "A comparison of the efficacy of carbamazepine and the novel anti-epileptic drug levetiracetam in the tetanus toxin model of focal complex partial epilepsy". Br.J Pharmacol. 2002; 135: 1425-1434.
Durand DM, Warman EN. "Desynchronization of epileptiform activity by extracellular current pulses in rat hippocampal slices". J.Physiol 1994; 480 ( Pt 3): 527-537.
Engel J, JR., Wiebe S, French J et al. "Practice parameter: temporal lobe and localized neocortical resections for epilepsy". Epilepsia 2003; 44: 741-751.
Fisher R, Salanova V, Witt T et al. "Electrical stimulation of the anterior nucleus of thalamus for treatment of refractory epilepsy". Epilepsia 2010.
Fisher RS, Handforth A. "Reassessment: vagus nerve stimulation for epilepsy: a report of the Therapeutics and Technology Assessment Subcommittee of the American Academy of Neurology". Neurology 1999; 53: 666-669.
Gaito J, Nobrega JN, Gaito ST. "Interference effect of 3 Hz brain stimulation on kindling behavior induced by 60 Hz stimulation". Epilepsia 1980; 21: 73-84.
Gaito J. "The effect of variable duration one hertz interference on kindling". Can.J.Neurol.Sci. 1980; 7: 59-64.

(56) References Cited

OTHER PUBLICATIONS

Ghai RS, Bikson M, Durand DM. "Effects of applied electric fields on low-calcium epileptiform activity in the CA1 region of rat hippocampal slices". J.Neurophysiol. 2000; 84: 274-280.

Ghorbani P, Mohammad-Zadeh M, Mirnajafi-Zadeh J, Fathollahi Y. "Effect of different patterns of low-frequency stimulation on piriform cortex kindled seizures". Neurosci.Lett. 2007; 425: 162-166.

Gleissner U, Helmstaedter C, Schramm J, Elger CE "Memory outcome after selective amygdalohippocampectomy in patients with temporal lobe epilepsy: one-year follow-up". Epilepsia 2004; 45: 960-962.

Glien M, Brandt C, Potschka H, Loscher W. "Effects of the novel antiepileptic drug levetiracetam on spontaneous recurrent seizures in the rat pilocarpine model of temporal lobe Epilepsy". Epilepsia 2002; 43: 350-357.

Gluckman BJ, Neel EJ, Netoff TI, Ditto WL, Spano ML, Schiff SJ. "Electric field suppression of epileptiform activity in hippocampal slices". J.Neurophysiol. 1996; 76: 4202-4205.

Gluckman BJ, Nguyen H, Weinstein SL, Schiff SJ. "Adaptive electric field control of epileptic seizures". J. Neurosci. 2001; 21: 590-600.

Goodman J. Experimental Models of Status Epilepticus. In: Peterson SL, Albertson TE, editors. Neuropharmacology Methods in Epilepsy Research. New York: CRC Press, 1998: 95-125.

Goodman JH. "Brain stimulation as a therapy for epilepsy". Adv. Exp.Med.Biol. 2004; 548: 239-247.

Goodman JH, Berger RE, Tcheng TK. "Preemptive Low Frequency Stimulation Decreases the Incidence of Amygdala Kindled Seizures". Epilepsia 2005; 46: 1-7.

Goodman, J. H., Schon, J. P., Phani, S., and Zucker, J. R. Postictal Low Freqeunecy Sine Wave Stimulation Decreases the Incidence of Kindled Seizures. Epilepsia 2005; 46(s8): 104-105.

Goodman JH. Deep Brain and Peripheral Nerve Stimulation as Potential Therapies for Epilepsy. In: Schwartzkroin PA, editor. Encyclopedia of Basic Epilepsy Research, vol. 3. Oxford: Academic Press, 2009: 1421-6.

Hamani C, Ewerton FI, Bonilha SM, Ballester G, Mello LE, Lozano AM. "Bilateral anterior thalamic nucleus lesions and high-frequency stimulation are protective against pilocarpine-induced seizures and status epilepticus". Neurosurgery 2004; 54: 191-195.

Hamani C, Hodaie M, Chiang J et al. "Deep brain stimulation of the anterior nucleus of the thalamus: effects of electrical stimulation on pilocarpine-induced seizures and status epilepticus". Epilepsy Res. 2008; 78: 117-123.

Houser CR. "Granule cell dispersion in the dentate gyrus of humans with temporal lobe epilepsy". Brain Res. 1990; 535: 195-204.

Jennett B. "Posttraumatic epilepsy". Adv.Neurol. 1979; 22: 137-147.

Jerger K, Schiff SJ. "Periodic pacing an in vitro epileptic focus". J.Neurophysiol. 1995; 73: 876-879.

Kano, T., D'Antuono, M., De Guzman, P., Benini, R., and Avoli, M. Low-Frequency Stimulation of the Amygdala Inhibits Ictogenesis in the Perirhinal Cortex. Epilepsia 2002; 43(s7): 129-130.

Khosravani H, Carlen PL, Velazquez JL. "The control of seizure-like activity in the rat hippocampal slice". Biophys.J 2003; 84: 687-695.

Kinoshita M, Ikeda A, Matsumoto R et al. "Electric stimulation on human cortex suppresses fast cortical activity and epileptic spikes". Epilepsia 2004; 45: 787-791.

Kinoshita M, Ikeda A, Matsuhashi M et al. "Electric cortical stimulation suppresses epileptic and background activities in neocortical epilepsy and mesial temporal lobe epilepsy". Clin Neurophysiol 2005; 116: 1291-1299.

Kossoff EH, Ritzl EK, Politsky JM et al. "Effect of an External Responsive Neurostimulator on Seizures and Electrographic Discharges during Subdural Electrode Monitoring". Epilepsia 2004; 45: 1560-1567.

Krauss GL, Fisher RS. Cerebellar and thalamic stimulation for epilepsy In: Devinsky O, Beric A, Dogali M, editors. Electrical and Magnetic Stimulation of the Brain and Spinal Cord. New York: Raven Press, 1993: 231-45.

Kwan P, Brodie MJ. "Early identification of refractory epilepsy". N.Engl.J.Med 2000; 342: 314-319.

Lesser RP, Kim SH, Beyderman L et al. "Brief bursts of pulse stimulation terminate afterdischarges caused by cortical stimulation". Neurology 1999; 53: 2073-2081.

Lew HL, Cifu DX, Sigford B, Scott S, Sayer N, Jaffee MS. "Team approach to diagnosis and management of traumatic brain injury and its comorbidities". J Rehabil.Res.Dev. 2007; 44: vii-vxi.

\* cited by examiner

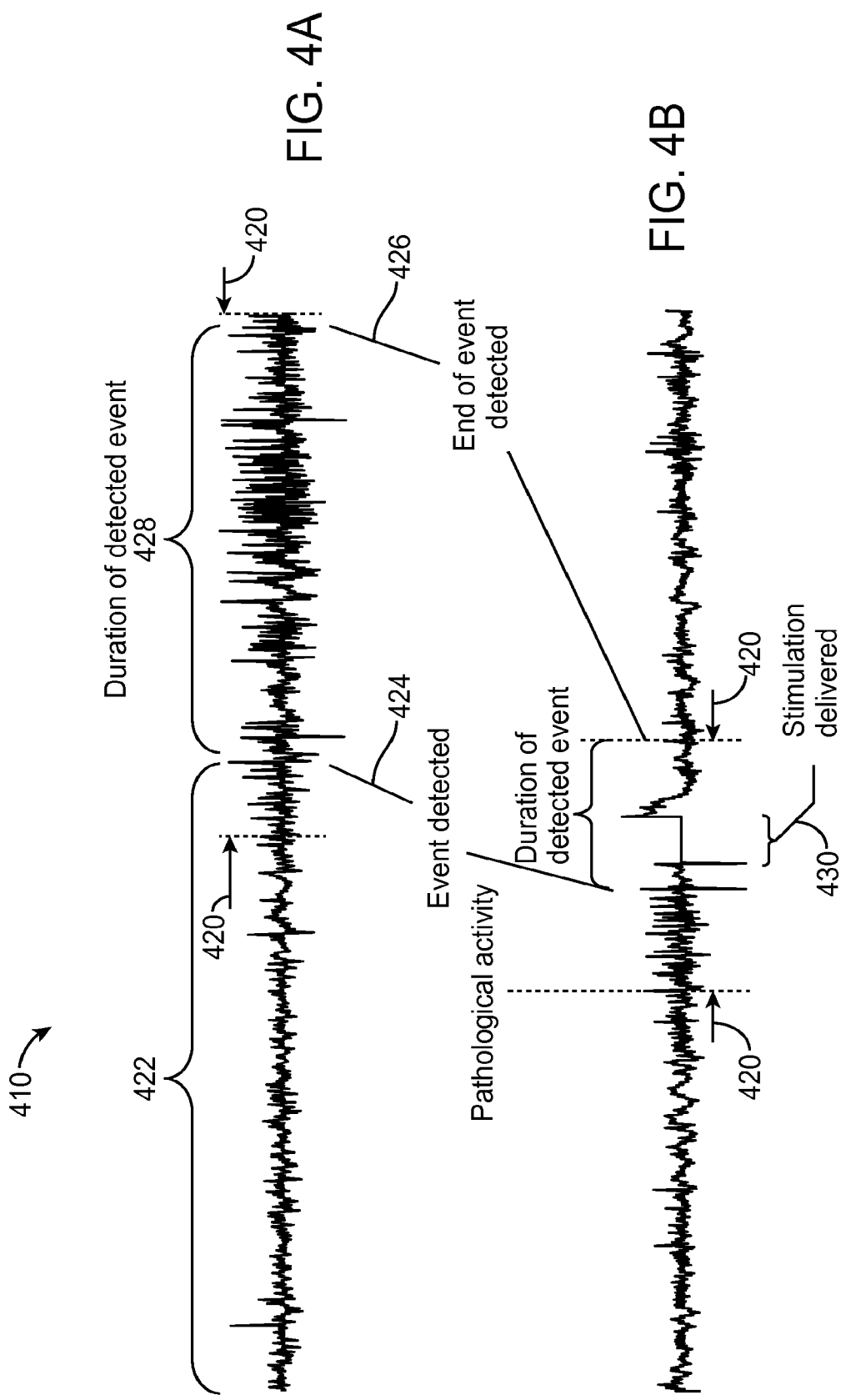

SYSTEMS AND METHODS FOR ASSESSING THE EFFECTIVENESS OF A THERAPY INCLUDING A DRUG REGIMEN USING AN IMPLANTABLE MEDICAL DEVICE

CROSS-REFERENCE TO RELATED APPLICATION(S)

This application is a divisional of U.S. application Ser. No. 13/539,301 filed on Jun. 30, 2012, entitled "Systems and Methods for Assessing the Effectiveness of a Therapy Including a Drug Regimen Using an Implantable Medical Device," which claims priority to and benefit of U.S. Provisional Patent Application No. 61/504,164 filed Jul. 1, 2011, entitled "Systems and Methods for Treating Neurological Disorders Using Neurostimulation and Drugs," each of which is expressly incorporated by reference herein in its entirety.

FIELD OF THE INVENTION

Embodiments generally relate to systems and methods for using an implantable medical device in combination with a drug therapy to treat a disorder or condition of the central nervous system.

BACKGROUND

Physicians often treat patients who suffer from a neurological disorder or otherwise present with an undesirable or unwanted neurological condition with a drug regimen in an effort to modulate the behavior of the central nervous system. A physician's choice of a drug or drugs to use and the dosage of each drug may be based on prior experience with the drug(s) and dosage(s) for patients who have been diagnosed with the same disorder or who present with the same condition. Often, however, the degree to which a drug regimen is or is not effective for a particular patient may depend on factors that are specific to that patient. Two patients with the same neurological disorder may not be equally well served by the same dose of the same drug, in terms of, for example, tolerance or efficacy. In addition, even when a drug regimen is well tolerated and effective for a given patient some of the time, it may not be well tolerated or effective all of the time.

Implantable medical devices are available or under investigation that enable physicians to treat patients who suffer from a neurological disorder with electrical stimulation therapy. A physician may treat a patient who has been implanted with a neurostimulator with both electrical stimulation therapy and a drug regimen in an effort to modulate the behavior of the central nervous system

BRIEF DESCRIPTION OF THE DRAWINGS

FIG. 4A is a time series graphical representation of an electrographic signal of the type that might be monitored by and acquired by according to embodiments.

FIG. 4B is another time series graphical representation of an electrographic signal of the type that might be monitored by and acquired by according to embodiments.

Figure 1:
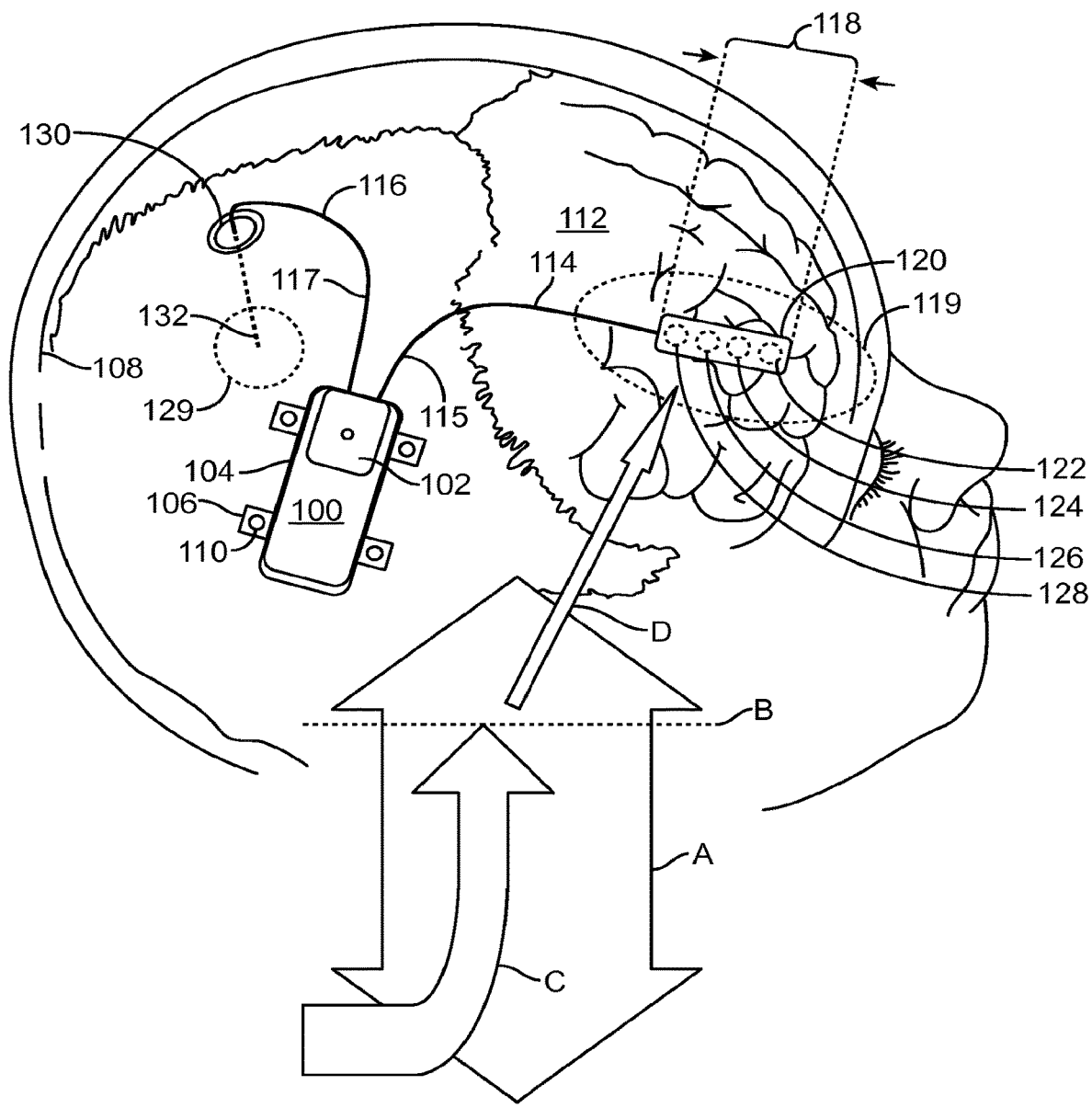
FIG. 1 is a schematic illustration of a patient's head in which an implantable medical device has been implanted.

The drawings referred to in this description should not be understood as being drawn to scale unless specifically noted.

DESCRIPTION OF EMBODIMENTS

Reference will now be made in detail to embodiments, examples of which are illustrated in the accompanying drawings. While the technology will be described in conjunction with various embodiment(s), it will be understood that they are not intended to be limited to these embodiments. On the contrary, the present technology is intended to cover alternatives, modifications and equivalents, which may be included within the various embodiments as defined by the appended claims.

Furthermore, in the following detailed description, numerous specific details are set forth in order to provide a thorough understanding of embodiments. However, embodiments may be practiced without these specific details. In other instances, well known methods, procedures, components, and circuits have not been described in detail as not to unnecessarily obscure aspects of embodiments.

Embodiments of systems and methods are described in which the effectiveness of a drug therapy to which a patient is subjected in order to treat or otherwise affect a neurological disorder or other neurological condition (hereinafter collectively referred to as "neurological disorder" or "disorder" for ease of reference but not by way of limitation) is measured relative to information acquired, processed, and analyzed by an implantable medical device.

Some embodiments provide for presenting information derived from the implantable medical device about the effectiveness of the drug therapy to the physician so that the physician may make adjustments to one or more the of the parameters that define the drug therapy (e.g., type of drug(s), dosage of drug(s), class of each drug, method of delivery of each drug, timing of delivery of each drug, etc.) with an objective of increasing the effectiveness of the drug therapy in treating the disorder. These embodiments rely, in part, on the capability of the implanted medical device to acquire, process, and analyze physiological data obtained from specific sensing locations in the patient's central nervous systems.

In other embodiments, information derived from the implanted medical device relating to the effectiveness of one drug therapy may be used to adjust either one or more parameters of that drug therapy to which the patient is subjected or, alternatively or additionally, to introduce another therapy to the patient that will be used, together with the first drug therapy to treat the patient. These embodiments rely, in part, on the capability of the implanted medical device to elucidate synergistic (or antagonistic) relationships between a drug therapy to which the patient is subjected and another therapy to which the patient may be or already also is subjected.

By way of example, an additional therapy may be one that is designed to modulate the behavior of the patient's central nervous system in the same or a different way than is a first drug therapy and may include, for example, a form of electrical stimulation therapy or a form of optical stimulation. An additional therapy may also include a form of drug therapy that is different than the form of a first drug therapy (e.g., the first drug therapy may include a pill administered orally, and the additional therapy may include a drug delivered directly to a desired location in the patient's brain (e.g., via a needle or a catheter or an active implant configured to controllably deliver a drug from, for instance, a drug reservoir)).

In still other embodiments, information derived from the implanted medical device relating to the effectiveness of a drug therapy may be used to change one or more parameters of an additional therapy the patient is receiving (e.g., if the patient is receiving electrical stimulation therapy in addition to the drug therapy, the information derived from the implanted medical device may be used to adjust one or more parameters of the electrical stimulation therapy in an effort to improve the response of the patient to the combination of the drug therapy and the electrical stimulation therapy).

In yet further embodiments, information derived from the implanted medical device may be used to adjust one or more parameters of any of multiple therapies the patient is receiving or may receive, in an effort to achieve an optimum efficacious result from the combination of therapies.

In some cases where adjusting of parameters occurs, the adjustment may be initiated and undertaken automatically, for example, using one or more algorithms and outputs generated by the implantable medical device or from a different implantable medical device or some other source of a form of therapy. In other cases, an adjustment may be initiated by a physician and then undertaken by implementing the adjustment using an implantable medical device or other source of a form of therapy. In still other cases, the adjustment may be initiated by the physician and undertaken by the patient (e.g., when the adjustment is to take a different pill or take the same or a different pill at a different time of day).

The discussion that follows will describe the structure and functionality of embodiments.

FIG. 1 is a schematic illustration of patient's head in which the implantable components of an implantable medical system according to systems and methods of the embodiments have been implanted and representations of movement and targeting of a systemically-delivered drug or medication are indicated using arrows and dashed lines.

Generally, physicians often treat patients with a disorder of the nervous system using one or more medications in an effort to help control the disorder. These medications usually are believed to modulate the behavior of the nervous system in some way. How a given drug modulates nervous system behavior may depend, in part, on circumstances at one or more localized areas in the nervous system or functional circuits in the brain. These circumstances can include variables related to local functioning of the neural tissue (i.e., neurophysiology), such as the overall number of action potentials occurring within a region (i.e., neural activity or neural firing); the type of action potentials, such as inhibitory or excitatory; or the temporal or spatial pattern of action potentials. These circumstances may also include variables such as regional cerebral blood flow or fraction of oxygenated hemoglobin related to other physiological processes such as hemodynamics. Of course, the action of a drug also may be affected by other conditions of the patient and whether the patient is also receiving some other form of therapy to treat the disorder, such as electrical stimulation therapy.

Medications for diseases of the nervous system commonly are taken systemically. However, the physician may hope and expect that the drug will have a particular effect at a certain location or functional circuit in the nervous system or a part of the nervous system. Examples of physical locations in the brain may include an epileptic focus or deep brain nucleus, or a physical location elsewhere in the nervous system, such as a peripheral ganglion. Alternatively or additionally, in some cases, the physician may hope and expect that the drug will have a particular effect on a functional circuit of the brain which may functionally connect nerve cells from a variety of locations within the nervous system.

While both the desired effect(s) and the patient's ability to tolerate the drug may depend on the concentration of the drug at the particular physical locations or in the functional circuits, this concentration is often not easy to predict just using only data concerning the drug type, the dosage, the class of drug, the method and timing of dosing, and the physical characteristics of the patient (e.g., sex, height, weight, age, etc.). If the concentration at a location of interest is too low (or too high), it may be partially or entirely ineffective in achieving the desired result. If the concentration of a drug at a location of interest is too high (or perhaps under some circumstances too low), the drug may be effective to some degree but it nevertheless may not be well tolerated by the patient (e.g., it may be toxic to the patient or may cause the patient to experience one or more undesirable, unpleasant, or quality-of-life-altering side effects).

The effectiveness and the extent to which a patient tolerates a given medication also may depend on whether the concentration of the drug remains stable at the location(s) of interest during the time the patient is intended to experience the benefits believed to be associated with the drug. Measuring changes in drug concentration over time in a patient can be challenging. While the systemic concentration of a medication can be measured by assays of serum, such serum assays will not directly convey the concentration of a given drug at a specific location or circuit of interest in the neural tissue or even generally in the central nervous system.

Moreover, it will be appreciated that a serum assay will only yield information about the concentration of the drug as of the time the serum is sampled, and in order to monitor changes in the concentration over time, either additional samples will need to be taken and assays run or certain inferences about how the concentration of the medication will change over time will have to be made. Also, some drugs have an effect at a location of interest which is not related directly to the serum concentration. For example, some medications have a long-lasting effect after a single or several doses, even after the serum concentration has fallen.

In some circumstances, a driver for providing a patient with additional doses of the medication is not related to the serum concentration but instead to when the physiological effect of the medication ends or subsides. An example of this is the antiepileptic medication vigabatrin. Vigabatrin increases the levels of the inhibitory neurotransmitter GABA by irreversibly inhibiting an enzyme that catabolizes GABA (gamma-aminobutyric acid transaminase). When GABA levels are high, seizures are inhibited. As the enzyme is naturally replenished in the brain, GABA levels fall and seizures are more likely to occur. At this time the medication should be readministered. Thus, in some circumstances, the optimal timing for doses may be better determined by monitoring the physiological effect of the medication in the central nervous system rather than by monitoring the level of the medication in the serum, as by for example a serum assay.

Therefore, it is desirable to assess information relating to the concentration of a drug or drugs used in a drug therapy using physiological data acquired at or near the location(s) at which the drug is intended to act (either a physical location or a part of a functional circuit of the nervous system). Moreover, it is desirable to assess this information frequently enough to determine whether the effectiveness of the drug at the locations(s) of interest remains stable or varies during the time when the drug is intended to be effective.

Referring again to FIG. 1, an arrow A indicates the function of the circulatory system, the dashed line B indicates the blood-brain barrier, the wide single-headed arrow C indicates the path of a medication in the circulatory system up until the blood-brain barrier B is encountered, and the narrow, single-headed arrow D indicates that amount of the medication that successfully crosses the blood-brain barrier and makes it to a location of interest within the area denoted by the broken circle 119 in FIG. 1.

More specifically, a patient may be subjected to a drug therapy that includes the patient receiving a drug systemically (e.g., by ingesting or otherwise taking a pill or receiving an injection in the blood stream other than directly at a location at which the drug is intended to act). A medication that is administered systemically to a patient is conveyed to the brain by the systemic circulation and then must cross the blood-brain barrier (see the broken line B in FIG. 1) to be distributed throughout the brain by the cerebrovascular circulation.

The actual concentration of the medication at a given location in the neural tissue (e.g., in FIG. 1, a location of interest within the broken circle 119 is receiving the medication directed to it by the cerebrovascular circulation, which is indicated generally with the arrow D) may vary according to the timing at which doses are taken and according to the pharmacokinetics of the medication, which may vary across individuals and even within an individual over short and long periods of time. Therefore, an amount of medication that will be available to neural tissue at a location of interest is difficult to predict even when the precise dose is known (e.g., assuming the patient takes her pills when she is supposed to), or even when an assay of the concentration in the serum is undertaken (e.g., by periodically sending the patient's blood to a laboratory for analysis).

Additionally, the pharmacodynamic effects of a given medication at a location in the neural tissue may vary across and within individuals. Thus, the therapeutic effects and side effects of the medication at a given dose or serum concentration may vary over time and across patients even when the treating physician's hope and expectation is that the medication will affect the same location(s) or functional circuit(s) in each patient.

Moreover, in some cases, the physician may not always appreciate how a given drug works or at which locations it works more or less effectively to achieve a desired result. Ultimately, the physician wants to know what the functional concentration of the medication is at the neural tissue of interest, that is, whether the medication is having the desired effect. When the physician has an understanding of this the physician can adjust the dose in order to achieve the desired effect.

FIG. 1 shows an implantable medical device 100 situated in a structural member inserted into the opening formed in the skull by the craniectomy, which structural member is commonly referred to as a ferrule. The ferrule 104 provided with mounting tabs 106 for attaching the ferrule to the cranium (or skull) 108. The mounting tabs 106 include screw-holes 110 or other apertures for receiving bone screws to secure the ferrule 104 to the skull 108. The implantable medical device 100 may be configurable to monitor physiological activity originating from or sensed from one or more sensing locations in the patient's brain 112.

More particularly, the implantable medical device 100 may be configured to monitor signals corresponding to field potential measurements acquired using one or more electrodes placed in or on the brain 112 or to acquire other physiological data corresponding to a state of the neural tissue, such as the level of neurochemicals in the tissue (for instance, the concentration of neurotransmitters in a particular location in the brain), and the degree to which the tissue is oxygenated, etc.

In FIG. 1 the implantable medical device 100 is shown connected to two brain leads, a cortical strip lead 114 and a deep brain or depth lead 116. A proximal end 115 of the cortical strip lead 114 and a proximal end 117 of the depth lead each are connected to the implantable medical device 100 at a lead connector 102. A distal portion 118 of the cortical strip lead 114 is provided with a strip 120 which is designed to rest against or adjacent a surface of the patient's brain 112, such as under the dura mater (not shown in FIG.

1), at a location on the brain 112 within the broken circle 119. The distal portion 118 bears four disk-shaped electrodes 122, 124, 126, and 128 which are in electrical communication with the proximal end 115 of the cortical strip lead 114 and with the implantable medical device 100 via conductors in the cortical strip lead 114 (see also FIG. 2A) and via the implantable medical device connector 102.

The depth lead 116 is implanted at a location in the brain within the broken circle 129 in FIG. 1. The depth lead 116 is implanted through a burr hole 130 that has been drilled in the skull 108 to allow the surgeon access to the patient's brain as, for example, in a stereotactic procedure. Like the cortical strip lead 114, the depth lead 116 is provided with electrodes at a distal portion 132 thereof. (The ring electrodes of the depth lead 116 are shown in FIG. 2B.) The electrodes of the depth lead 116 are also in electrical communication with the proximal end 117 of the depth lead 116 and with the implantable medical device 100 via conductors in the depth lead 116 (see also FIG. 2B) and via the implantable medical device connector 102.

Figure 2A:
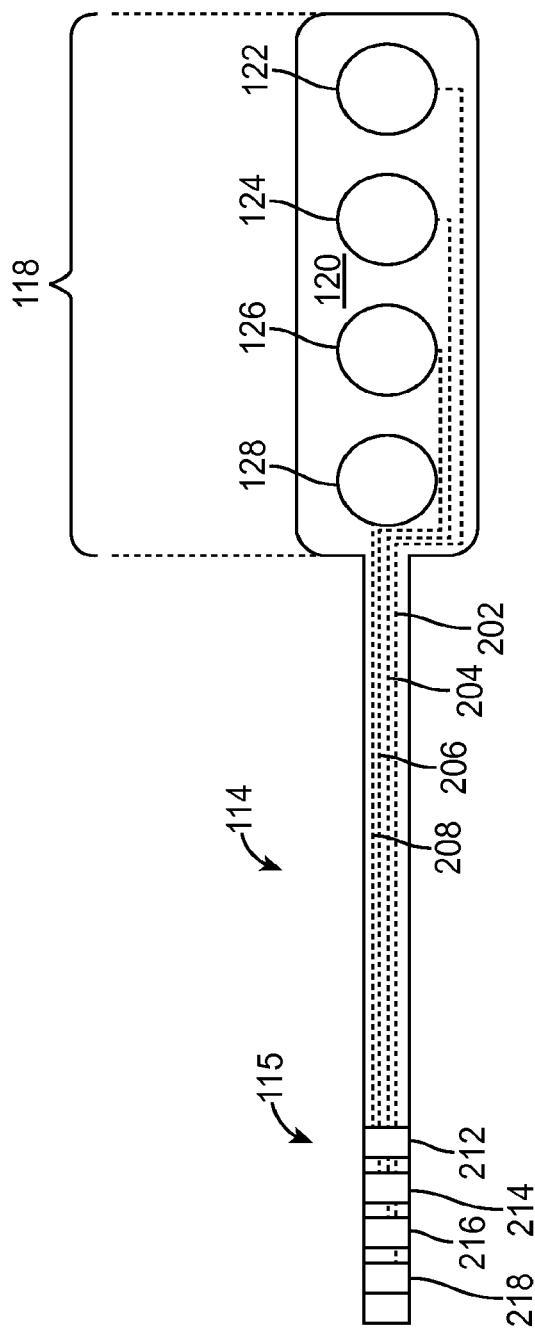
FIG. 2A is a schematic representation of an electrode-bearing cortical strip lead that may be used for sensing physiological signals and/or delivering electrical stimulation to a patient.
Figure 2B:
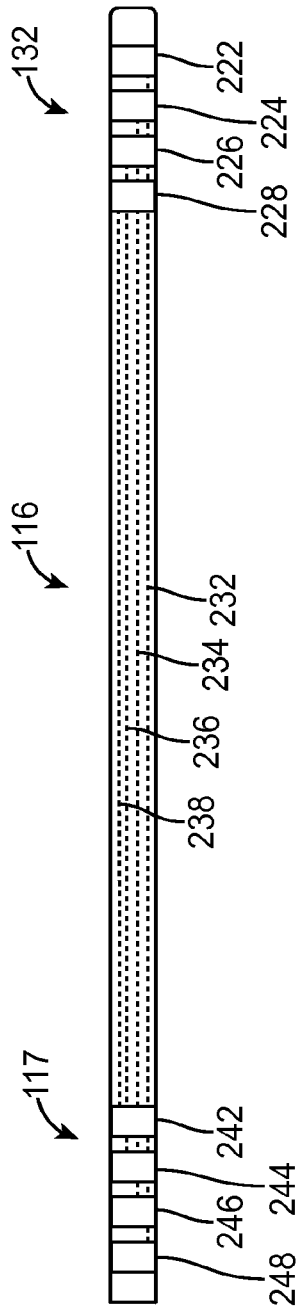
FIG. 2B is a schematic representation of an electrode-bearing depth or deep brain lead that may be used for sensing physiological signals and/or delivering electrical stimulation to a patient.

Referring now to FIGS. 2A and 2B, illustrations of the cortical strip lead (FIG. 2A) and a deep brain or depth lead (FIG. 2B) are shown. The figures are not drawn to scale. The cortical strip lead 114 has a proximal end 115 and a distal portion 118. The distal portion 118 is provided with a cortical strip 120 and four disk-shaped electrodes 122, 124, 126, 128. Each disk-shaped electrode 122, 124, 126, 128 is configurable to be in electrical communication through a dedicated conductor 202, 204, 206, 208 with one of four connection surfaces or contacts 212, 214, 216, 218 at the proximal end 115 of the lead 114. The connection surfaces or contacts 212, 214, 216, 218 can make electrical contact with the implantable medical device 100 via the connector 102 of the implantable medical device with which the proximal contacts 212, 214, 216, 218 are configured to mate. The depth lead 116 has a proximal end 117 and a distal portion 132. The distal portion 132 is provided with four ring electrodes 222, 224, 226, 228. Each ring electrode 222, 224, 226, 228 is configurable to be in electrical communication through a dedicated conductor 232, 234, 236, 238 with one of four connection surfaces or contacts 242, 244, 246, 248 at the proximal end 117 of the depth lead 116. The connection surfaces or contacts 242, 244, 246, 248 can make electrical contact with the implantable medical device 100 via the connector 102 of the implantable medical device (with which the proximal contacts 242, 244, 246, 248 are configured to mate). Each of the disk-shaped electrodes 122, 124, 126, 128 and the ring electrodes 222, 224, 226, 228 may be constructed of a biocompatible, conductive material such as platinum or a platinum/iridium alloy.

In addition to or in lieu of one or more electrodes on the leads described with reference to FIGS. 2A and 2B, the implantable medical device 100 may be used with other sensors or probes (not shown). Such other sensors or probes may be either hard wired or in wireless communication with the implantable medical device 100 so that the device may monitor physiological data other than data acquired using the electrodes. For example, probes for oximetry and micro/macroelectrode configurations for accomplishing voltammetric measurements relating to neurochemical concentrations may be used to provide other physiological data to the implantable medical device 100. A probe may be used to acquire a signal corresponding to the level of the near-infrared wavelength characteristic of light absorption by oxygenated hemoglobin (HbO2). This signal may be used to estimate a level of neural activity. For instance, the neurovascular coupling system causes vasodilation and increased cerebral perfusion in response to neural activity, such that, after an initial drop in oxygenated hemoglobin at the onset of increased neural activity, increased neural activity is then accompanied by an increase in oxygenated hemoglobin.

Variations of sensors or probes may be implemented using transducers for additional sensing modalities such as optical infrared spectroscopy. A given sensing modality may rely upon active electronics provided in the lead, especially at a distal portion of a lead close to where the physiological data is being sensed, to acquire physiological data for use by the implantable medical device. Alternatively, a given sensor may be associated otherwise locally with active electronics and the sensor information acquired may be communicated to the implantable medical device wirelessly.

While the implantable medical device 100 is shown at a particular location on the patient's head, it will be appreciated that it may be located elsewhere. For example, the implantable medical device 100 may be situated in a hole formed by a craniectomy at another site on the skull, or may be situated in a recession made in the skull, or between the scalp and the skull. In other cases, the implantable medical device 100 may be implanted further away from the location at which the physiological data it monitors originates or is generated. For example, it is known to situate an implantable medical device in the pectoral area of a patient and then to place the implantable medical device in communication with the patient's brain using leads that extend from the implantable medical device through the patient's neck up to the brain, where electrode-bearing lead distal ends can be introduced to one or more locations on, adjacent to, or in the patient's brain tissue.

In still other circumstances, the implantable medical device may be used to accomplish one or more of its intended functions, e.g., to monitor physiological data sensed by one or more sensors, without the implantable medical device actually being implanted (for instance to perform a short-term test to confirm that the electrodes of a brain lead are in the desired location) or with the implantable medical device being only partially implanted.

In addition to being configurable to monitor physiological data, the implantable medical device 100 in some embodiments may also be configurable to generate and output electrical stimulation which electrical stimulation may be delivered to the patient through pathways formed, for example, between electrodes on the distal end of a brain lead or between one or more electrodes on the distal end of a brain lead and a conductive housing provided for the implantable medical device 100.

An implantable neurostimulation system manufactured under the tradename "RNS SYSTEM" by NeuroPace, Inc. of Mountain View, Calif. is under investigation that is configurable to acquire, process, and analyze electrographic activity from a patient and to generate and deliver electrical current stimulation to the patient, for example, in response to the results of the analysis of the electrographic activity. More specifically, this neurostimulation system is configurable to continuously monitor and on command record electrographic activity sensed from one or more sensing locations on or adjacent or in a patient's brain. The neurostimulator further may be configured to implement various analytic tools, in sequence or in combination, that are intended to detect events of interest when the events occur in the monitored electrographic activity. Whenever an event is detected, the neurostimulator may store one or more records corresponding to the electrographic activity at the time the event is detected, as well as other information about the event, for example, the time the event began, the length of time the event continued to be detected, the time between one event and the next event, etc.

The NeuroPace neurostimulator is being investigated for use in applications to treat patients who have epilepsy. It can be used with either or both of electrode-bearing cortical strip leads and depth leads where the neurostimulator can be programmed to recognize each electrode as a part of one or more sensing "channels" and programmed to include each electrode as part of a pathway through which electrical current can flow through the patient.

Thus, in the NeuroPace, Inc. RNS System as well as in some embodiments described herein, the factors a physician considers in determining where to locate the electrodes of a brain lead include selecting stimulation locations at which or through which to introduce an electrical current to the brain as well as selecting locations appropriate to sensing physiological data that can be monitored by the implantable medical device using the leads. Indeed, it will be appreciated that in any circumstance in which an element may be used to implement both a monitoring or sensing function and a function intended to modulate the neurological behavior of the patient's brain, the location of the element will require thoughtful consideration and likely the weighing of factors and prioritizing of various hoped-for outcomes.

In some circumstances, the electrodes may be situated at or near a location in the brain that is understood to constitute a focus of epileptiform activity (e.g., an epileptic focus). In other circumstances, the electrodes may be implanted at a particular nucleus deep in the brain which is understood to have some connection to the particular neurological disorder for which the patient is being treated, such as a deep brain nucleus exhibiting pathological behavior in a patient with epilepsy or a movement disorder. Locations for electrodes for sensing or other sensors of physiological data or for stimulating areas of the brain can include regions of neural tissue located in the brain 112, regions of neural tissue located outside the brain, such as cranial or peripheral nerve ganglia, or regions of non-neural tissue such as cardiac or muscle tissue.

It will be appreciated that sensing physiological data from one sensing location may relate to behavior of a physical location that is remote from the sensing location or may relate to the function of a neural circuit, the components of which are physically spread out through the nervous system. It further will be appreciated that the desired effect of stimulation at a given stimulation location may not be fully realized or realized at all at the stimulation location itself, but rather is realized at a region distant from that location. For example, the desired effect of stimulating a given location of interest may be to cause excitation (or inhibition) of neurons located remote from that location of interest but which receive excitatory (or inhibitory) neural projections from the location of interest. The systems and methods disclosed here beneficially may be used when the locations used for sensing physiological data or for delivering a form of neuromodulation therapy are either directly or indirectly related to the condition being sensed or the behavior a given therapy is intended to modulate.

Further, it will be appreciated that the implantable medical device may be configurable to deliver forms of therapy using elements other than electrodes, such as via drug-eluting leads or components for administering optical stimulation.

Figure 3:
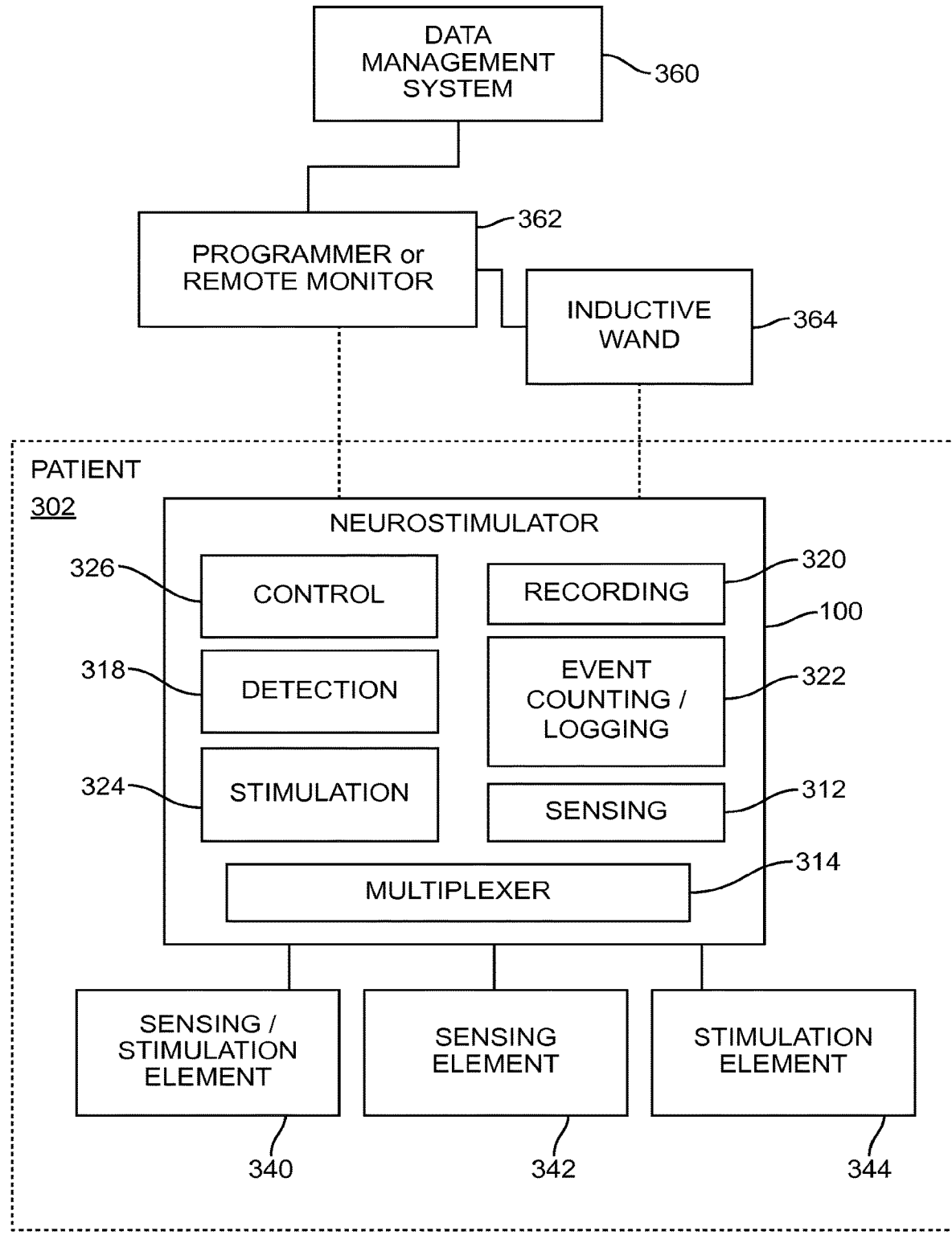
FIG. 3 is s block diagram illustrating some of the components and features of a neurostimulation system.

Referring now to FIG. 3, a block diagram of systems and methods according to embodiments is shown. In these embodiments, the implantable medical device 100 is an implantable neurostimulator that is configurable to generate and output a form of electrical stimulation for delivery to the patient according to a set of programmable stimulation parameters. The various blocks shown in FIG. 3 (and in any other similar drawing figure included herein) are used for convenience in the discussion of some of the functions the implantable neurostimulator 100 is configurable to undertake. It will be appreciated that the various functions and capabilities of the "modules" or "subsystems" depicted in the block diagram may be performed by electronic hardware, computer software (or firmware) or any combination thereof. The actual division of work for each of the various functions may not be well represented by the blocks shown in the diagram of FIG. 3 and the diagram may not reflect a real-world integration of the functions into a system or method according to embodiments.

The implantable medical device 100 is also configurable to acquire information relating to physiological data sensed from the patient, and to process and analyze the information.

The acquiring may include selecting which of several channels from which to accept input. In FIG. 3, a "sensing" module 312 and a "multiplexer" 314 are shown in the implantable medical device 100. For example, the implantable medical device 100 may be configured to receive inputs corresponding to one or more channels of physiological data acquired from the sensors (e.g., electrodes). FIG. 3 shows a "sensing/stimulation" element 340 that is capable of being configured either to sense physiological data from or deliver stimulation to the patient 302, as well as an additional "sensing" element 342 that is dedicated for use in sensing. A sensing/stimulation element 340 may comprise an electrode that can be configured to sense physiological data from a patient (e.g., a field potential measurement corresponding to electrical activity in the area in which the electrode is implanted) and that can be configured to deliver an electrical current to the patient (e.g., through a pathway that includes the electrode). A sensing element 342 may comprise an electrode for measuring field potential changes in electrical activity of the brain, or a component or collection of components configured to sense some other type of physiological data, such as an optical sensor configured to detect wavelengths of infrared light corresponding to oxygenated and deoxygenated hemoglobin.

In some embodiments, the implantable medical device 100 may be configured to acquire information from one or more sensing elements 342 that are situated in one or more locations in a patient to measure levels of a neurochemical. This information may include pH, tissue oxygenation, and/or neurotransmitter levels. During periods of increased neural activity, energy utilization by neural tissue results in increased metabolism that lowers extracellular oxygen concentrations and pH. At the same time, chemical messengers are released by neural tissue that result in vasodilation and an increased supply of nutrients. This vasodilation increases blood flow, re-supplying oxygen and clearing carbon dioxide. Because vasodilation overcompensates for the metabolic effects, the net result is an increase in oxygen levels and an alkaline shift that occur following increased neuronal activity. Both chemical changes are transient and approximately simultaneous, occurring a few seconds after the electrical activity. Both oxygen and pH levels can be measured in the brain using fast-scan cyclic voltammetry. Extracellular oxygen levels can also be measured using optical recording of intrinsic signals (ORIS). ORIS relies on the differential absorption of oxygenated (Hb02) and deoxygenated hemoglobin (Hbr). At isobestic wavelengths (525, 545, 570.5 and 583 nm) Hb02 and Hbr reflect light equally and thus the resulting signal reflects total hemoglobin. Total hemoglobin is directly proportional to cerebral blood volume and cerebral blood flow giving a measure of tissue perfusion. At higher wavelengths (605-650 nm), the majority of the signal comes from Hbr since Hbr has a higher absorption coefficient than Hb02. Using ORIS may require using light emitting diodes to illuminate and an isolated photosensitive diode to detect the reflected light. Similar technology has been used in to detect oxygen saturation in cardiac tissue. Alternative technologies for sensing oxygen include quench fluorescence and impedance plethsymography.

Voltammetry can also be used to measure levels of specific neurotransmitters, such as dopamine, adenosine, serotonin, and norepinephrine or electrochemically active neuropeptides such as oxytocin and vasopressin. Other or additional neurotransmitters, including glutamate and GABA may be measured using methods including but not limited to fixed potential amperometry at enzyme-linked biosensors.

Either the programmable parameters for configuring the implantable medical device 100 to identify characteristics in the sensed physiological data or the programming instructions that control the device's central processing unit (and thus its overall operation) or some combination of both define, at any given time during when the device is functioning to monitor physiological data from the patient, which input signals representing which physiological data are connected to which sensing channels that are configured in the implantable medical device.

A multiplexer function is provided in the implantable medical device 100 and is labeled as "multiplexer" 314 in FIG. 3 and also may be referred to herein as "the multiplexer module". In some embodiments, the multiplexer 314 routes signals coming into the implantable medical device, such as voltages corresponding to sensed physiological data, to amplifiers or other signal processing circuitry, for example, signal processing circuitry that forms a part of the functions carried out by the sensing module 312.

The sensing module 312 is provided in the implantable medical device 100 and may be configured to receive signals or other data acquired by the implantable medical device 100 and process the signals and/or data into a form that can be used by the other modules of the implantable medical device, such as the detection module 318, the recording module 320, the event counting/logging module 322 and the control module 326. The functions of the sensing module 312 may include converting an analog signal to a digital approximation of the signal. The sensing functions of the implantable medical device 100 may also include amplifying, low-pass filtering, high-pass filtering, bandpass filtering, and/or bandstop filtering of signals. The processing may include such things as debouncing, conditioning, smoothing, low-pass filtering, or high-pass filtering of a signal indicative of the level of a physiological measurement. The processing may be undertaken as part of one or more of the functions of "sensing" and "detection" indicated by the sensing module 312 and detection module 318 in FIG. 3.

The detection module 318 is provided in the implantable medical device 100 and is configurable to analyze and evaluate signals or other data corresponding to physiological data acquired by the implantable medical device. The analyzing may include applying one or more algorithms to the acquired and processed physiological data and, optionally, comparing one or more results of the algorithms to a value, such as a fixed or dynamic threshold. The analyzing may be undertaken on physiological data in the form of an EEG signal (e.g., an electrocorticogram (ECoG)) sensed from inside the skull (as opposed to sensed through the skull, as with a scalp electrode), in the form of a different electrophysiological waveform (e.g., a waveform corresponding to changing levels of neurotransmitter concentration in a time window), or in the form of a sensor measurement that is not necessarily acquired as a waveform (e.g., a temperature or pressure measurement, a tissue oxygenation level, or an accelerometer reading (to indicate rest or sleep versus movement or an awake state)).

In some embodiments, the analyzing and evaluating includes detecting certain pathological events, such as a spike or a seizure that is discernable in a sample of electrographic activity sensed from the patient's brain. The analysis may further include identifying half waves in the sample, evaluating a line length trend and an area trend for the sample, and comparing the results of the analysis to one or more limits or thresholds.

More particularly, in an embodiment, the implantable medical device 100 can be configured to analyze data it acquires corresponding to field potential measurements sensed using electrodes with one or all of three tools, known as the half-wave tool, the line-length tool, and the area tool, each of which is described in more detail below and, for example, in U.S. Pat. No. 7,966,073 issued Jun. 21, 2011 for "Differential Neurostimulation Therapy Driven By Physiological Therapy" to Pless et al. U.S. Pat. No. 7,966,073 is incorporated herein by reference in the entirety. The tools may be implemented in a combination of hardware and software, or entirely in one or the other, depending on overall system requirements such as power consumption limitations.

By way of example, in some embodiments, where the physiological data being sensed is a field potential corresponding to an electrical activity of the patient's brain, each sensing channel of the detection module receives a bipolar signal representative of the difference in electrical potential between two selectable electrodes. An interface in the implantable medical device 100 with the sensors (such as an electrode selector) provides signals corresponding to each pair of selected electrodes to a sensing front end of the detection module. The sensing front end amplifies the incoming signal(s), converts the signal from analog to digital form, and multiplexes the signals on the sensing channels.

Preferably, any of the electrodes can be used differently depending on a preferred monitoring configuration. For example, an electrode may remain unused while the detection module is monitoring physiological data sensed by other electrodes such that the unused electrode is not connectable to a sensing channel with the electrode selector. Alternatively, an electrode may be coupled to either a positive or a negative input of a single sensing channel or an electrode may be coupled to the positive (or negative) inputs of multiple sensing channels.

A multiplexed input signal representative of all sensing channels that are active during monitoring may be fed from the sensing front end to a data analyzer. The data analyzer may be a special-purpose digital signal processor (DSP) adapted for use in the detection module. Alternatively, a programmable, general purpose DSP may be used in the detection module 318.

The half-wave tool, the line-length tool, and the area tool each may be characterized as a tool for analyzing an EEG. There may be multiple instances of each of these tools associated implementable in the detection module, having detection parameters that can be programmed with different values. Different instances of the tools may be selectable to operate on the data processed through different sensing channels. The results of the tools may be used alone or in combination to decide whether an "event" should be deemed to have been "detected" in the sample of the signal analyzed.

The half-wave tool measures characteristics of an EEG (or ECoG) signal related to the dominant frequency content of the signal. In general terms, a half wave is an interval between a local waveform minimum and a local waveform maximum; each time a signal "changes directions" (e.g., from increasing to decreasing or from decreasing to increasing), and subject to limitations that are set forth further below, a new half wave is identified. The half wave tool, particularly when used on filtered EEG data, can be used to identify the presence of signals in particular frequency ranges over certain periods of time, such as a frequency range that correlates well with a time when a patient is experience seizure activity. In an embodiment, for example, the analysis performed by the detection module 318 includes detection of power within a frequency band, such as from 13 to 30 Hertz, by analyzing half-waves that occur in one or more time windows in a sampled electrographic signal sensed from the patient's brain and acquired by the implantable medical device 100.

The line length tool is a simplification of the fractal dimension of a waveform, and reflects how much an EEG signal is varying in a given time window.

The area tool is a simplification of the energy of a waveform, and involves calculating the area under the curve of a EEG signal within a certain time window.

Specific implementations of each of a half-wave tool, a line length tool and an area tool are described in U.S. Pat. No. 6,810,285 to Pless et al. for "Seizure Sensing and Detection Using an Implantable Device", issued Oct. 26, 2004. This patent also describes particular applications of the tools in a system including an implantable neurostimulator which, among other things, continuously acquires electrographic signals sensed from a patient and processes and analyzes the acquired data to monitor for certain "events" (e.g., a pattern in a certain time window or a certain combination of a pattern and some other characteristic of the acquired data or a condition of the implantable neurostimulator), and to register a "detection" or "detected event" whenever the event occurs. The detected events may be used in a form of treatment for a patient experiencing seizures or "ictal" or "epileptiform" activity, such as a form of treatment involving delivering a therapy of electrical stimulation whenever an event is deemed to have been detected by the implantable neurostimulator. U.S. Pat. No. 6,810,285 is incorporated herein by reference in the entirety.

Different or additional tools may be used to evaluate EEG waveforms, other electrophysiological waveforms and other sensor data in accordance with embodiments. For example, an EEG waveform may be analyzed in the frequency domain by a tool that involves fast Fourier transforms (FFTs). The analysis tools may be used alone or in combination (e.g., in a Boolean combination) to analyze the physiological data sensed from the patient. A tool or tools may be implemented entirely by the implantable medical device or in part by the implant and in part by one or more external components. Physiological data acquired by the implantable medical device 100 may be subjected to more than one tool at the same time or to one tool followed by another tool.

The analyzing may include comparing a result of an algorithm or algorithms with one or more thresholds, fixed or dynamic, or other values. The results can be logically combined, thresholded, trended, or subjected to further analyses or processing steps as necessary to detect neurological events or states, or to identify other characteristics in the acquired physiological data according to embodiments.

In an embodiment, any detection tool or other algorithm for analyzing data with the detection module 318 easily may be tuned to operate on essentially any kind of source data. It will be apparent that detection of a pathological event or pathological activity can include the condition occurring when the output of one of these analysis tools exceeds or falls below a threshold, such as a programmable parameter representing the threshold between normal physiological variation and pathological neural activity. It also will be apparent that a pathological event may be deemed to have been "detected" when a combination of conditions occurs, such as a Boolean AND combination, Boolean OR combination, or other logical combination, or a time sequence of such conditions occurring such as the output of a first analysis tool exceeding a first threshold followed within one second by the output of a second analysis tool exceeding a second threshold.

In some embodiments, the detection module 318 is configured to analyze the acquired physiological data by determining a quantity or a quality of periodic variation with which the acquired physiological data is characterized. This quantity or quality of periodic variation may comprise one or more of an ultradian, circadian, or circalunar variation. The quantity or quality of periodic variation may be identified as a characteristic of a physiological data subjected to a line length tool (e.g., identified based on the variation of line length of an electrocorticographic signal averaged over time or a count of pathological events).

Determining the quantity or quality of the periodic variation may involve one or more of the following analytic approaches: (1) determining a frequency or period of the periodic variation; (2) determining a modulation depth of the periodic variation; (3) determining an autocorrelation of a physiological measurement (e.g., wherein successive values of the physiological measurement are correlated with each other and the degree of correlation is quantified in some manner relative to the successive values); (4) determining a correlation or a coherence between multiple physiological measurements; (5) determining a phase of a periodic variation with respect to a phase of a different physiological measurement; and (6) determining a phase of a periodic variation with respect to a time interval such as calendar days, 28-day intervals, a patient's sleep cycle, a patient's medication schedule, or a patient's menstrual cycle.

The quantity or quality of period variation with which the acquired physiological data is characterized may be useful, for example, in assessing whether a drug regimen to which the patient is subjected is effective or the time or times when the drug regimen is or is not effective. For example, the effectiveness of a medication may be estimated to be inversely proportional to the autocorrelation of the count of events at a 28-day time difference. Based on this information, the physician may choose to change the time at which the drug is taken so that the peak concentration corresponds to times when the physiological data indicates that the drug is less effective, and/or change the dosage on certain days of the month (such as over a menstrual cycle) during which the physiological data indicates that the drug is less effective or even change the drug entirely.

The implantable medical device 100 further is configurable to store information relating to the sensed physiological data (e.g., waveforms or filtered or processed waveforms), store information relating to one or more conditions of the neurostimulator at the time the sensed information is acquired (e.g., a date/time stamp, whether an amplifier in a sensing channel of the neurostimulator is saturated and, if so, for how long etc.), or store information relating to the form of stimulation delivered to the patient, if any (e.g., information with which a delivered stimulation waveform may be identified or recognized, information corresponding to whether a desired amplitude of stimulation was achieved, etc.).

The storing may be undertaken as part of one or more of the functions of "recording" and "event counting or "event logging" indicated by the recording module 320 and event counting/logging module 322 shown in FIG. 3. For example, if the implantable medical device 100 is configured to identify a characteristic in the physiological data it acquires as an "event" which the neurostimulator "detects", then a function of the implantable medical device may be to keep track of how many detected events occur over a fixed period of time (e.g., 24-hours) or a variable period of time (e.g., during a time when the patient is experiencing symptoms associated with the neurological disorder for which the patient is being treated).

In this same example, another function of the implantable medical device may be to store the sample of acquired physiological data in which each "event" was "detected" (or a digitized or otherwise processed transformation of the sample), so that, for instance, a physician may later review the sample by interrogating the information stored on the implant. If the physiological data includes electrocorticograms sensed by measuring field potential changes at one or more sensing locations in the patient's brain, then what the implantable medical device records may comprise electrographic records. The running count of the number of detected events may be stored in the event counting/logging module 322 and the electrocorticogram may be recorded in the recording module 320.

In some embodiments, the implantable medical device 100 is configurable to generate and output a form of stimulation to the patient 302. The generating and output of stimulation may be undertaken as part of one or more of the functions of "stimulation" indicated by the stimulation module 324 shown in FIG. 3. Variations of an implantable device that is configured to generate and output electrical stimulation signals are described in U.S. Pat. No. 6,690,974 to Archer et al. for "Stimulation Signal Generator for an Implantable Device", issued Feb. 10, 2004. U.S. Pat. No. 6,690,974 is incorporated by reference herein in the entirety.

In some embodiments, the stimulation generated and output by the implantable medical device 100 is intended to be a form of therapy to the patient. In other embodiments, the stimulation generated and output by the implantable medical device 100 is intended to evoke a response from the patient that can be sensed and/or logged and/or recorded and/or analyzed by any of the implantable medical device, the implantable medical device in combination with one or more external components, or by external components exclusively."

The neurostimulator may be configured to deliver the stimulation to one or more delivery devices or elements. In the block diagram of FIG. 3, one such delivery element is indicated by the label "stimulation element" 344. An example of a stimulation element 344 is an electrode configured to form part of a pathway for delivering electrical current through the patient. Another example of a stimulation element 344 is a device or collection of elements or mechanism configured to dispense controlled amounts of a neurochemical substance to the patient. As is the case with some possibilities for "active" sensing elements, a given stimulation element 344 may require power or one or more control signals in order to carry out its intended stimulation function.

When the implantable medical device 100 is configured to generate and output a form of stimulation, then the multiplexer module 314 may be configured to manage signals comprising or otherwise related to the form of stimulation to control delivery of the stimulation to the patient. For example, the multiplexer module 314 may manage current or voltage waveforms generated for stimulation or control signals that govern release of neurochemical substances.

Some possible forms of stimulation are described in more detail herein and include electrical stimulation as well as optical stimulation and stimulation in the form of the introduction of neurochemicals or drugs. The parameters that determine what stimulation is generated and how the stimulation will be output from the device are generally programmable and correspond to a set of stimulation parameters. FIG. 3 shows one possible destination for a stimulation output labeled as "stimulation element" 344. It will be appreciated that when the stimulation is, for example, pulsatile electrical stimulation, the stimulation element 344 may be an electrode or combination of electrodes forming a pathway through which current may flow in the patient. The electrode(s) may be on the distal end of one of the cortical strip lead 114 or the depth lead 116 that are described in connection with FIGS. 1 and 2A and 2B.

In some embodiments, the stimulation module 324 may be configured to deliver stimulation, at least some of the time, in response to the occurrence of a "detected event" or otherwise when the implantable medical device 100 identifies a particular characteristic in the physiological data acquired by the implantable medical device (e.g., as from one of the sensing elements 342, such as a drop in level of a neurotransmitter at the location of the sensing element). More particularly, the implantable medical device 100 may be configured to deliver stimulation, for example, in the form of a burst of electrical stimulation through one or more electrodes, whenever the device 100 determines that something it has been watching for in the acquired physiological data has in fact occurred. In these embodiments, multiple ones of the possible functional blocks of the implantable medical device 100 may be required to communicate with each other. For example, something that the detection module 318 detects may trigger the stimulation module 324 to generate and output stimulation, and the multiplexer 314 may select which of the available stimulation elements 344 are available through which to deliver the stimulation. The event counting/logging module 322 may store one or more values corresponding to the occurrence of the event or identified characteristic of the physiological data and the nature of the stimulation delivered in response to that occurrence, and whether the implant was able to deliver what it was programmed to deliver or something less than that. The recording module 320 may record what the sensing element(s) 340 sensed before, during and after the occurrence of the event or identified characteristic that resulted in the generation and output of the stimulation, and the event counting/logging module 322 and the control module 326 may store one or more data items that correspond to the fact that the event was detected or the characteristic was identified, including the date and time when the event was detected or the characteristic was identified. In other embodiments, the stimulation module 324 may be configured to deliver stimulation as a therapy at times that are not necessarily related to what the implantable medical device determines are events or identified characteristics, but rather according to a schedule or continuously or in reaction to some other behavior or command (e.g., a request by the patient or the patient's physician to deliver stimulation to the patient). In still other embodiments, the stimulation module 324 may be configurable to deliver stimulation not as a therapy but rather to evoke a response from the patient, for example, in assessing the effectiveness of a drug regimen or for a purpose of testing the neurostimulation, detection or other functions of the implantable medical device 100.

The implantable medical device 100 also is configurable to communicate unidirectionally or bidirectionally with one or more external components, for example, via a wireless communication link. For example, a selectable part-time wireless link to external components may be realized with inductive telemetry (short range or long range) using a telemetry coil or other transceiver part or antenna provided in the implantable medical device. Alternatively or additionally, communication between the implantable medical device 100 may be establish using magnet fields or interruptions in magnetic fields with a magnetic sensor (e.g., a reed switch or a GMR sensor) provided in the implantable medical device. Some of the external components may be considered "host" devices insofar as an external component can be used to control the implantable medical device 100, for instance, by transmitting new programmable parameters which parameters will govern the generation and output of electrical stimulation from the implantable medical device 100, or by causing data such as electrographic records stored in the implantable medical device to be uploaded to the external component. A "host device" may encompass functions carried out by both external and implantable components of a medical device system.

Embodiments of the systems and methods can include multiple ones of each possible type of external component or may be configured for communication with only a selected subset of all of the possible external components. For example, a given implantable medical device 100 may be configured for communication with any inductive wand, magnet, or physician's programmer but only one patient remote monitor, or with a set of physician programmers under the possession and control of physicians in a particular practice.

The operations and functions of the implantable medical device 100 are controlled, in whole or in part and most of the time or some of the time, by a control module 326 labeled as "control" in the block diagram of FIG. 3. The control module may include the functions of controlling the sensing, multiplexing, detection, event counting/logging, recording, and stimulation as well as managing use of power (e.g., from a primary cell or rechargeable battery) and communicating between the implant and one or more external components whenever the implant is called upon to do so. For example, the control module 326 may determine whether and when a given algorithm is executed to govern detection of events or other identification of characteristics in the acquired physiological data. Similarly, the control module 326 may determine whether and when a form of stimulation is to be generated and output by the stimulation module 324, if the neurostimulator 100 is configured to generate and output any stimulation for therapy, evoking responses, testing a system configuration, or otherwise.

The external components with which the implantable medical device 100 is configurable to communicate may include a programmer 362 which, once a communication link is established with the implantable medical device, may be used to manually control the operation of the neurostimulator as well as to transmit information to or receive information from the neurostimulator. For example, the programmer 362 can be used to choose values for and set parameters in the implantable medical device in order to adapt the function of the neurostimulator to meet the patient's needs. The programmer 362 also can be used to upload or receive data (including but not limited to whatever data have been stored on the neurostimulator relating to the acquired physiological data, the results of analyzing the physiological data, and one or more conditions of the neurostimulator at the time the sensed information is acquired). The programmer 362 further can be used to download or transmit program code or other information from the programmer to the implantable medical device, or to command the implantable medical device to perform specific actions or to change modes as desired by a physician operating the programmer. To facilitate these functions, the programmer 362 is adapted to receive input from a physician (e.g., from a touch screen or keyboard on a laptop or tablet computer) and to provide outputs to the physician (e.g., in the form of an interactive graphical user interface provided on a laptop or tablet computer).

The external components with which the implantable medical device 100 is configurable to communicate may also include a patient remote monitor 362 or other device intended to be reserved for use primarily by the patient in whom the implantable medical device is implanted or the patient's caregiver. The patient remote monitor 362 may be configured to allow the patient to establish communication with the implantable medical device in order to upload data from the implantable medical device to a network (e.g., via a telephone line or broadband communication scheme), where the data eventually may be stored in a database or maintained using a data management system 360.

The external components with which the implantable medical device 100 is configurable to communicate may also include an inductive wand 364 which may be necessary to establish the wireless communication link between the implantable medical device 100 and the programmer or remote monitor 362.

An external component may include or comprise a website interface element that enables a user of the website to access one or more data bases in which information obtained from or otherwise concerning the implantable medical device 100 is maintained. The website interface may include a graphical user interface for interaction between a physician-user or other user with the data base(s).

One or more external components with which the implantable medical device 100 can communicate or on which data from the implantable medical device can be stored may be used to display information to a user and, in some circumstances, allow a user to interact with the data in various ways. For example, the programmer or remote monitor 362 may have both a display and a graphical user interface with which a user can interact with data obtained from or about the implantable medical device, and the data management system 360 may be associated with one or more websites with which a user can interact with data obtained from or about the implantable medical device as well as with data obtained from or about other implantable medical devices or other data (e.g., data about patient populations).

In some embodiments, data manipulated by a user via a graphical user interface or the like may be saved locally and/or "posted" to one or more data bases of the data management system 360. In still other embodiments, a user may be able to use a graphical user interface to retrieve data from the data management system 360, such as data previously acquired from the same neurostimulator via external components, and display these data to a user and/or allow the user to manipulate these data.

A user may use one or more external components or an element or feature of an external component (such as an interactive website or an input screen), to associate with the patient data about one or more drug regimens to which the patient having the implanted neurostimulator 100 is subjected. For example, the physician may be prompted to input data on a display or a website page concerning the types of medication a patient is receiving, the dose of each medication, the time each dose is intended to be taken, and the level of medication the patient is intended to receive, for example, each day. Alternatively or additionally, the physician may be prompted to input data on a display or website page concerning changes made in drug regimens to which the patient is subjected, for example data concerning dose increase, dose decrease, addition of a medication, discontinuation of a medication, or change in dose scheduling.

Alternatively or additionally, the patient may be prompted to input data whenever he or she takes a medication. (This information could also be provided by a patient action such as opening the pill bottle or inverting the pill bottle or accessing the pill from some type of medication dispensing device.) The information input by the users may be stored on one or more external components, used in real time by external components while a communication link between the external component and the implantable medical device is established, or delivered to the implantable medical device for use by the neurostimulator in adjusting, for example, (1) the parameters that determine what characteristics the neurostimulator identifies in the physiological data it acquires or (2) the parameters that determine what form of stimulation is generated and output from the neurostimulator and (3) the parameters that determine under what conditions (e.g., when) the stimulation is output for delivery to the patient.

The data concerning a patient's drug regimen(s) may be used in algorithms executed in one or more external components, the implantable medical device, or some combination of these in assessing such things as whether a drug regimen is effective or well-tolerated by a patient and, if not, whether a parameter associated with a drug regimen (e.g., type of drug, class of drug, dose of drug, method of delivery of the drug, or timing of delivery of the drug) ought to be varied in an attempt to improve the therapeutic result for the patient. Alternatively or additionally, the data concerning the patient's drug regimen(s) may be used in calculations to assess such things as whether one or more parameters that control the functions of the implantable medical device should be adjusted in an effort to improve the patient's overall response to therapy (e.g., a therapy comprising a drug regimen and bursts of electrical stimulation (as are described in more detail below)), such as a reduction in the rate of clinically evident seizures in a patient who has epilepsy.

Referring now to FIGS. 4A and 4B, one example of a type of physiological data that may be acquired with the implantable medical device 100 is described. An electrographic signal 410 corresponds to a field potential measured at one electrode or a field potential difference measured between two or more electrodes (including at least one electrode that is configured as a sensing element 342 or a sensing/stimulation element 340) over a period of time. The electrographic signal 410 evidences a segment of pathological activity 420 which corresponds to activity that is characterized by a higher amplitude than the activity that precedes it in the preceding portion 422 of the electrographic signal 410.

For a given instance of the pathological activity 420, after a time the pathological activity may be defined as corresponding to an "event" which it is desirable to log as having been "detected" in the implantable medical device 100. For example, the detection module 318 of the implantable medical device may be programmed with a set of detection parameters that are meant to cause the implantable medical device to recognize the pathological activity 420 whenever it occurs to store the portion of the signal that evidences the pathological activity 420 in the recording module 320, and to store one or more data items in the event counting/logging module 322 whenever the pathological activity 420 occurs in the patient.

The pathological activity 420 may be defined, in part, in the implantable medical device 100 with an "event detected" marker 424 (which may correspond to a date and time at which a given occurrence of the pathological activity 420 is first recognized (or "detected") by the implantable medical device) and to an "end-of-event-detected" marker 426 (which may correspond to the time at which the given occurrence of the pathological activity 420 is no longer recognized (or no longer "detected") by the implantable medical device). The pathological activity 420 may be defined in part as a "duration-of-a-detected-event" 428 in terms of the time that elapses between the event detected marker 424 and the end-of-event detected marker 426.

It will be appreciated that, in some embodiments, the time at which the implantable medical device recognizes that a given instance of pathological activity 420 constitutes the beginning and ending of an event and, hence, the duration of the event 428, will depend in part on the rate at which the physiological data (here, the electrographic signal) is being sampled and/or processed.

FIG. 4B depicts another example of a signal acquired by the implantable medical device 100 corresponding to electrographic activity of a patient's brain. The pathological activity 420 is recognized and marked with an "event detected" marker 424 and an "end-of-event-detected marker" 426. A "duration-of-detected-event" 428 is defined as the elapsed time between the "event detected" marker 424 and the "end-of-event-detected" marker 426. In FIG. 4B, at some time during the "detected event", electrical stimulation is delivered to the patient. The period of time over which the electrical stimulation is delivered to the patient corresponds to the "stimulation delivered" time 430 shown on FIG. 4B.

Figure 5A:
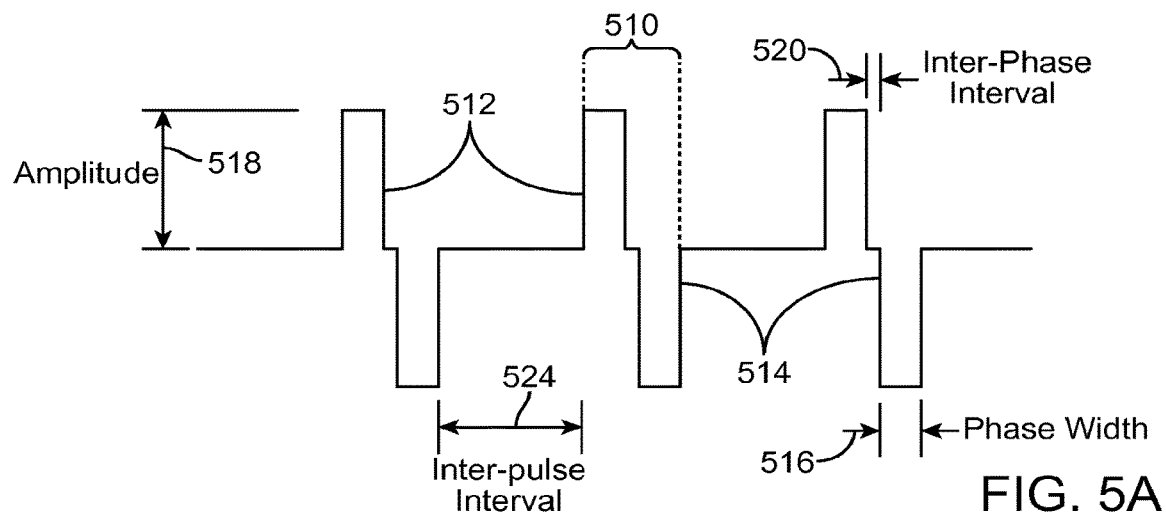
FIG. 5A is a diagram illustrating examples of the characteristics of an electrical stimulation therapy that may be generated and output according to embodiments.
Figure 5B:
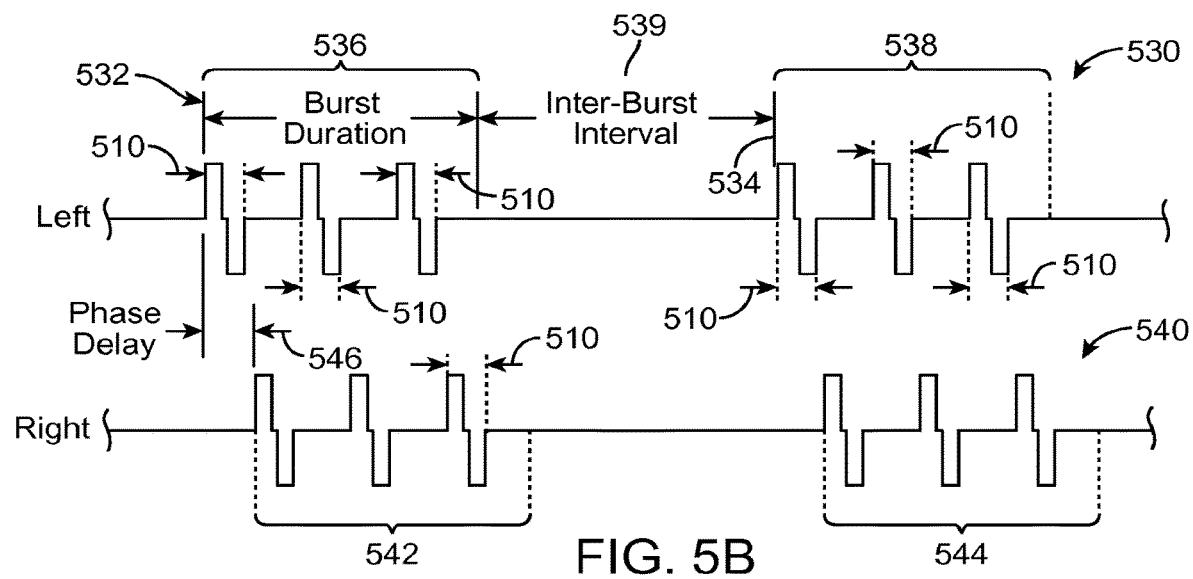
FIG. 5B is a further diagram illustrating examples of the characteristics of an electrical stimulation therapy that may be generated and output according to embodiments
Figure 5C:
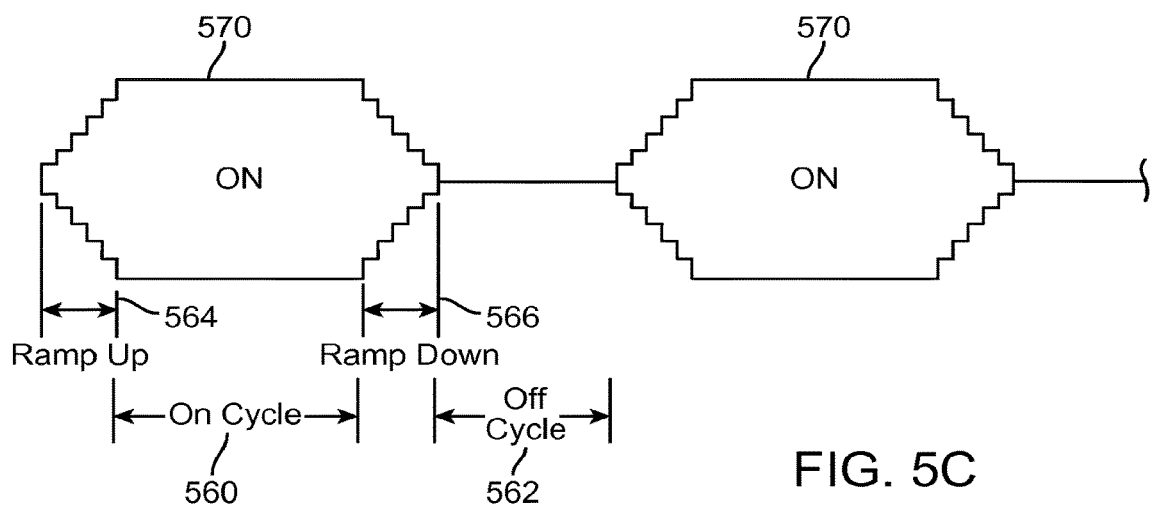
FIG. 5C is another diagram illustrating examples of the characteristics of an electrical stimulation therapy that may be generated and output according to embodiments.

Referring now to FIGS. 5A-5C, waveforms are illustrated that correspond to forms of electrical stimulation that may be delivered to a patient through one or more stimulation pathways including one or more stimulation elements 344 or sensing/stimulation elements 342. FIGS. 5A-5C relate to a pulsatile form of electrical stimulation. The stimulation may be generated by the implantable medical device 100 configured as a neurostimulator by various means, including, for example, using current-controlled or voltage-controlled stimulation pulses. In FIG. 5A, three stimulation pulses 510 are shown. Each stimulation pulse 510 is characterized by a leading phase 512 and a trailing phase 514. Each of the leading phase 512 and the trailing phase 514 is further characterized by a phase width 516. In the example shown in FIG. 5A, the leading phase 512 is positive-going and the trailing phase 514 is equal but opposite to the leading phase 514 and therefore is negative-going. The phase width 516 of each phase is the same.

Each phase is characterized by an amplitude 518. The amplitude 518 of each phase 510 may be measurable in volts (voltage), for example in a range from +/−0.05 V to +/−12 V, or amperes (current), for example in a range from +/−0.01 mA to 15 mA. If the amplitude of each of the leading phase 512 and the trailing phase 514 of a pulse 510 are the same, then the entire pulse 510 may be referred to simply as having that amplitude 518.

The leading phase 512 and the trailing phase 514 of a pulse 510 need not be symmetrical as shown in FIG. 5A, however, it typically is a design goal or criterion to keep the total charge delivered in the leading phase 512 of a pulse 510 roughly equal to the total charge delivered in the trailing phase 514 of the pulse in order to balance the charge at the interface between the stimulation element 344 (e.g., an electrode used to deliver stimulation) and the patient (e.g., the neural tissue at which the stimulation electrode is situated). Charge-balancing may be accomplished by manipulating the amplitude 518 and phase width 516 parameters of each pulse 510. For example, a pulse 510 may be provided with a leading phase 512 with the same amplitude 518 and phase width 516 as the amplitude and phase width that characterize the associated trailing phase, or different but balanced amplitudes and phase widths can be used for each of the leading phase 512 and trailing phase 514. Further, it may be desirable to limit the charge delivered per phase to 25 microcoulombs per square centimeter of stimulation element 344 surface area (e.g., electrode surface area when the stimulation element 344 is an electrode). Charge-balancing is believed to mitigate against the risk that any irreversible electrochemical reactions will occur due to a build up of charge at, for example, an electrode-to-tissue interface.

Typical values for the phase width 516 of a pulse 510 are selected from the range 40 to 1000 microseconds. However, longer phase widths 516 such as 0.5 sec, or waveforms that are not charge-balanced, can be used in applications such as electrical field stimulation or when stimulation is delivered from outside the scalp, where reversibility of electrochemical reactions is not essential or as much of a concern.

Each pulse 510 is further characterized by an inter-phase interval 520. The inter-phase interval 520 may be of zero duration, or may be of non-zero duration such as 100 microseconds which is believed to increase the likelihood that a pulse 510 will cause an action potential to occur in any given neuron.

A pulse 510 may be delivered singly, for example, for a given instance of an electrical stimulation therapy. Alternatively, a series of pulses 510 may be delivered in a repeating pattern that comprises a regular or irregular pattern. The duration elapsed between pulses is the inter-pulse interval 524; the inter-pulse interval 524 is inversely related to the frequency of stimulation. The frequency may, for example, be selected from the range 1 to 333 Hz. An instance of delivery of pulses 510, whether singly or in a series, or in one or more bursts (described below) or otherwise, may be described as delivery of a "stimulation waveform."

The pulse phase configurations (e.g., amplitude 518 and phase width 516), the inter-phase interval 520, and sometimes the inter-pulse interval 524 (the inverse of which corresponds to the frequency with which a set of pulses are being delivered) each may be referred to a "pulse parameter" or collectively as "pulse parameters."

Referring now to FIG. 5B, the top graph shows a stimulation waveform 530 comprising a first burst of electrical stimulation 532 and a second burst of electrical stimulation 534. The first burst 532 is identical to the second burst 534 in that each burst is comprised of three pulses 510. A burst of electrical stimulation 530 may be defined by one or more burst parameters, including, for example, the number of pulses 510 per burst (in this example, each burst 532, 534 has three pulses 510), and a burst duration 536, which may for example be selected from the range 0.1 sec to 10 minutes. As was the case with the pulses 510 described in connection with FIG. 5A, a given instance of a burst 530 may be delivered singly or in one or more sets. In the example shown in the top graph of FIG. 5B, the bursts are delivered in a set of two, namely, the first burst 532 is delivered and followed by the second burst 534. If, as here, a set of more than one burst is delivered as a stimulation waveform, then there may be an interval between each burst. More particularly, the inter-burst interval 539 defines the time that the neurostimulator will allow to elapse between bursts, which may for example be selected from the range 0.1 sec to 10 minutes.

It will be appreciated that in addition to delivering a single stimulation waveform, more than one stimulation waveforms can be delivered through different stimulation pathways (e.g., formed using more than one sensing/stimulation element 340 or stimulation element 344). In FIG. 5B, for example, the top waveform 530, which comprises a first burst 532 of three pulses 510 and a second burst 534 of three pulses 510 may be delivered to a stimulation element 344 or stimulation elements 344 located at a left side of the patient's brain. Simultaneously, a stimulation waveform 540, which is shown identical to the stimulation waveform 530 delivered to the left side of the patient's brain (but which may also be a different waveform) may be delivered to a right side of the patient's brain using one or more different stimulation elements 344 different from those that are used to deliver the left brain stimulation waveform 530. Optionally, and as in the case of the left brain stimulation waveform 530 and the right brain stimulation waveform 540 shown in FIG. 5B, delivery of the right brain stimulation waveform 540 may be delayed for a time after delivery of the left brain stimulation waveform 530 begins (or vice versa). Such a delivery delay is illustrated and denoted as a "phase delay" 546 between the top graph (left brain stimulation waveform 530) and the bottom graph (right brain stimulation waveform 540) of FIG. 5B. Thus, the parameters defining or relating to bursts may include the duration of a burst, the number of bursts in a set (or the number of bursts delivered in a given stimulation waveform) and the inter-burst interval.

It will be apparent that an implantable medical device 100 configured as a neurostimulator can be programmed to deliver one or more of the stimulation waveforms described here in response to "detected events" or other characteristics identified in physiological data acquired by the implantable medical device, such as acquired electrographic activity from the patient's brain. For example, the implantable medical device 100 may be configured to deliver one or more stimulation waveforms, comprising, for example, a burst 532 of pulses 510 in response to a detected event that represents an instance of an epileptic discharge (e.g., a period of abnormal neural firing characterized by properties such as increased synchrony between neurons) sensed at or near a location in the patient's brain where one or more sensing elements 342 or sensing/stimulation elements 344 have been situated. Alternatively or additionally, the implantable medical device 100 may be configured to deliver one or more stimulation waveforms to the patient continuously or according to a duty cycle (e.g., a duty cycle which dictates when stimulation waveforms may be delivered and when stimulation waveforms may not be delivered).

According to some embodiments, any or all of the parameters governing a given instance of a stimulation waveform such as the amplitude 518 pulse parameter or a burst duration 536 burst parameter can be configured to be programmable by a user (e.g., a physician using one of the external components, such as programmer 362) and/or adjustable by the control module 326 of the implantable medical device 100 and/or one or more of the external components (e.g., automatically by the implantable medical device, for instance, in a closed-loop feedback circuit implemented by the implantable medical device).

If the implantable medical device 100 generates and outputs electrical stimulation pulses 510 and/or bursts 532, 534 according to a duty cycle, the electrical stimulation may be defined in part by an "on" cycle 560, in which the neurostimulator is delivering one or more stimulation waveforms including at least one pulse 510 and an "off" cycle 562, in which the neurostimulator is not delivering any pulses 510.

The neurostimulator can be further configured so that a given stimulation waveform is characterized by pulses that start out being delivered at a first amplitude and then gradually increase in amplitude to a maximum amplitude. Similarly, a given stimulation waveform may be characterized by pulses that gradually decrease in amplitude towards the end of the period over which the stimulation waveform is delivered. The set of stimulation waveforms 570 shown in FIG. 5C illustrate both a "ramp up" 564 period for a burst or set of bursts 570 and a "ramp down" period 566 for a burst or set of bursts. The "ramp up" and/or "ramp down" periods may be beneficially applied when there is an actual or perceived risk that a less gradual increase or decrease in stimulation delivered to a patient will cause the patient to experience discomfort or other unpleasant or undesirable side effects of the stimulation.

While the stimulation waveforms described in reference to FIGS. 5A-5C are pulsatile stimulation waveforms, the implantable medical device 100 when configured as a neurostimulator may be programmed to generate and output other electrical stimulation waveforms such as sine waves (or digital approximations of sine waves) or near-DC stimulation, or square waves of relatively long durations. Some of these other forms of electrical stimulation waveforms are described in U.S. Pat. No. 6,690,974, previously incorporated by reference herein. Further, as mentioned elsewhere herein, a given instance of stimulation may take the form of some other signal that is intended to modulate the activity of neurons in the area of or included in a functional circuit at which one or more stimulation elements 344 (or sensing/stimulation elements 340) are located in the patient's central nervous system. Such other signal may comprise optical stimulation. Similarly, the form of stimulation may comprise delivery of a drug (or a signal generated and output by the implantable medical device that commands or otherwise results in delivery of a drug from, for example, an implanted or partially implanted drug delivery device).

Figure 6:
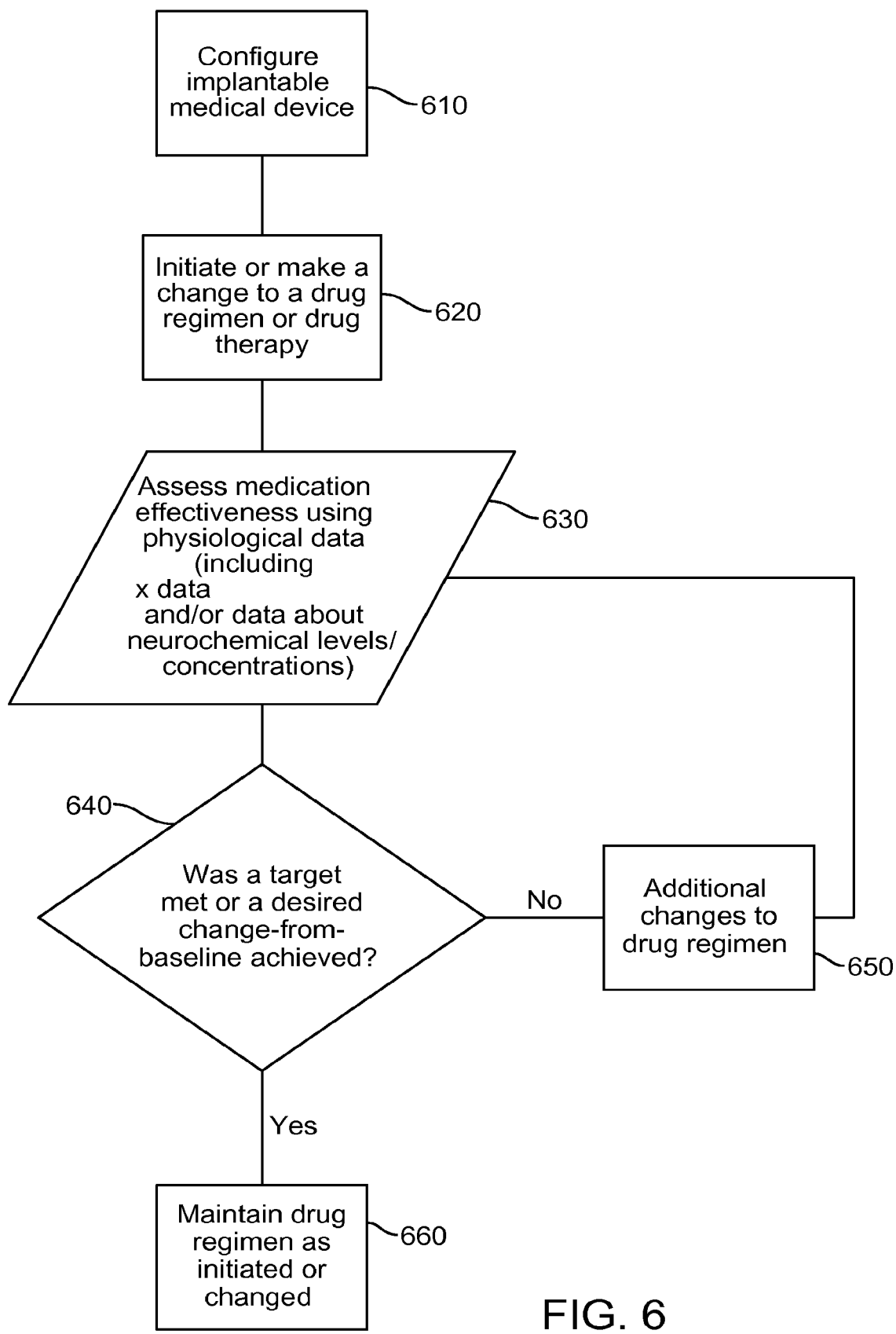
FIG. 6 is a flow chart corresponding to embodiments.

Referring now to FIG. 6, a system and method is described for using an implantable medical device 100 for assessing the effectiveness of an existing drug regimen to which a patient is subjected. Alternatively, the described system and method may be used for assessing a patient's response to a change to one or more parameters that define a particular drug regimen, so that a physician may assess whether the change tends to improve the effectiveness of the drug regimen insofar as concerns the neurological disorder the drug regimen is being used to treat. As mentioned elsewhere herein, parameters associated with a drug regimen may include which drugs a patient is receiving (or is intended to receive), a type of each drug (e.g., levetiracetam), a class of drug (e.g., generally, an "antiepileptic drug" (AED), or, more specifically, a "sodium-channel blocker"), the dose of drug (e.g., in milligrams), a method of delivery of the drug (e.g., in pill form for oral ingestion by the patient, or suspended in a liquid for fluid injection using a needle or an implanted, or partially implanted drug delivery device), or a timing for the delivery of the drug (e.g., twice a day, at certain times of the day (such as before bed), when a symptom of the disorder manifests, (e.g., the patient believes he or she is having a seizure or the patient experiences a symptom of a movement disorder (for instance, tremor)).

An implantable medical device 100 such as the implantable medical device and/or implantable neurostimulator 100 described with reference to FIGS. 1-5 herein, may be programmed by a physician to acquire physiological data from one or more sensing locations in a patient, and to process, analyze and evaluate the acquired physiological data in an effort to determine whether the acquired physiological data evidences what the implantable medical device 100 (e.g., via a detection module 318) is programmed to recognize as a "detected event" or another identified characteristic in the physiological data. An example of a "detected event" may correspond to a segment of an acquired electrographic signal for which the criteria associated with one or more analysis tools (such as a half-wave tool and/or a line length tool) have been satisfied and may include the segment of the signal itself as well as conditions of the device at the time the detected event occurred, such as an "event detected" time 424 and a "end-of-event-detected" time 426 and/or and a "duration-of-detected-event" 428. An example of an identified characteristic may be when the level (or concentration) of a neurotransmitter being sensed by a sensing element 342 falls below a certain threshold level or trends too low or the like.

If a user (e.g., a physician) has determined that a particular type of detected event or particular types of detected events or type of other identified characteristic can be correlated to whether a given drug regimen either is effective in achieving a desired therapeutic result or is well-tolerated by the patient, then the physician can configure the implantable medical device 100 to monitor a variable that reflects the correlation. For example, if the effectiveness of drug regimen is understood to be correlated to the number of times the electrographic activity sensed from certain locations in the patient's brain evidences seizure activity, and the implantable medical device 100 is configured to recognize such seizure activity and register it as a "detected event," then the number of detected events occurring in the signal(s) acquired by the implantable medical device 100 over a particular period of time (e.g., 24 hours), may provide a measure of how effective the drug regimen is for the particular patient. For example, if the count of detected events exceeds a certain threshold, the physician may infer or conclude that the drug regimen should be changed in some respect (e.g., by adding or removing a particular drug from the mix or changing the dosage of a drug, etc.) in order to improve the therapeutic effect of the drug regimen.

It will be appreciated that the count of detected events is just one example of a metric the implantable medical device 100 may be configured to track and/or store and/or record (for example, with the sensing module 312, the detection module 318, the event counting/logging module 322, and the recording module 320 each under the control of the control module 326), in order to facilitate an assessment of the effectiveness (or the patient's tolerance of) a drug regimen, either by a physician or by the implantable medical device 100 or an external component operating alone or in conjunction with the implantable medical device 100 and/or the physician. Other metrics may include duration of detected events, rate of detections over time, changes in power in specific frequency bands, pH shifts, tissue oxygenation, neurotransmitter levels, or evoked potential "EP" amplitude.

It will be appreciated that in some circumstances, it may be appropriate to configure the implantable medical device 100 to acquire and identify one or more baselines corresponding to a condition of the patient before starting the patient on a particular drug regimen or before changing one or more parameters of a drug regimen.

Referring again to FIG. 6, a physician may configure the implantable medical device 100 (e.g., an implantable medical device comprising a neurostimulator) (at the flow chart block 610) to acquire physiological data from one or more sensing elements 342 with which the implantable medical device is in operable communication, where the physiological data corresponds to electrographic activity or neurochemical levels indicative of the concentration of a medication or medications at or near a location of interest in the patient's neural tissue.

Examples of brain electrographic activity that may correlate to the concentration of a medication may include an electrographic pattern or waveform (e.g., spikes) that the physician has reason to believe constitute pathological activity or otherwise abnormal activity. For example, spikes occurring in a monitored electrographic signal may be understood to be associated with epileptiform activity (e.g., abnormal neural firing characterized by properties such as increased synchrony between neurons), clinical seizure activity, or electrographic seizures. Examples of neurochemical levels indicative of the concentration of a level of medication include a measurement acquired from a voltammetry sensor (such as configured for cyclic voltammetry). For example, since low levels of serotonin may be associated with major depressive disorder (MDD), low serotonin levels measured using cyclic voltammetry may be understood to be associated with MDD, and therefore serotonin levels measured using cyclic voltammetry may be understood to be associated with effectiveness of medications such as selective serotonin reuptake inhibitors that act by increasing serotonin levels in MDD.

After the implantable medical device 100 has been configured and, optionally, any relevant baselines have been measured and captured for later comparison to the information, and the implantable medical device 100 acquires, processes, and analyzes at block 620 of the flow chart of FIG. 6, the patient in whom the implantable medical device is implanted is subjected to a medication change. The medication change may involve, for example, starting the patient on a drug regimen or adjusting a parameter characterizing an existing drug regimen, such as adding a new drug, changing the dosage of a drug, maintaining the same total dosage but instructing the patient to ingest a pill more frequently or at different times of the day, or when the patient thinks he is experiencing a condition or symptom of the disorder for which he is being treated, etc.

Subsequent to the medication change, at block 630 of the flow chart of FIG. 6, an assessment of the effectiveness of the drug regimen following the medication change is undertaken. The assessment may be undertaken using physiological data obtained from the implantable medical device 100. The assessment may result in one or more of a display of data to a physician concerning the drug regimen, a recommendation to a physician concerning the drug regimen (such as to adjust or further adjust a parameter of the drug regimen), or an automatic adjustment of a parameter by the implantable medical device 100 that initiates a change to the drug regimen (e.g., by causing a drug to be delivered from an implanted drug delivery device (which may or may not comprise the implantable medical device 100 used in undertaking the assessment) and/or a change to another therapy to which the patient may be subjected (e.g., an electrical stimulation therapy delivered from the implantable medical device 100 or a different implantable medical device).

In some embodiments, the assessment of the effectiveness of the drug regimen following the medication change includes displaying to the physician on an external component a graphical or tabular representation of the rate of occurrence of each "detected event" the implantable medical device 100 is configured to recognize and track both after the medication change was made. The assessment further may include displaying to the physician a baseline rate of occurrence for each detected event to which the rate of occurrence after the medication change may be compared and contrasted, so as to, for example, inform the physician's determination of whether to change a parameter of the drug regimen or a parameter defining or controlling another form of stimulation intended to modulate the patient's neural activity. The assessment additionally or alternatively may include displaying to a physician a target rate of occurrence for each detected event which the physician also may use for comparison and contrasting purposes.

In some embodiments and as indicated by the block 640 in the flow chart of FIG. 6, after the medication change, the assessment of the effectiveness of the medication change may include determining whether a target has or has not been met, and if the target has not been met, initiating a further change to the medication as indicated by the block 650 in FIG. 6. If and when the target is met, a decision to maintain the current drug regimen may be made, as indicated by the block 660 in FIG. 6.

Embodiments of the method illustrated in the flow chart of FIG. 6 may be described with reference to the following example. Before a medication change is introduced to the patient, the implantable medical device 100 may be commanded to acquire and calculate a baseline rate of occurrence of spikes (for example, a count of how many spikes occur in an electrographic signal continuously monitored from the patient over a period of 24 hours). A "spike" may be defined for the implantable medical device 100 as a feature that occurs in a monitored electrographic signal sensed from a location in the patient's brain that is believed to be a focus for epileptiform or ictal or seizure activity. The implantable medical device 100 may be configured so that, for example, the detection module 318 will recognize a "spike" in the acquired physiological data whenever a segment of a signal being acquired is characterized by a certain amplitude for no more than a certain period of time. The implantable medical device 100 further may be configured to keep track of each time a spike occurs by storing and/or updating one or more data items in the event counting/logging module 322.

Merely for the purposes of illustrating this example, the baseline rate before the medication change may be 100 spikes per day. Alternatively, before a medication change is introduced to the patient, the physician may have selected a target rate for the number of spikes per day that represents a number of spikes per day that the physician would like not to be exceeded in the patient. For example, the physician's goal may be to keep the number of spikes the patient experiences per day below 100.

Before the medication change, the implantable medical device 100 may be configured to recognize as a "detected event" each occurrence of a spike and to keep track of the rate at which the spikes occur.

After the medication change, the implantable medical device 100 may determine that the number of spikes that occur in the first 24-hour period following the medication change is unchanged from the baseline or well below the not-to-exceed target of 100 spikes per day. These results may be uploaded from the implantable medical device 100 and displayed in a meaningful way that is also easy to understand, for example, on a display of a laptop computer (e.g., a programmer 362) or via a website that interfaces with the programmer 362 or with a data base such as a data base contained within a data management system 360. The results may be displayed to the physician together with the baseline data and/or the target rate so that the physician can readily appreciate whether a goal or goals of the drug regimen have been met (i.e., whether the drug regimen is seems to be effective, at least for the past 24-hour period).

Alternatively, after the medication change, the implantable medical device 100 may determine that the number of spikes that occur in the first 24-hour period is fewer than the number of spikes that occurred in the baseline. Or the post-medication rate of spike occurrence may be only slightly below the not-to-exceed target of 100 spikes per day. In either or both of these cases, the physician (or the implantable medical device 100 functioning autonomously and automatically) may further change a parameter of the drug regimen (e.g., increase a dose) and then re-assess whether that additional change further reduces the rate at which spikes occur in the patient in the next 24-hour period.

In other circumstances, after a medication change, the implantable medical device 100 may report that the rate of occurrence of spikes in the next 24-hour period either exceeds the rate of occurrence of spikes in the baseline period or exceeds the not-to-exceed rate associated with a target. In this case, the physician (or the implantable medical device 100) may also further change a parameter of the drug regimen and then re-assess whether that additional change improves the effectiveness of the drug regimen by bringing down the rate of occurrences of spikes.

A display over which the physician may view and appreciate the results of a given assessment of the effectiveness of a drug according to embodiments may include a feature such as a graphical user interface that allows the physician to initiate additional changes to the drug regimen. For example, upon comparing and contrasting the results of a metric obtained from the implantable medical device 100 following a medication change with a like metric in a baseline or associated with a target, the physician may decide to make a change to one or more of the parameters defining the patient's drug regimen and the graphical user interface may enable the physician to input the change.

Data about the patient's drug regimens and changes made thereto may be stored on one or more of the external components, such as the programmer 362 or in a database of the data management system 360, and/or on the implantable medical device 100 for later uses associated with treating the patient and other purposes related to patient care. In some embodiments, commands input to the programmer 362 to change a medication or some other parameter defining a drug regimen may be communicated to one or more drug-delivery devices implanted in the patient in order to effectuate the commanded change.

It will be appreciated that, based on the capabilities and features of the implantable medical device 100, the implantable medical device 100 may be configured to provide many different metrics that vary in type and kind that can be used beneficially with embodiments in order to assess the effectiveness of a given drug regimen. For example, in a patient being treated for epilepsy, a metric may be the rate of occurrence of one or more abnormal electrographic patterns of interest or waveforms of interest (such as a waveform other than a "spike"), where a given drug regimen would be deemed to be more effective when the rate of occurrence of such patterns or waveforms of interest decrease over time as compared to a baseline or target rate. For example, the abnormal electrographic pattern of interest may be an electrographic seizure that lasts at least five seconds, and a not-to-exceed target may be not to exceed 10 of these at-least-five-second seizures per day. Or the abnormal electrographic pattern of interest may be an electrographic seizure that lasts at least 90 seconds, and the target for the patient to experience no more than one seizure per week that lasts at least 90 seconds.

Put another way, at effective overall concentrations of medication, there should be fewer occurrences of detections of the abnormal electrographic patterns and waveforms by the implantable medical device 100 and there also should be fewer occurrences of seizure activity that the patient recognizes or notices. (In epilepsy, intracranial sensing electrodes may sense epileptiform activity from the brain, for example, even while the patient does not appreciate that he or she is having a seizure: there is a distinction between electrographic seizures and epileptiform activity, on the one hand, and "clinical seizures" on the other. In other words, a patient may experience an electrographic seizure without also experiencing a clinical seizure and the patient may not appreciate that the electrographic seizure is occurring.) It is noted that seizures that the patient recognizes or notices are often relatively rare, such as one per week, and the rate and incidence of these seizures is often highly variable over time. Further, reporting of such seizures by patients is often erroneous or missing. This means that estimates of the effectiveness of medication based only on the reduction of clinically or visibly observable symptoms, such as seizures that the patient recognizes or notices, are often highly uncertain. An advantage of the embodiments is that measurements, such as counts of detected events determined by an implanted medical device, can be taken more frequently than seizures naturally occur which are recognizable by a patient and/or a patient's caregiver or physician, and therefore the embodiments can provide more sensitive and specific information related to effectiveness of a medication than may be obtained from recognizable seizures.

On the other hand, if a drug regimen is not effective, either no change or an undesirable change in the rate of occurrence of the abnormal patterns or waveforms of interest would be expected (e.g., as compared to a baseline or target rate).

In some embodiments, additional changes to a drug regimen (e.g., additional medication changes corresponding to block 650 of FIG. 6) are informed by further analysis of the physiological data (e.g., neurochemical measurements) initially acquired in the assessing step corresponding to block 630 of FIG. 6. In the case where the rate at which some predetermined "event" is recognized as a "detected event" in the course of one of these assessments, if there is no change in the rate of occurrences of the detected event over time (for example over a day or a week), then a physician may assume that the concentrations of the medication are remaining stable at one or more locations of interest in the neural tissue that correspond in some way to the location(s) from which the physiological data is sensed. Thus, the physician may conclude that the drug regimen (e.g., a particular type of medication) is not effective at controlling the symptoms of the disease. The physician can then choose, for instance, to increase the dosage of a medication, discontinue a medication, or add a medication in an effort to reach a target (or cause a change from a baseline).

However, if there are changes in a rate of occurrence of a detected event over hours of a day or days of a week, then the physician may determine that the concentration of a medication at a location(s) of interest in the patient's neural tissue is varying. Variable levels could be caused, for example, by patient's failure to "comply" with instructions about how much and when to take a particular drug; the patient's taking other medications that interact with the medication(s) in the drug regimen; the patient's changing a pattern of behavior such as regarding exercise or sleep; and changes in hormones such as might occur during a patient's menstrual cycle. When the physician determines that an issue affecting the effectiveness of a drug regimen is the patient's compliance with a prescribed drug regimen or the patient's other behavior, the physician can counsel the patient to comply, or can select a medication with less stringent dosage requirements, in an effort to, for example, come closer to a target as is tested in step 640 of the flow chart of FIG. 6.

In some embodiments, distinctions can be made between changes in a measured value (such as a rate of occurrence of a detected event) that are indicative of the effectiveness of medication and changes in the measured value that are not indicative of effectiveness and instead are indicative of physiological variation that is random, substantially random, or otherwise not reflective of the effectiveness of medication. If changes in a measured value correspond in time to changes in medication dosage, or correlate to medication dosage or changes in medication dosage, then the physician may determine that the changes observed are genuinely due to changes in the effectiveness of a medication. In these circumstances, if the changes in the particular measured value are not associated in time with a medication change, then the physician may determine that the changes observed are not related to effectiveness.

In some embodiments, a system including an implantable medical device 100 can determine and indicate to the physician whether changes in a measured value are related to effectiveness using information related to medications and dosage, including time and/or date of any changes in medications or dosage entered into a user interface by the physician or patient. In other embodiments, a system including an implantable medical device 100 can estimate short-term variation in a measured value, such as by calculating the standard deviation of a set of measured values collected over a 24-hour period at one-hour intervals, and can indicate to the physician the proportional relationship between changes in the measured value that occur at longer intervals (such as 28-day intervals) when medication dosage was changed, and the short-term variation. In still further embodiments, a system or method can indicate to the physician that changes in a measured value that occur at intervals associated with dosage changes and are, e.g., greater than two standard deviations calculated as described above are indicative of effectiveness of medication, whereas changes in a measured value that are smaller than two standard deviations may not be relevant to effectiveness of medication.

Further, if the effectiveness of a given drug regimen seems to vary over months based on the information provided or otherwise generated by the implantable medical device 100, then the physician may determine that there are longer term changes in concentration of one or more of the medications such as might occur with changes in renal or liver function or with changes in weight, or that a medication is losing its effectiveness over time. In these situations, the physician may choose for instance to increase the dose of a medication in an effort to restore its effectiveness or to switch the patient to a medication that is expected to be less sensitive to liver or renal function.

In some embodiments, such as when a patient is being subjected to a drug regimen to treat epilepsy, changes in physiological data that correlate well to whether a drug regimen is effective may include changes that may be measured by any of the following metrics: decreases in the number of detected abnormal electrographic events; decreases in rate of occurrences of conditions of the implantable medical device 100 caused by abnormal electrical activity of interest, such as a decrease in the how often amplifiers in the device are saturated; decreases in the duration of a given "detected event"; decreases in the number of shifts in pH of extracellular fluid; decreases in the number of tissue spikes in oxygenation of tissue (such as tissue comprising the brain parenchyma); decreases in the excitatory neurotransmitters such as glutamate; or increases in inhibitory neurotransmitters such as gamma amino butyric acid (GABA).

In embodiments in which an implantable medical device is configured to monitor decreases or increases in neurotransmitters, these decreases or increases can be measured using voltammetry. Voltammetry is a family of analytic methods in which the voltage of a working electrode is manipulated with respect to a reference electrode, and the resulting current flow is measured. The characteristics of this current flow, such as small changes in the shape or amplitude of current when plotted against voltage, are indicative of the electroactive species present (in other words, the chemical species present that participate in electrochemical reactions) and their concentrations. Decreases or increases in neurotransmitters, such as glutamate or GABA, can also be measured using fixed potential amperometry at enzyme-linked biosensors, in which current flow through a sensor is modified by biochemical reactions that occur in the presence of neurotransmitters, and where this current flow is indicative of the amount of the neurotransmitter present in the surrounding solution. In embodiments in which an implantable medical device 100 is configured to measure shifts in pH of extracellular fluids caused by changes in neural activity, such shifts can be measured by pH electrodes such as ion-sensitive field effect transistors (ISFETs) sensitive to hydrogen ions, or by using voltammetric techniques as described above, for instance, with pH-sensitive wire electrodes such as metal oxide electrodes.

If embodiments reveal to a physician that a change to a drug regimen should be tested, then the physician can instruct the patient to continue to perform adjustments of the medication dosage to achieve further improvement or to maintain the current medication regimen without bringing the patient into the office. If no improvement in the physiological data (e.g., desirable changes in the levels of a neurochemical) occur at a dose that would be expected to be effective or at a dose that is eliciting side effects, the physician can instruct the patient to discontinue the medication. This may be desirable to minimizing side effects a patient experiences due to a given drug, or minimize the costs associated with a given drug (e.g., reduced dosage, lower cost). It will be apparent that having a quantitative assessment of the effectiveness of a drug regimen may be of great benefit to a physician in making the decisions about the drug regimen (such as whether to continue or discontinue a particular medication included within the drug regimen).

In sum, embodiments of the method described in the flow chart of FIG. 6 may provide one or more of the following advantageous results: First, the effectiveness of a patient's drug regimen may be monitored by a physician at least in part, based on information the physician has about the drug regimen the physician put the patient on as well as information which the implantable medical device is configured to produce and, for example, transmit to the physician when the patient uses an external component, such as a patient remote monitor 362 to transmit information from the implantable medical device 100 to the physician's programmer 362 or to a database in the data management system 360 which the physician can access, for example, via a website interface. This may result in fewer face-to-face visits between the patient and physician for the purpose of titrating or calibrating the patient's drug regimen. Second, a physician can use the data produced or generated by the implantable medical device 100 during the assessment as an indicator of whether the patient is likely complying with the drug regimen the physician has prescribed. Third, the physiological data operated on by the implantable medical device 100 (and one or more metrics associated therewith or derived therefrom) may provide an objective measure of effectiveness of a given drug regimen. This may be important when the patient is being treated for epilepsy, for example, since the effectiveness of a drug regimen otherwise is determined, at least in part, by the number of seizures the patient recognizes that he or she is having. More particularly, epilepsy patients are typically asked to maintain some sort of a log (commonly referred to as a "seizure diary") in which the patient records the dates and times the patient thinks they are experiencing a seizure. (Since a given electrographic seizure may not be perceived by a patient as a seizure, in the best case, the patient's seizure diary will only represent a record of the patient's "clinical seizures" (or the seizures for which there are clinically-observable symptoms). In other than the best case, the patient may underreport his or her clinical seizures in his or her seizure diary, for example, because the patient may not remember a seizure or may remember a seizure but forget to make an entry in his or her seizure diary. Thus, for several reasons, a patient's reported seizures in a seizure diary often is a subjective record of seizures and often not a very reliable one at that. Fourth, the physiological changes (including but not limited to neurochemical changes) produced by the medications and observed and tracked by the implantable medical device 100 often may precede reported changes in clinical symptoms. Fifth, a physician may assess whether a lower dose (including no dose) of a particular drug may be equally effective for the patient given the relevant baseline or target, and the lower dose may be better tolerated by the particular patient (e.g., in terms of toxicity or unpleasant side effects). Finally, determining whether a medication is ineffective can be accomplished quickly and objectively.

Figure 7:
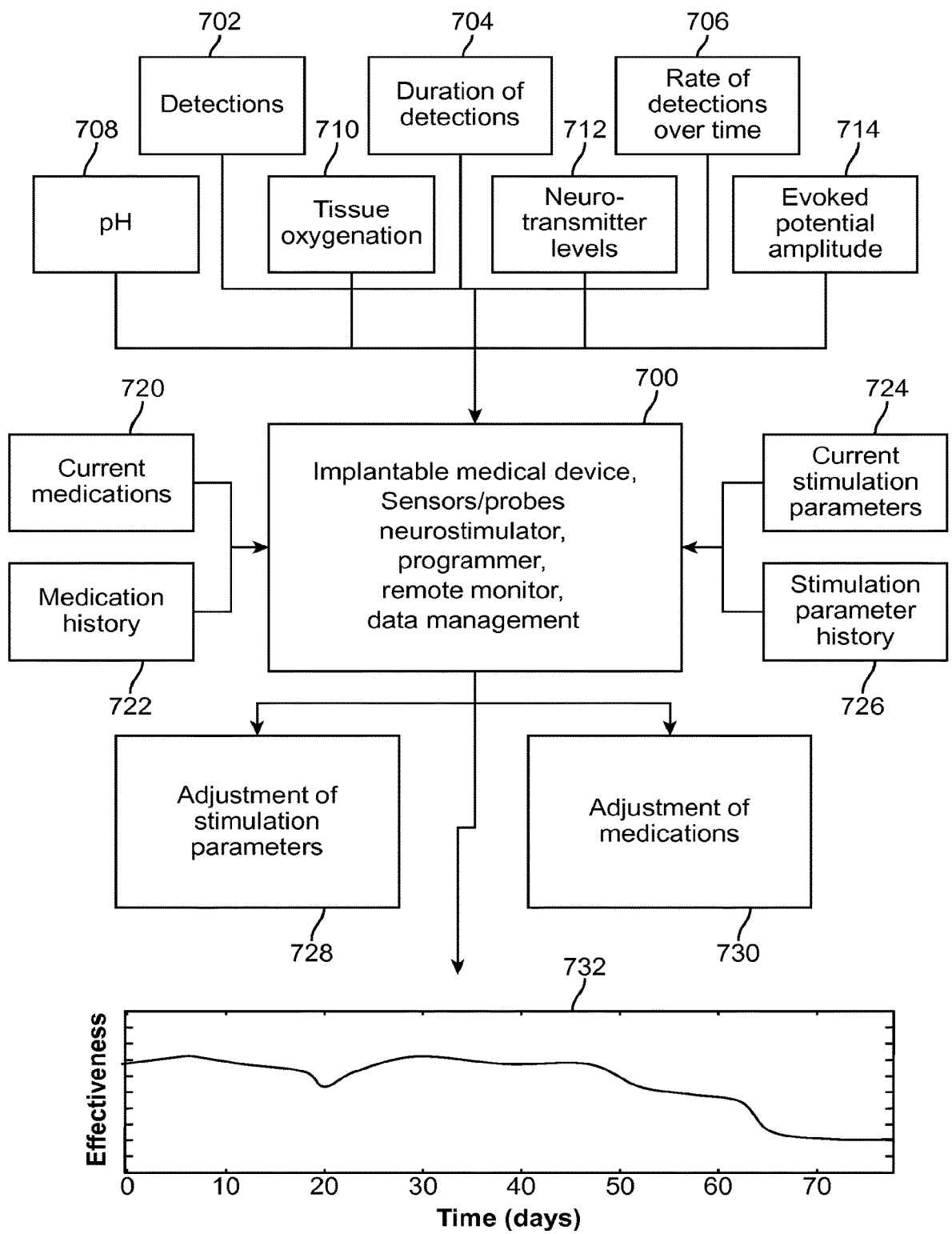
FIG. 7 is a schematic illustrating a system according to some embodiments.

FIG. 7 is a schematic illustration of a system according to embodiments generally in the form of a block diagram, for assessing the effectiveness of and/or adjusting a parameter of a drug regimen or other drug therapy to which a patient is subjected for treatment of a neurological disorder.

A center block 700 in FIG. 7 represents a collection of components described previously including an implantable medical device 100, sensors/probes associated with the implantable medical device (e.g., electrode-bearing brain leads 114, 116, a probe configured to acquire voltammetry measurements, a probe configured to obtain an oxygen concentration measurement, etc.), external components with which the implantable medical device 100 may communicate, such as one or more programmers 362, a patient remote monitor 362, and a data management system 360 or a website interface and/or a database or set of databases thereof.

The inputs to the components represented by the center block 700 may include one or more of information corresponding to "detected events" in neural activity (e.g., electrographic activity) that is defined as constituting pathological activity (or other identified characteristics of physiological data) 702, duration of detected events (or other identified characteristics of physiological data) 704; rate of occurrences of detected events (or other identified characteristics of physiological data) over time 706, pH 708; tissue oxygenation 710; neurotransmitter levels 712; or amplitude of evoked potentials 714 (which evoked potentials are described in more detail below).

In addition to the system inputs (or potential system inputs) 702, 704, 706, 708, 710, 712, and 714, other data may be used in embodiments in assessing the effectiveness of a drug regimen, including data corresponding to the medications a patient may be currently taking ("current medications" 720), and data corresponding to a historical perspective of the medications or drug regimens to which the patient has been subjected (e.g., over a long term or a relatively short term) ("medication history") 722.

Where a patient is implanted with a medical device that is configurable to deliver or which has been delivering a form of stimulation to the patient (for example, a form of electrical stimulation therapy), still other data may be used in embodiments in assessing the effectiveness of a drug regimen, including data relating to the set of stimulation parameters according to which stimulation waveforms are generated and output from the implantable neurostimulator and to which location(s) in the patient's neural system the stimulation is delivered (e.g., to which electrodes on which brain leads 114, 116) ("current stimulation parameters" 724). It will be appreciated that if the form of stimulation is being delivered to a patient using other than an implanted neurostimulator (e.g., by introducing optical stimulation to the brain through a probe that is only partially implanted in the brain), then values for current stimulation parameters 724 may also exist.

Where a patient has an implanted neurostimulator (or otherwise has been receiving a form of neurostimulation, as from an optical stimulation source), there may exist a history of that previously delivered stimulation as may be defined, for example, by a set of stimulation parameters. Such "stimulation parameter history" information 726 also may be used in embodiments to assess whether a drug regimen is effective.

One or more outputs corresponding to the components represented in the center block 700 may be useful in adjusting either the parameters of a drug regimen or, if applicable, the parameters of another form of therapy the patient may receive, such as a form of electrical stimulation therapy, in response to a given assessment of the effectiveness of a drug regimen. For example, the effectiveness of a given drug therapy may be improved by either or both of adjusting a parameter of the drug therapy and adjusting a parameter of an electrical stimulation therapy. More specifically, it may be the case that the effectiveness of a drug therapy may be improved, not by increasing the dose of a drug, but rather by adding a form of electrical stimulation (or adjusting a parameter of an electrical stimulation therapy currently being delivered) so that the electrical stimulation is directed to one or more locations of interest in the neural tissue (e.g., at the location of a stimulating element 344). Conversely, the effectiveness of a given electrical stimulation therapy may be improved not by increasing the amplitude or pulse width with which the stimulation is characterized, but rather by adding a medication or otherwise adjusting a parameter of a drug regimen.

In some embodiments, an overall effectiveness value for a given therapy or combination of therapies intended to modulate behavior of a patient's neural system using a combination of the system inputs 702, 704, 706, 708, 710, 712, 716, the patient's drug regimen 720 and drug regimen history 722, device-specific data such as the current stimulation parameter 724 and the historical stimulation parameters 726. Such an overall effectiveness value may be displayed numerically or presented graphically. For example, in the plot 732 shown at the bottom of FIG. 7, the rate at which an overall effectiveness value changes over time (in units of days) is graphed for a user.

In one embodiment, an overall effectiveness value for a given neuromodulation therapy (e.g., comprising a drug therapy and an electrical stimulation therapy) may be calculated using a combination of the data and by multiplying the number of electrographic seizures detected per week by the implantable medical device 100 by the average duration of the electrographic seizures. This calculation yields a value that is descriptive of the total time per week spent in an electrographic seizure, and it will be apparent that relatively low values such as one minute per week may be associated with effectiveness of a given neuromodulation therapy whereas relatively high values such as 1000 minutes per week may be associated with lack of effectiveness of the therapy.

The value yielded by this calculation may be compared to a not-to-exceed target such as not to exceed five total minutes per week of electrographic seizure (which are defined for the implantable medical device to comprise "detected events"). This information can then be used by a physician with knowledge of the patient's current drug regimen 720, medication history 722, and, optionally, stimulation parameters 724 and stimulation parameter history 726 (if the neurostimulator is configured to deliver stimulation) to adjust medication types and levels, for example, in accordance with the flowchart of FIG. 6.

It will be apparent that several elements in the flow chart of FIG. 6 can be a physician or the implantable medical device 100 or a combination thereof. For instance, a physician can determine an appropriate medication change guided by an overall effectiveness value calculated and displayed by one or more of the components in the center block 700 of FIG. 7 (e.g., an implantable medical device 100 and an external programmer component 362). In an alternate embodiment, the system may enable the implantable medical device 100 (if the implantable medical device is provided with information related to the patient's current medications 720 and medication history 722) to automatically suggest an appropriate adjustment of medications 730 guided by this same effectiveness value. In a further embodiment, an implantable medical device configured to deliver neurostimulation 100, if the implantable medical device is provided with information related to current stimulation parameters 724 and stimulation parameter history 726, can automatically suggest an adjustment of stimulation parameters 728 that is guided by the system inputs 702, 704, 706, 708, 710, 712, and 714 as well as by the physiological data itself (e.g., stored electrographic signals or representations thereof) and that is appropriate given the current medications 720.

Figure 8:
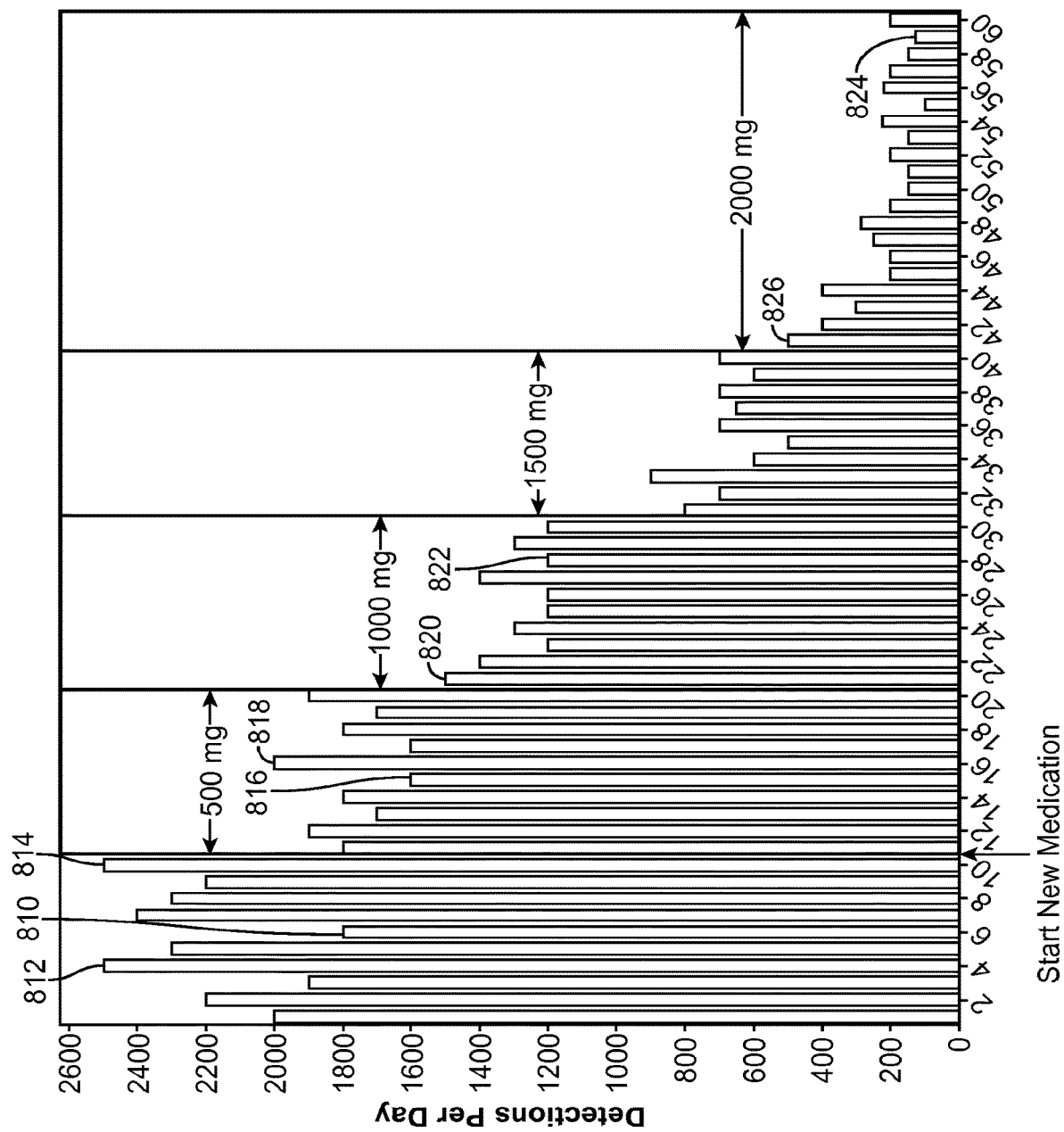
FIG. 8 is a graphical representation illustrating an assessment of the effectiveness of a drug regimen according to embodiments.

FIG. 8 is a histogram showing, on the y-axis (or vertical axis) a number of "detections per day" and, on the x-axis (or horizontal axis) the passage of time in days. The metric that results in the "detections per day" may be one of a great many possible metrics, such as a number of electrographic seizures detected per day, a number of electrographic seizure precursors detected per day, a number of spikes detected per day, the number of times the concentration of a neurotransmitter rose above a certain threshold, the number of times the oxygen or pH level fell below a certain threshold, and so on and so forth. In short, the "detections per day" can correspond to the rate at which something occurs that the implantable medical device 100 is configured to detect or otherwise identify. For ease of description, the "detections per day" represented in FIG. 8 may result from the implantable medical device 100 being programmed (according to its set of detection parameters) to continuously log in the event counting/logging module 322 when a particular type of epileptiform "event" is "detected", to calculate a rate of detection of the logged events over each successive 24-hour period, and then to log the average number of events detected per day. The average number of events detected per day by the implantable medical device 100 thus may result in the "detections per day" for a patient shown in FIG. 8. These data may be uploaded from the implantable medical device 100 to a host device, such as one of the external components (e.g., the programmer or patient remote monitor 362 or the data management system 360). The physician may monitor the "detections per day" at a location remote from the patient by viewing the data uploaded from the patient's implanted device and accessible from one or more of the external components.

FIG. 8 is meant to show that the number of "detections per day" varies as the dose of a particular drug being administered to the patient varies. For example, for the first 10 days, the graph shows the number of "detections per day" by the implantable medical device varies between about 1800 detections per day (e.g. the "detections per day" at Day 6 810) and 2500 detections per day (e.g., the "detections per day" at Days 4 812 and at Day 10 814).

At the 10-day mark, the physician instructs the patient to start taking a new medication at a daily dose of 500 mg. The drug might be an antiepileptic medication such as levetiracetam. After the patient begins taking the 500 mg dose of the new medication and over the next ten days, the "detections per day" decrease to vary from between about 1600 detections per day (e.g., "detections per day" at Day 15 816) to about 2000 detections per day (e.g., "detections per day" at Day 17 818). From this data the physician may infer that the 500 mg dose is effective in reducing the "detections per day."

Assuming that reducing the "detections per day" is one of the physician's objectives and the patient is experiencing no adverse effects from the drug, the physician may choose to try increasing the dose, to see if in so doing the "detections per day" are further reduced. In this circumstance, the histogram of FIG. 8 shows that, when the patient's dose of the same drug is increased from 500 mg to 1000 mg per day, the "detections per day" further decrease to vary between from about 1200 detections per day (e.g., "detections per day" at Day 28) to about 1500 detections per day (e.g., "detections per day" at Day 21 820).

FIG. 8 further shows that the number of "detections per day" continues to be reduced as the dosage of the drug is increased, such that at a daily dose of 2000 mg, the "detections per day" vary between from about less than 100 detections per day (e.g., "detections per day" at Day 42 824) to about 500 detections per day (e.g., "detections per day" at Day 41 826). Thus, the physician can see that the "detections per day" continues to decrease as the physician titrates the dose from an initial dose of 500 mg through intermediate doses of 1000 and 1500 mg up to 2000 mg. Monitoring the "detections per day" using the implantable medical device allows the physician to assess which dose of the drug is most effective up to some predetermined maximum (e.g., the maximum dose for the drug for this particular patient may be 2000 mg per day). The data obtained from the implantable medical device 100 may be of substantial value clinically because seizures (clinical or electrographic) will not always occur when the patient is present with the physician in the physician's office and because relying only on the patient's seizure diary alone as a measure of seizures is not especially reliable (due to patients underreporting or misreporting seizures). A physician may assess whether a particular dose of a drug is effective in treating a disorder of a patient more quickly and less ambiguously than if the physician were to rely only on patient-reported seizures or seizures otherwise observed or recorded in a clinical setting to assess effectiveness.

Figure 9:
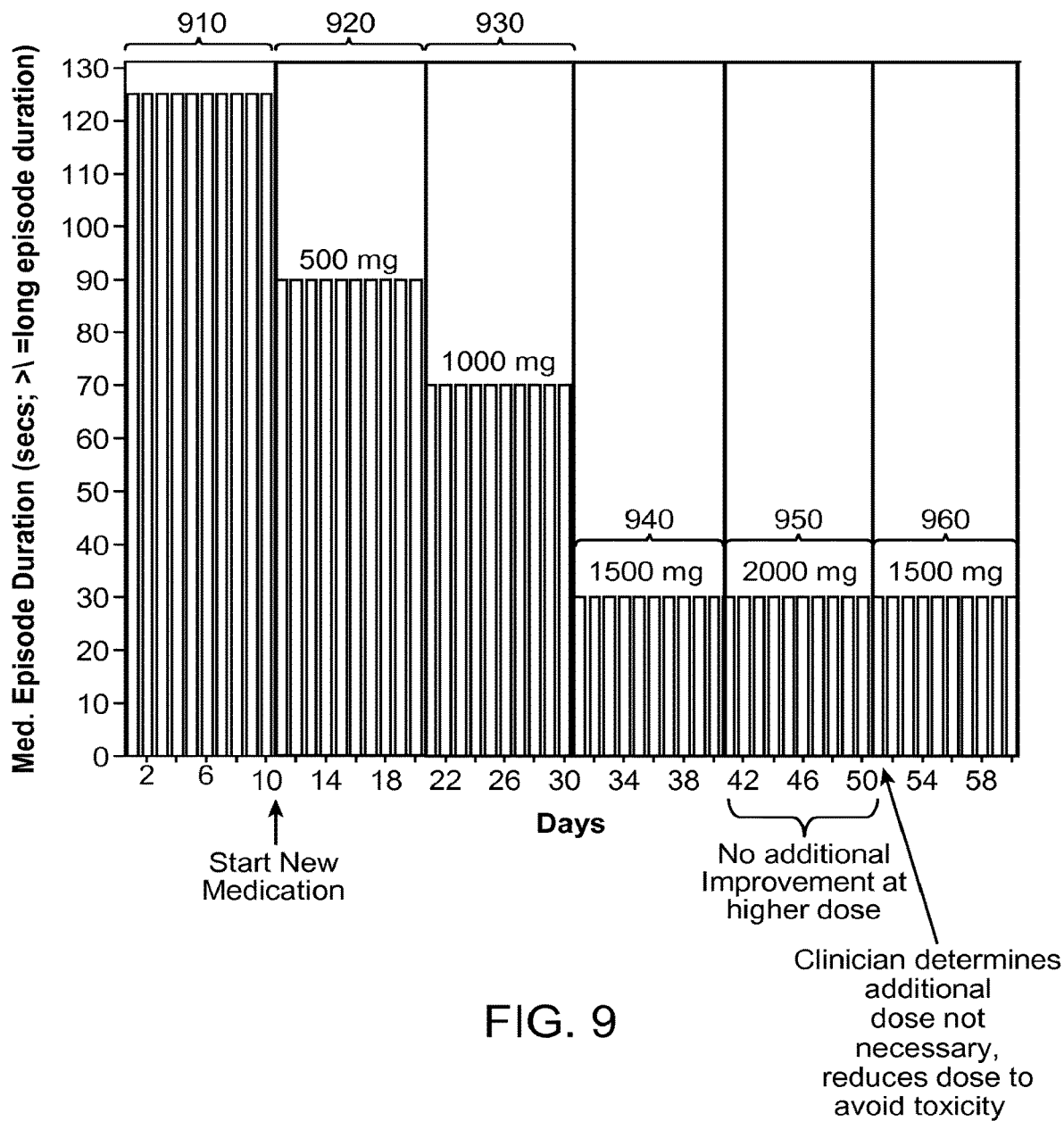
FIG. 9 is a graphical representation illustrating another assessment of the effectiveness of a drug regimen according to embodiments.

In another circumstance, and referring now to FIG. 9, a histogram similar to that shown in FIG. 8 is used to illustrate that embodiments can be used to assess when further changes in a patient's drug regimen have no incremental beneficial effect such that, for example, the dose of a drug should not be increased beyond a certain level. In FIG. 9, on the y-axis (or vertical axis) the medium duration of a long episode (in seconds) is plotted versus time in days on the x-axis (or horizontal axis) the passage of time in days. A "long episode" may be defined for the implantable medical device 100 by its programmable detection parameters as a type of pathological electrographic activity that persists (e.g., continues to be detected when sampled) over at least some minimum period of time, such as at least one second. For example, the implantable medical device 100 may be configured to recognize and therefore "detect" a long episode whenever an amplifier in the sensing module 312 is saturated at least once as a result of the input signal. The data logged by the implantable medical device 100 may be uploaded from the device to one or more host devices, such as the external components comprising the programmer or the patient remote monitor 362 and/or the data management system 360. During a patient's visit to the physician's clinic, the physician may retrieve data relevant to the "long episodes" detected by the implantable medical device 100 from a storage location such as in a database of the data management system 360 for review.

For the first 10 days, the patient is either on a drug regimen that is not effective in reducing the duration of long episodes or is not receiving any drug therapy at all. During this first 10 days, the data from the implantable medical device suggests that the patient is experiencing long episodes of at least 125 seconds each day (e.g., the long episodes of at least 125 seconds at Days 1-10 910). At the 10-day mark, the physician may introduce a new antiepileptic drug to the patient, such as valproate, starting the patient at a dose of 500 mg.

Upon introducing the new drug to the patient at the 500 mg dose, the long episodes appear to decrease from an average of at least 125 seconds to an average of 90 seconds (e.g., for Days 11-20 920). A shorter duration of a long episode may be correlated to less pathological activity occurring in the patient's brain and therefore reducing the length of the long episodes may be an objective of therapy for the patient.

The drug appears to be having a desirable effect on the duration of the long episodes up to a dose of 1500 mg (i.e., at an intermediate dose of 1000 mg, the median duration of a long episode shortens to about 70 seconds (for Days 21-30 930) from the 90 seconds observed during Days 11-20 920. After the dose is increased to 1500 mg, the median duration of a long episode drops to about 30 seconds and stays at that duration for about 12 days (for Days 30-42 940). However, when the dose is increased to 2000 mg over the next eight days, the median duration of a long episode remains steady at 30 seconds (for Days 42-51 950). So the physician drops the dose back down to 1500 mg (at Days 51-60 960) where the median duration of the long episodes the patient experiences remains stable at about 30 seconds. Thus, embodiments for assessing the effectiveness of a drug can be used to avoid having the patient habitually receive a dose of the drug that is higher than the dose which is effective for providing the desired therapy.

Figure 10:
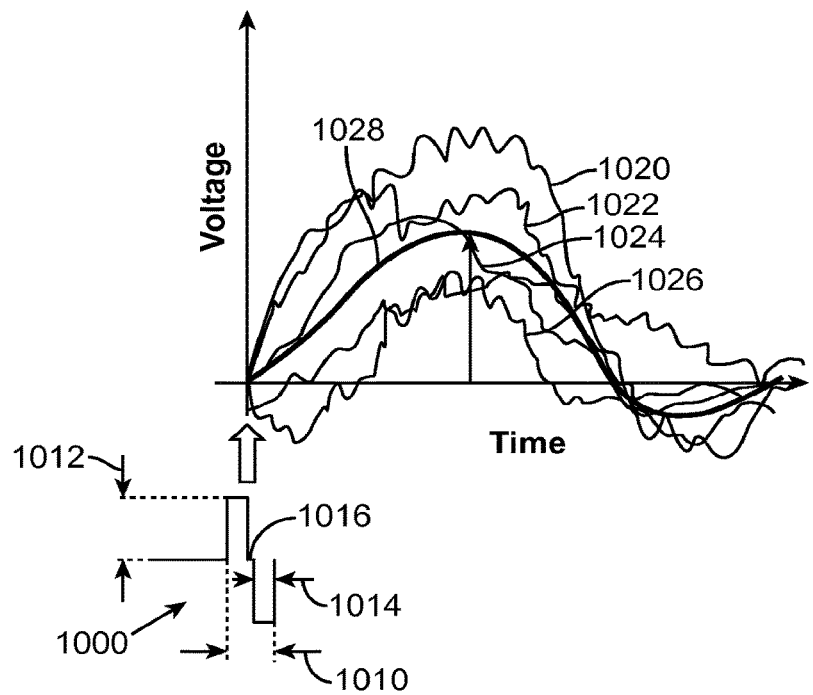
FIG. 10 is a graphical representation of evoked responses.
Figure 11:
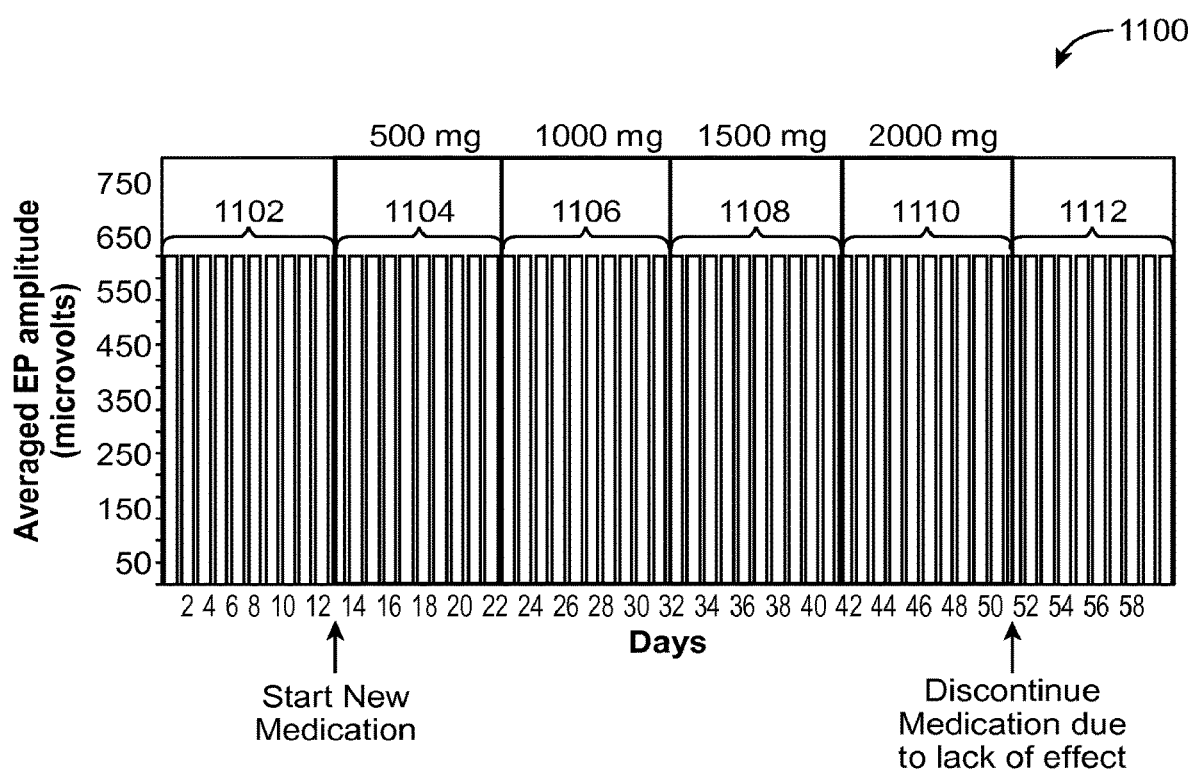
FIG. 11 is a graphical representation illustrating an assessment of the effectiveness of a drug regimen according to embodiments.

Referring now to FIGS. 10 and 11, embodiments are described wherein the effectiveness of a drug regimen is assessed relative to one or more evoked potentials. In these embodiments, an implantable medical device 100 is configured to acquire, process, and analyze electrographic signals sensed from a patient, and to identify one or more features in the electrographic signals (e.g., an amplitude for each sample of the signal or an average amplitude calculated from a set of the electrographic signals as is described more fully below). The implantable medical device 100 further is configured as a neurostimulator so that it can generate and output one or more stimulation waveforms which can be delivered to the patient through a stimulation/sensing element 340 or a stimulation element 344. More particularly, the implantable medical device 100 may be programmed to deliver one or more stimulation waveforms to a location or locations of interest in the patient, and then to recognize one or more features in the electrographic signals that result when each stimulation waveform is applied. The one or more features can be stored by the device (e.g., in the recording module 320), and the implantable medical device 100 may process and analyze the electrographic signals produced as a result of each stimulation waveform with the sensing module 312 and/or the detection module 318. The processing and analysis may accomplish, for example, some form of averaging of the acquired signals, and the results of the processing and analysis may be store in the implantable medical device 100 such as in the event counting/logging module 322.

By way of example and not limitation, the implantable medical device 100 may be configured to generate and output a stimulation waveform characterized by a set of programmable stimulation parameters. As shown in FIG. 10, one such waveform 1000 may comprise just a single pulse 1010 characterized by an amplitude 1012 of, for example 3 mA, a phase width 1014 of 120 μS, and an inter-phase interval 1016 of 100 μS. The implantable medical device 100 may be programmed to generate and output this single-pulse waveform 1000, for example, by instructions implemented by the control module 326, according to a predetermined schedule or otherwise at times triggered by some other criteria (such as when the implantable medical device 100 deems that a "detected event" has occurred). The stimulation waveform 1000 then may be delivered to the patient through one or more designated stimulation elements 344 at a location or locations from which the patient's response to the stimulation waveform 1000 can be sensed by one or more sensing elements 340 (an element through which the stimulation waveform 1000 is delivered can also be configurable for sensing, for an example, an electrode located on the distal portion of a brain lead 114, 116).

The locations for delivering the stimulation waveform 1000 and sensing the electrographic activity the patient's neurons produce in response to the stimulation waveform may be selected based on spatial or temporal considerations, or on where in a given functional neural circuit the stimulation waveform is being applied. For example, the stimulation waveform 1000 may be delivered to one location of interest that comprises a region of neural tissue that is different from the location(s) at which the patient's electrographic response to the stimulation waveform 1000 is being sensed (for example, a region of neural tissue that is distant from the sensing location(s) or which is understood to have neural projections to or otherwise be in communication with the sensing location(s)).

In an embodiment, the implantable medical device 100 may be configured, for example, to acquire an electrographic signal in a 300 ms window following the delivery of a stimulation waveform 1000. This acquired electrographic signal may be deemed an "evoked response" since it is expected to reflect a response of the patient that has been evoked from delivering the stimulation waveform 1000 to the patient.

The implantable medical device 100 further may be configured to process and analyze the acquired electrographic signal(s) constituting each evoked response to identify one or more features in the signal(s), for example, according to a set of detection parameters that govern operation of the detection module 318. For instance, the implantable medical device 100 may be configured to measure an amplitude of each of several samples on an evoked response, such as beginning 100 ms after each stimulation waveform 1000 has been delivered. The implantable medical device 100 further may be configured, for example, using one or more analytical tools implemented in the detection module 318, to calculate an average amplitude of a set of responses evoked using a particular stimulation waveform 1000, for example, to reduce the effect of noise and/or random variation in the actual response.

FIG. 10 illustrates graphically several examples of what might be some evoked responses based on the amplitudes measured in the samples over time for particular evoked responses. For example, four evoked responses 1020, 1022, 1024, 1026 are shown in FIG. 10 relative to a y-axis (or vertical axis) of voltage and an x-axis (or horizontal axis) representing the passage of time. The thick line 1028 on the graph of FIG. 10 represents an average of the four evoked responses 1020, 1022, 1024, 1026. It will be appreciated that analytical tools to create averaged signals may be implemented in the implantable medical device 100, in one or more of the external components, for example the programmer 362 or the data management system 360, or some combination of these.

Evoked responses may be especially relevant to assessing the effectiveness of drug regimens in the case where a drug regimen is being used to treat epilepsy. More particularly, epilepsy is a disease in which neural tissue often is abnormally excitable (i.e., over-excitable). So if the amplitude of an evoked response or average of a given set of evoked responses decreases after a drug is introduced to the patient (or a change to a parameter of a drug regimen is made, such as increasing the dose of an existing drug), then this may suggest to the physician that the tissue from which the evoked response is sensed is less active than it was before the drug was introduced (or other change to a drug regimen was made). Thus, a physician may consider desirable an outcome in which a drug regimen is determined to result in a lower activity level of certain neural tissue may be a desirable outcome.

FIG. 11 is a histogram 1100 where the y-axis corresponds to the average amplitude (in microvolts) of evoked responses (also referred to as "evoked potentials" when the amplitude of the evoked responses is measured in volts) is plotted over time in days on the y-axis, as the dosage of a drug included in a drug regimen to which a patient is subjected is varied from 0 to 2000 mg. The drug may be one intended to treat epilepsy, such as carbamazepine. FIG. 11 may correspond to a display on an external component such as a programmer 362 or a website enabled to access a database of the data management system 360 and the data displayed may be derived from the implantable medical device 100 and/or one or more of the external components 362, 360. In this particular case, the drug the physician selected appears to have no effect at any of the doses on the level of activity of the neural tissue as measured by the averaged evoked responses. In other words, the average evoked potential amplitude remains stable at about 600 μV regardless of whether the dose of the AED (e.g., carbamazepine) is 0 mg (for Days 1-11 (1102)), 500 mg (at Days 12-21 (1104)), 1000 mg (at Days 22-31 (1106)), 1500 mg (at Days 32-41 (1108)) or 2000 mg (at Day 51 et seq. (1110)). Therefore, the physician is likely to conclude from this assessment that the particular drug is not effective in achieving the objective of affecting the behavior, at least in terms of activity level, of the neural tissue associated with the locations where the sensing element(s) 342 have been situated. Consequently, the physician may discontinue the drug (e.g., at about Day 51 (1112) as reflected on FIG. 11).

Figure 12A:
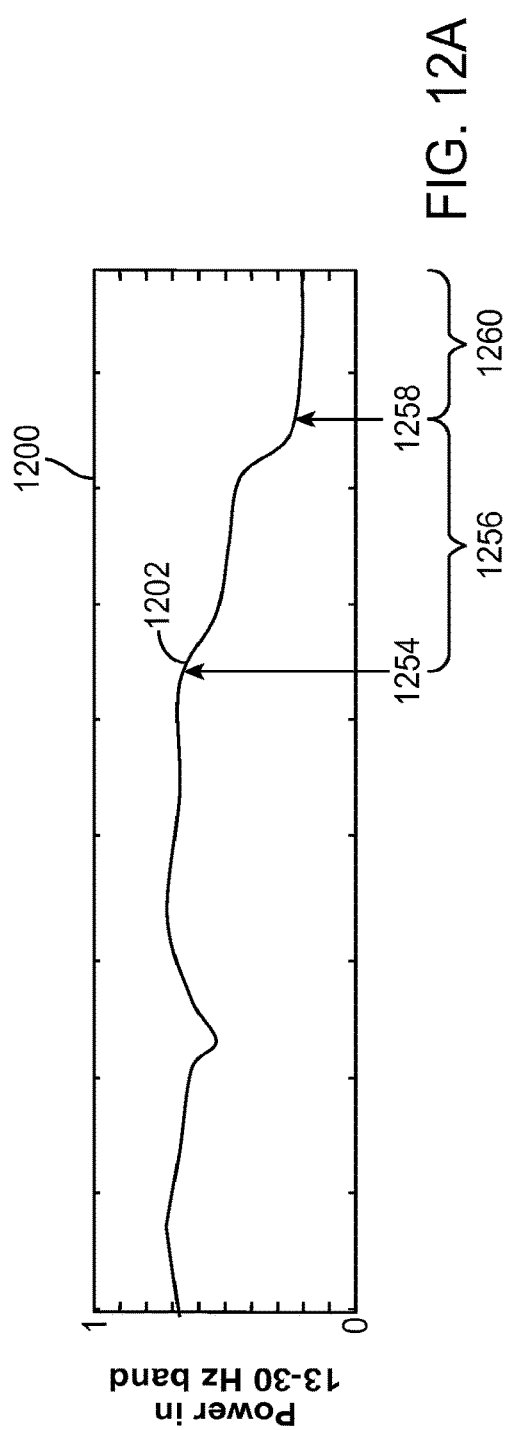
FIG. 12A is a graphical representation of a power value plotted versus time associated with a signal sensed from a patient.
Figure 12B:
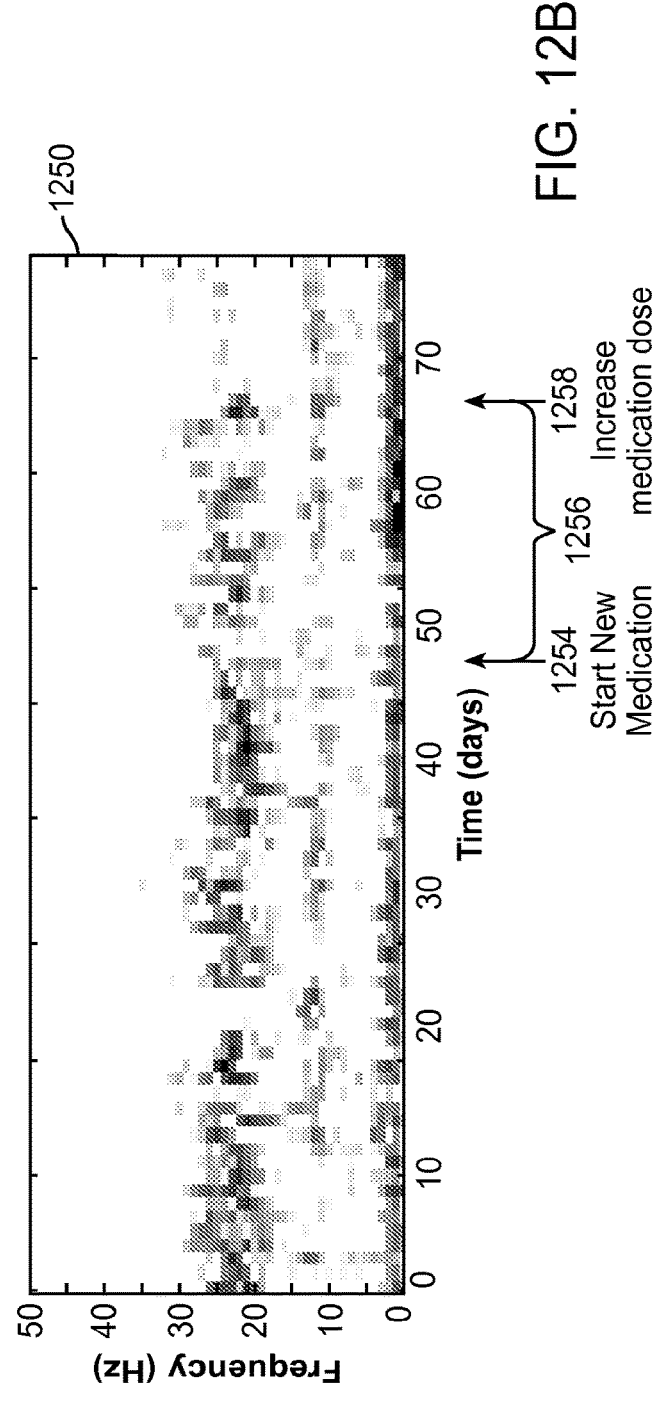
FIG. 12B is a spectrogram corresponding to the plot of FIG. 12A.

Referring now to FIGS. 12A and 12B, embodiments are described wherein the effectiveness of a drug regimen is assessed relative to the concentration in one or more power bands of electrographic signals acquired, processed and analyzed by an implantable medical device 100 and displayed to a user, for example, on a display associated with one or more of the external components, such as a programmer 365 or a website through which a user may interface with a data management system 360.

In these embodiments, an implantable medical device 100 is configured to acquire, process, and analyze electrographic signals sensed from a patient, to identify one or more features in the electrographic signals, such as features that correspond to the power of the signal in particular frequency bands, such as the band from about 13 Hz to about 30 Hz. For example, a detection module 318 of the implantable medical device 100 may be configured with a set of programmable detection parameters to identify when the electrographic signals exhibit frequencies in the 13-30 Hz band using an analytical tool that uses a fast Fourier transform (FFT), filter banks, wavelet transforms, or half-wave spectra. The implantable medical device 100 or one of the external components 362, 360 or the implantable medical device and an external component together may be configured to calculate and generate a display evidencing changes in power of the acquired electrographic signals over time. Techniques such as smoothing by averaging, for example with a cosine window having a duration of one day may be used, for example, to improve the ease with which a user can appreciate the results. (A cosine window is one means for smoothing a rapidly-varying signal, where each measurement is replaced by a weighted average of the nearby measurements. The amount of weighting is determined by a function, such as a cosine function, whose highest value is at 0 (i.e., the central measurement in question is weighted most highly) and whose value decreases in either direction, weighting other values less and less as they become more distant from the central value.)

Each of FIG. 12A and FIG. 12B is an example of a display that might be provided to a user related to an assessment of the effectiveness of a drug using power band information according to embodiments. The line 1202 in the graph 1200 of FIG. 12A represents the variation over time of the power of the electrographic signals acquired by the implantable medical device 100 in a 13-30 Hz power band (y-axis) over a given period of time (x-axis). The spectrogram 1250 of FIG. 12B is an alternative way of displaying the results displayed in FIG. 12A, and illustrates the total power in the 13-30 Hz frequency band of interest where the y-axis corresponds to frequency (in Hz) and the y-axis corresponds to time (in days).

In disorders such as Parkinson's disease, abnormal physiology may be characterized by the occurrence of high-power beta band oscillations in one or more electrographic signals being monitored from the patient's brain. The "beta band" corresponds to frequencies in the range of 13-30 Hz. In other words, the patient may experience one or more unpleasant symptoms of the movement disorder when the electrographic signals exhibit a lot of power in the 13-30 Hz frequency range and it therefore may be desirable to reduce power that occurs in that frequency range in the monitored signals in order to achieve a positive therapeutic result for the patient. According to embodiments, the effectiveness of a drug regimen in reducing the power of the monitored electrographic signals in the beta band may be calculated as the inverse of the power value shown in FIG. 12A.

In a particular example, and with reference to FIGS. 12A and 12B, a physician may start a patient on an anti-Parkinson's medication, such as a drug classified as a dopamine precursor. A marker 1254 at about Day 48 is shown on each of FIGS. 12A and 12B to indicate the day on which the patient starts the new medication and then, after an elapsed time 1256 of about 20 days, the patient begins taking a higher dose of the new medication. The two graphs suggest that the effect of the new medication is to decrease the power of the monitored signal occurring in the frequency band of interest (i.e., the beta band), and that the power in the beta band decreases even further after the patient increase the dose of the new medication. More particularly, and with reference to FIG. 12A, the power in the beta band decreases in the elapsed time 1256 of about 20 days after the patient is started on the new medication, and then decreases further in the elapsed time 1260 at about the Day 68 marker 1258 et seq. Therefore, the physician is likely to conclude from this assessment that the particular drug is somewhat effective in achieving the objective of affecting the behavior, at least in terms decreasing the amount of the signal occurring in the beta band monitored from the neural tissue using the locations where the sensing element(s) 342 have been situated.

Figure 13:
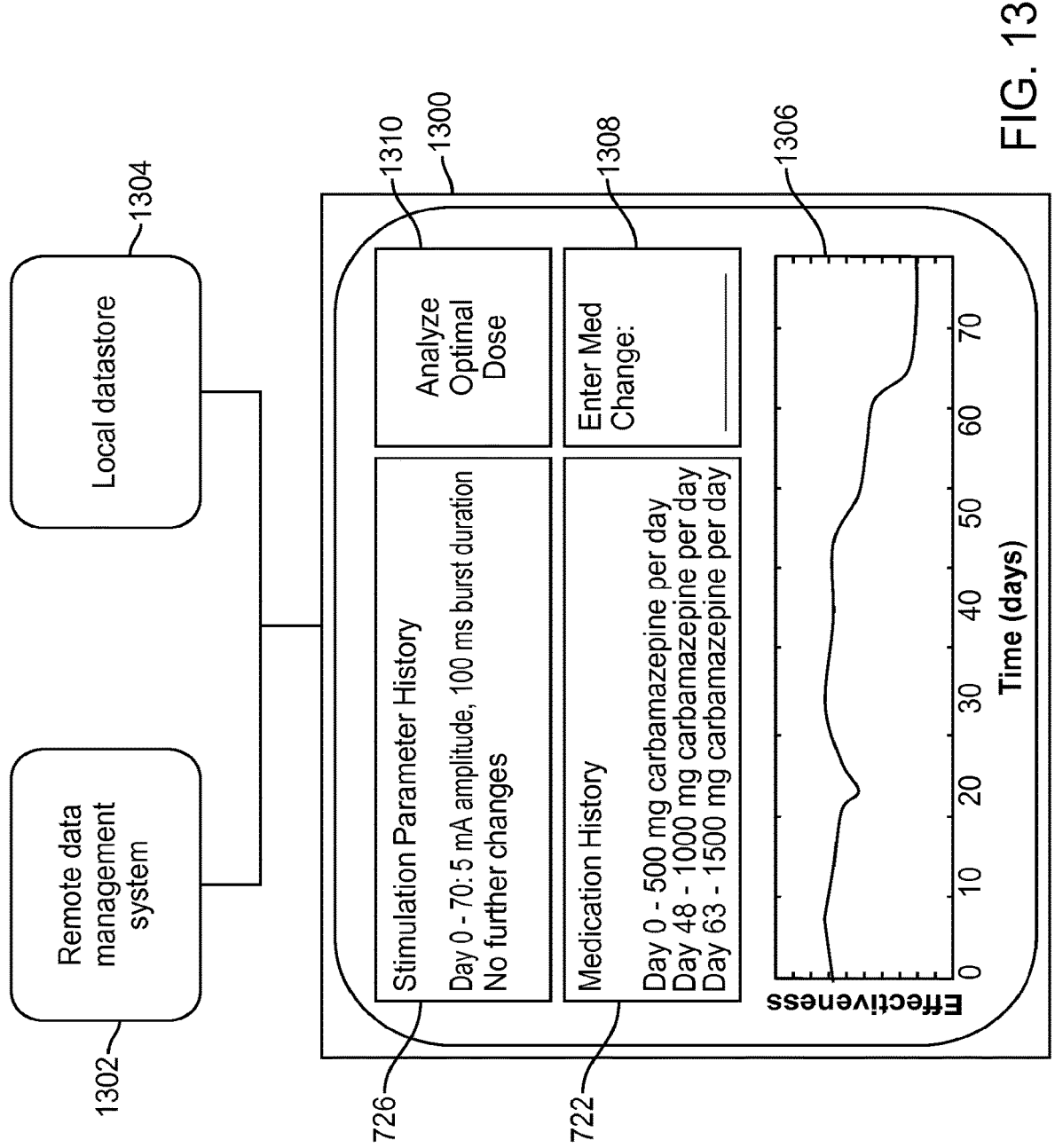
FIG. 13 is a schematic diagram including a display that might be associated with some embodiments.

FIG. 13 illustrates an example of an interactive display and some of the sources from which the data displayed might be drawn according to some embodiments for assessing the effectiveness of a drug regimen. The display 1300 may be viewable by a user on a website in communication with a remote data management system 1302 (such as data management system 360) and/or with a local data store 1304 (such as might be resident on or otherwise associated with a programmer or remote monitor 362).

The particular example shown in FIG. 13 assumes that, in addition to being subjected to a drug regimen, the patient is receiving (or may receive) a form of electrical stimulation (as may be delivered by an implantable medical device 100 configured as a neurostimulator for delivering an electrical stimulation therapy, or perhaps, a stimulation waveform to be used in evoked response analysis).

The display 1300 shows a user a patient's medication history 722 (here, a history of changes to the dose of carbamazepine (from 500 mg to 1500 mg) the patient has been receiving over the past 63 days) and a stimulation parameter history 726 (here, electrical stimulation waveforms 530, 540 characterized by an amplitude 518 of 5 mA and a burst duration 536 of 100 ms for the past 70 days). A graph 1306 provides the user with data showing the variation over a period of days of some value believed to correspond to the effectiveness of the drug regimen over time, including the period covered by the historical medication changes 722 and the stimulation parameter history 726. As discussed elsewhere herein, the value may relate to any measure or metric deemed relevant to drug regimen effectiveness, including "detections per day" (FIG. 8), long episode duration (FIG. 9), average amplitude of evoked responses (FIG. 11) and changes in power of a monitored signal in a particular frequency band (e.g., the beta band) (FIGS. 12A and 12B).

The display 1300 may be an element of an interactive interface (e.g., a graphical user interface or "GUI") of a website associated with the remote data management system 1302 or of an interactive interface with a local data store 1304 with another external component, such as a physician programmer 362. An interactive interface may include an input prompt 1308 prompting the physician to input changes to a drug regimen, such as an increase or decrease in the dose of a drug the physician wants the patient to take. An interactive interface may also include a feature that invites a user to ask for an "optimal dose" analysis, such as by a touch screen button such as the touch screen button 1310 labeled "analyze optimal dose" in FIG. 13. An optimal dose analysis may involve calculations and the execution of algorithms designed to project, for a given drug or combination of drugs, a level of effectiveness based on factors such as: the patient's history with other drug regimens and/or with other forms of therapy intended to modulate neural behavior (e.g., electrical stimulation therapy); the patient's (or a patient caregiver's) reports of the manifestations or symptoms of a disorder (such as reports of seizures in a patient-maintained "seizure diary" or a log of tremors, or disruptions in sleep); other patient-specific factors (such as sex, weight, age, etc.); and, perhaps, factors related to a demographic into which the patient falls (such as patients who experience epilepsy where the seizures are believed to originate from a particular "focus" such as the mesial temporal lobe or a hippocampus).

As mentioned elsewhere herein, it is believed that different forms of therapy delivered in an effort to treat a given patient's particular disorder can interact in synergistic or antagonistic ways. Thus, it would be desirable to exploit the synergies and minimize the antagonisms. An example of a synergy is when the effect of stimulation alone is less than the effect of a combined stimulation and drug therapy. A similar example of a synergy is when the effect of a drug therapy alone is less than the effect of a combined stimulation and drug therapy treatment.

More complex examples of synergies would be when the overall effect of a combination of therapies (such as a combination of a drug therapy and an electrical stimulation therapy) can be adjusted by changing one or more of the parameters of each of the forms of therapy, so that the combination therapy can effectively be "fine tuned" for a given patient to achieve what the physician deems to be an optimal result. For example, patients with epilepsy who are taking medications that block sodium channels may achieve better seizure control if they are provided with stimulation that produces a depolarization block (e.g., depolarizes cells and blocks neuronal firing and therefore neural activity). Stimulation programmed to high frequency (100 Hz or more) and moderate burst durations (100 ms to 1 s) can result in these "depolarization blocks".

In the implantable medical device 100, stimulation parameters such as burst duration 536 or the inter-pulse interval 524 could be adjusted to result in depolarization block. For instance, the inter-pulse interval could be decreased by 1 ms increments resulting in increases in the frequency of stimulation which would increase the likelihood that stimulation would produce a depolarization block. In addition the burst duration could be increased by 100 ms intervals which would also increase the likelihood that stimulation would produce a depolarization block of neuronal firing. In another example, patients taking medications that treat seizures by increasing the neuronal response to inhibitory neurotransmitters such as GABA may achieve the best seizure control when treated with stimulation that drives the activity of neurons to increase the release of neurotransmitters such as GABA. Stimulation programmed to low frequency (1-50 Hz) and long burst durations (1 sec) may drive activity in neurons and increase the release of neurotransmitters.

In the implantable medical device 100 stimulation parameters such as burst duration 536 or the inter-pulse interval 524 could be adjusted to drive neuronal activity and release of neurotransmitters. More specifically the inter-pulse interval could be increased by 1 ms increments to reduce the stimulation frequency and or the burst duration could be increased by 100 ms increments starting at 1 sec. Thus adjusting a stimulation parameter (e.g. increasing or decreasing the inter-pulse interval) may be beneficial to a patient with epilepsy. Furthermore the direction of the stimulation parameter adjustments or ranges, for example the inter-pulse interval adjustment (increase or decrease), that may be beneficial to the patient can be dependent on the type of medication the patient is taking.

Conversely, for a patient that is receiving combined drug and stimulation therapy the type of medication that a physician chooses to add to a patient's drug regimen may be dependent on the stimulation parameters being used to treat the patient's disorder.

In each of these cases where a combination of therapies is delivered, it would be beneficial to provide the physician with useful feedback concerning the effect the adjustment of one parameter of a therapy may have on the overall result of the combination of therapies. Embodiments described herein are intended to provide such useful feedback.

As presaged by the description of FIGS. 5A-5C, an electrical stimulation therapy delivered to a patient can be configured according to a great many parameters and, in many case, each parameter may have a value within a range of possible values. The set of stimulation parameters includes, for example, pulse parameters such as a leading phase 512, a trailing phase 514, and a phase width 516, a pulse amplitude 518, and an overall pulse morphology (e.g., whether the two phases are characterized by the same amplitude and phase width or different amplitudes and phase widths), an inter-phase interval 520, an inter-pulse interval 524, a burst 532, 534 characterizable by a number of pulses in a burst, a burst duration 536, 538, a burst morphology (e.g., whether a burst begins with a "ramp up" period 564 and/or a "ramp down" period 566), whether a burst or set of bursts or pulses is characterized by a duty cycle such that there is a stimulation "on time" 560 and a "stimulation off" time 562, and so on and so forth. Additionally, it will be appreciated that the configuration of the stimulation pathways will also play a role in the patient's response to a given form of electrical stimulation based on where the stimulation elements 344 are located, whether the stimulation elements 344 are in a functional neural circuit or otherwise spatially adjacent to a source of pathological physiological activity, such as seizure focus, etc.

Preliminarily, some of the likely consequences will be described of particular parameter choices for various features of electrical stimulation therapy, such as pulsatile electrical stimulation, and of particular parameter choices for various features of a drug regimen. This description is meant to facilitate later discussion herein of embodiments in which parameters of a combination therapy are adjusted in order to exploit a synergy (such as electrical stimulation improving the effect of a drug) or minimize an antagonism (such as a drug interfering with the effect of stimulation).

A physician may select a drug or set of different drugs with which to treat a patient with a neurological disorder based on a variety of considerations. Generally, medications used to treat diseases of the nervous system have different effects at specific neural locations or circuits and produce different neuronal responses. For example, some medications act on ion channels located on the neuronal membrane and thereby directly alter the threshold for neuronal firing. Some medications block sodium channels and thus inhibit neuronal firing. Physicians often select drugs in this "sodium-channel blocker" class to treat epilepsy, a disease that is characterized by hyperactivity of neurons.

Some other medications block the response to or release of excitatory neurochemicals such as glutamate. Other medications inhibit neuronal activity by increasing the release of or enhancing the response to (such as benzodiazepines) inhibitory neurotransmitters such as GABA and glycine. Still other medications prevent the degradation or reuptake of neurotransmitters (e.g., selective serotonin reuptake inhibitors) prolonging their effect at the synapse.

In an example, a physician may be treating a patient with epilepsy with a drug therapy and with a form of electrical stimulation therapy (such as delivered using an implantable neurostimulator configured from the implantable medical device 100 described elsewhere herein). More specifically, the patient may be taking a medication, such as carbamazepine, that blocks sodium channels in neurons to reduce the activity of the neurons. Such a patient's seizure activity may be further controlled if the electrical stimulation is delivered according to parameters that are expected to result in depolarization block of sodium channels resulting in blocking neuronal firing and therefore discouraging neural activity. Stimulation parameters that may be implicated by this desired therapeutic outcome are the amplitude 518 (of the current or voltage used for the stimulation pulses 510), phase width 516, frequency (or the inverse of the inter-pulse interval 524) and burst duration 536, 538.

In another example, a physician may be treating a patient with epilepsy with a drug therapy and with a form of electrical stimulation therapy where the patient is taking a medication that increases the neuronal response to inhibitory neurotransmitters (such as GABA), resulting in less neural activity. In this case, if there are certain stimulation parameters or stimulation parameter values that are known or suspected to also encourage neurons to release inhibitory neurotransmitters, then the stimulation parameters or parameter values could be selected accordingly to complement the action of the drug and thus drive the neurons to increase release of the inhibitory neurotransmitter of interest.

In still another example, a physician may be treating a patient with epilepsy with a drug therapy and with a form of electrical stimulation therapy where the patient is receiving a form of a stimulation that is correlated with a reduction in the rate of seizures the patient is experiencing, for example, on a daily (or monthly) basis. The parameters of the stimulation, however, may be approaching some not-to-exceed charge limit (e.g., established as a safety precaution) which limit is driven in part by the physical components of the stimulation system (e.g., the surface area of the electrodes through which the stimulation is being delivered). In this circumstance, the physician may choose to increase the dose of a drug the patient is taking that also is expected to tend to reduce the daily (or monthly) seizure rate rather than changing any of the parameters according to which the electrical stimulation is delivered.

Based on the foregoing discussion, it should be appreciated that there are a great many variables at issue whenever an electrical stimulation therapy or a drug therapy, or a combination of the two therapies, are provided to a patient. The situation may be as complicated or even more complicated if therapies other than drug and electrical stimulation are included in a given combination, or if more than one type of drug therapy is provided to a patient (such as some drugs ingested orally by the patient, and others delivered automatically (e.g., by an implanted drug delivery device in response to some local trigger). Moreover, only some of the variables are known; it is not necessarily uncommon for a beneficial effect of a therapy to be appreciated and understood before the precise mechanism by which the effect is achieved is evident. For example, a physician may know that a particular drug leads to a beneficial outcome but the way in which that drug acts at the molecular level or otherwise at a location of interest in the nervous system, may not yet have been discovered.

In light of these great many variables that are implicated in the different possible forms of therapy for a particular disorder of the nervous system, a physician likely always will have to resort to some degree of "trial and error" in fine tuning the parameters of a given therapy to achieve a desired outcome for a particular patient. However, embodiments of the system and method described herein are designed to make the tuning process less burdensome, in part by relying on feedback from an implantable medical device relating to the impact each parameter adjustment has, if any, on the patient. Such feedback may be used to assess the effect of a given parameter change (e.g., adding a new drug or adding a new stimulation waveform or a new stimulation pathway) or of a given change in the value of a parameter (e.g., increasing the dose of a drug in an existing drug regimen or decreasing the total charge delivered to a patient during a burst of electrical stimulation). The feedback can be used to inform decisions (by a physician, by an implantable medical device, or by a physician and device acting in concert) to make further adjustments to one or more therapies a patient is receiving for a particular disorder.

Figure 14:
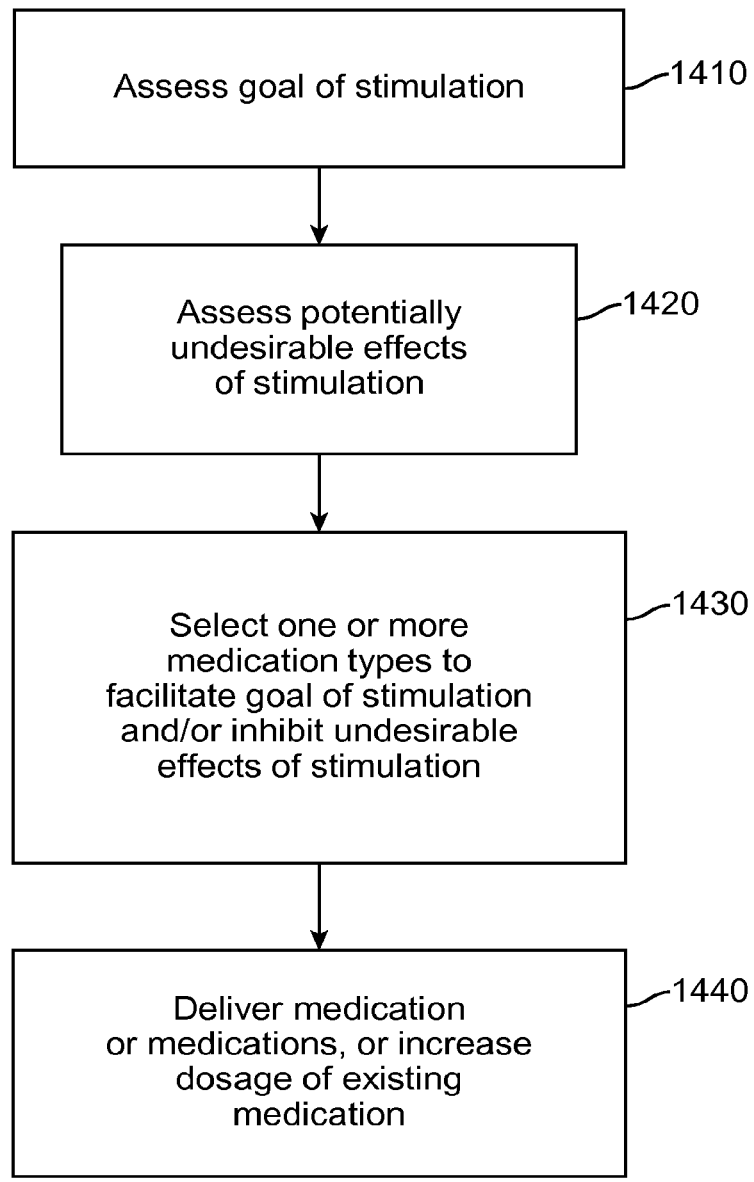
FIG. 14 is another flow chart corresponding to embodiments.

FIG. 14 is a flowchart of a method according to embodiments for selecting one or more medications to increase the effectiveness of an electrical stimulation therapy generated by, for example, an implantable medical device 100 described elsewhere herein configured as a neurostimulator. The stimulation may be delivered to the patient through one or more stimulation pathways configured using the implantable medical device 100 and one or more of the stimulation element 344 and sensing/stimulation element 340.

In some embodiments, a goal or objective of an electrical stimulation therapy is determined (as indicated by the flow chart block 1410); an evaluation is undertaken of the pros and cons of particular electrical stimulation parameters or parameter values for the therapy relative to the goal (as indicated by the flow chart block 1420); a drug regimen is selected in light of the stimulation goal and the evaluation of the stimulation parameters (as indicated by the flow chart block 1430); and the patient begins the drug regimen (as indicated by the flow chart block 1440).

Generally, due to physical or design limitations of a given neurostimulation system, while stimulation can be delivered to one or more stimulation locations, such as stimulation locations at or in the vicinity of a stimulation element 344 or in a functional neural circuit, all the neurons in the vicinity of the stimulation element 344 (or otherwise in the pathway the current follows) will be affected by the stimulation. Put another way, stimulation parameters that increase activity and thereby increase neurotransmitter release can be non-selective. For instance, a physician might decide that a patient with epilepsy would benefit from an increase in the release of the inhibitory neurotransmitter GABA at the seizure focus. Stimulation to increase GABA release at the seizure focus would also increase the release of any excitatory neurotransmitters at the seizure focus which could be detrimental to the patient. Adding felbamate, an antiepileptic medication which acts to both, inhibit excitatory neurotransmitter receptors and enhance the effect of GABA, would reduce or remove the effect of stimulation on excitatory neurotransmission and enhance the effect of the stimulation induced increase in the release of inhibitory neurotransmitters.

In some circumstances, one or more medications may be used in concert with an electrical stimulation therapy in an effort to enhance the effect the electrical stimulation on the neurons one wants to effect and to minimize the effect of the electrical stimulation on the neurons one does not want to affect. Embodiments for achieving these objectives are described below, with reference to the flow chart of FIG. 14 and "determining goals of stimulation" and "assessing undesirable effects of stimulation."

A given goal may be informed by the effect one would expect stimulation according to certain parameters to have at the stimulation location. For example, goals of stimulation might include one of the following: reduce neural activity by producing a depolarization block; inhibit neural activity by increasing activity of inhibitory interneurons at the stimulation location or by activating an inhibitory projection to a different brain region; increase activity by increasing activity at a location of interest or increasing the release of excitatory neurotransmitters produced by that location or increasing activity at a distant region by activating excitatory projections to said region; to increase activity at a location of interest by inducing long-term potentiation (LTP); long lasting enhancement in signal transmission that occurs between neural cells in response to said neurons firing together; decrease activity at the location of interest by inducing long-term depression (LTD); long-lasting reduction in signal transmission that occurs between neurons in response to certain patterns of stimulation (such as repetitive stimulation at one pulse per second for durations of 15 minutes); or improve the availability of physiological resources to the neural tissue by increasing local cerebral blood flow (CBF). The goal may be selected based on an assumption that electrical stimulation characterized by certain parameters is likely to be effective in achieving the goal. The parameters associated with these goals are discussed in more detail below.

In one example, a goal of the electrical stimulation therapy may be determined to decrease neuronal activity by producing a depolarization or conduction block that blocks neuronal firing. If the electrical stimulation consists of pulses delivered at high frequency such as at or above 100 Hz (at or below a 10 ms inter-pulse interval 524), and moderate burst durations such as 100 to 1000 ms and inhibition of neural activity at the location of interest or at a location that receives excitatory projections from or through the location of interest is deemed likely to be beneficial to the patient, then the goal of stimulation may be categorized as "depolarization block". Such inhibition may be judged to be beneficial to the patient if, for instance, symptoms of a neurological disorder are associated with excess excitation of the location of interest or a region that receives excitatory projections from or through that location. An example of stimulation that might be expected to achieve a "depolarization block" goal would be stimulation of the hippocampus in epilepsy using 250 Hz pulses with burst duration 200 ms.

In another example, a goal of stimulation may be to increase activity at a location of interest or increase outflow of a neurotransmitter produced by a location of interest by directly causing firing of action potentials at that location, or to increase activity at a different region other than the location of interest by causing cells to fire that have substantially excitatory projections to said different region. If the electrical stimulation consists of pulses delivered at low frequency such as 1 to 50 Hz and long burst durations such as 1 second or above, and excitation of neural activity at the location of interest or said different region is deemed to be beneficial to the patient, then the goal of stimulation may be categorized as "excitation." Such excitation may be judged to be beneficial to the patient if, for instance, symptoms of a neurological disorder are associated with excess inhibition, inadequate plasticity, or inadequate excitation at the location of interest or said different region. An example of stimulation that might be expected to achieve an "excitation" goal would be stimulation of the ipsilateral motor cortex in stroke using 50 Hz pulses with burst duration 1 sec.

In yet other examples, a goal of stimulation may be to decrease activity at a location of interest by directly causing firing of action potentials in inhibitory neurons, such as interneurons, at the location of interest, or to decrease activity at a different region other than the location of interest by causing cells to fire that have substantially inhibitory projections to said different region. If the electrical stimulation consists of pulses delivered at high frequencies that tend to selectively stimulate interneurons such as 150 to 250 Hz, and moderate burst durations such as 100 to 1000 ms, and inhibition of neural activity at the location of interest is beneficial to the patient, then the goal of stimulation may be categorized as "inhibition." If stimulation consists of pulses delivered at moderate frequencies such as 1 to 50 Hz and long burst durations such as 1 sec or above, and inhibition of neural activity at said different region is deemed to be beneficial to the patient, then the goal of stimulation may be also categorized as "inhibition." Such inhibition may be judged to be beneficial to the patient if, for instance, symptoms of a neurological disorder are associated with excess excitation of the location of interest or a region that receives inhibitory projections from or through that location. Examples of stimulation that might be expected to achieve an "inhibition" goal include stimulation of the external globus pallidus (GPe) in Parkinson's disease using 50 Hz pulses with burst duration 1 sec in order to cause inhibition of the subthalamic nucleus (activating the inhibitory projections from the GPe to the subthalamic nucleus), or stimulation at a seizure focus in epilepsy using 200 Hz pulses with burst duration 200 ms to cause firing of local inhibitory interneurons.

In still another example, a goal of stimulation may be to increase activity or plasticity at a location of interest by inducing LTP. If the electrical stimulation consists of pulses delivered in a manner known to cause LTP, such as pulses at 50 Hz or groups of three pulses at 100 Hz delivered at one group every 200 ms (known as theta burst stimulation), and excitation of neural activity or increased plasticity at the location of interest is deemed to be beneficial to the patient, then the goal of stimulation is categorized as "LTP induction." Such excitation or plasticity may be judged to be beneficial to the patient if, for instance, symptoms of a neurological disorder are associated with excess inhibition, inadequate excitation, or inadequate plasticity at the location of interest. An example of stimulation that may be expected to achieve an "LTP induction" goal includes stimulation of the ipsilateral motor cortex in stroke using theta burst stimulation.

In a further example, a goal of stimulation may be to decrease activity at a target region by inducing LTD. If the electrical stimulation consists of pulses delivered in a manner known to cause LTD, such as pulses at very low frequencies such as long burst durations 536 (15 minutes) at 1 Hz, and inhibition of neural activity at the target region is deemed to be beneficial to the patient, then the goal of stimulation may be categorized as "LTD induction." Such inhibition may be judged to be beneficial to the patient if, for instance, symptoms of a neurological disorder are associated with excess excitation or excess activity at the location of interest. An example of stimulation that may be expected to achieve an "LTP depression" goal includes stimulation of a seizure focus in epilepsy using 1 Hz stimulation.

In a still further example, a goal of stimulation can be to improve availability of physiological resources to the neural tissue by increasing local cerebral blood flow (CBF). If the electrical stimulation consists of pulses delivered in a manner known to increase local CBF, such as pulses at moderate to high frequencies such as 50 to 200 Hz delivered in moderately long bursts such as 100 to 1000 ms, and increased local CBF at the location of interest is deemed to be beneficial to the patient, then the goal of stimulation may be categorized as "CBF increase." Such CBF increase may be judged to be beneficial to the patient if, for instance, symptoms of a neurological disorder are associated with impaired neurovascular coupling or reduced availability of physiological resources such as oxygen or glucose at the location of interest. An example of stimulation that may be expected to achieve a "CBF increase" goal includes stimulation of a seizure focus in epilepsy using 100 Hz stimulation delivered in 200 ms bursts separated by 800 ms or more elapsed time between bursts.

Other goals for stimulation may be determined than are mentioned above, for example, based on research that suggests a certain type of electrical stimulation is likely to have a beneficial effect on neurons involved in a certain way with a certain neurological disorder. For a given combination of therapies (electrical stimulation and drug and/or some other therapy), more than one goal may be determined. Thus, there often may be a need to prioritize goals of a particular combination therapy, so that, for example, only one goal will be selected for facilitating with electrical stimulation and a drug therapy at a time. Further, one or more goals of a combination of therapies may change over time based, for example, on changes in the condition of the patient or new information about the mechanism by which electrical stimulation effects a neural circuit or the mechanism by which a drug functions at the molecular level.

Once a patient's physician has determined a goal, the physician should consider whether attempts to achieve that goal might result in undesirable effects as well as effects consistent with the goal.

For example, a physician may choose a stimulation goal of excitation for the stimulation location. However, the stimulation may activate not only the neurons of interest but also some of the neurons in or near or otherwise functionally associated with the stimulation locations. If such excitation is inconsistent with the goal of the electrical stimulation, then it may be considered an undesirable effect.

For example, a physician may wish to increase the activity of inhibitory interneurons at the stimulation location. However, the stimulation parameters used to increase the activity of the inhibitory cells may also increase the activity of excitatory neurons. Activation of excitatory neurons by electrical stimulation may be considered to be detrimental to the patient if, for instance, the excitation effect causes symptoms of a neurological disorder to worsen or tend to undo a clinical benefit the patient otherwise was experiencing (either from pre-existing electrical stimulation or a drug regimen or some combination of both). An example of a circumstance in which excitation of inhibitory interneurons may be chosen as a goal would be the treatment of epilepsy by electrical stimulation at the seizure focus. However, in this circumstance excitation of excitatory neurons at the seizure focus would be deemed to be undesirable and would result in excitation of the seizure focus and thus a potential seizure. This undesirable effect of stimulation may be mitigated by choosing an appropriate drug therapy allowing the positive effect of stimulation (excitation of inhibitory neurons) and minimizing the undesirable effect (excitation of excitatory neurons).

By way of further example, a physician may select the goal of excitation and may intend to use stimulation to increase excitatory activity when the stimulation waveform is delivered to a location(s) of interest. However, similar to the example above the same stimulation waveform may activate both excitatory neurons at the location of interest and inhibitory neurons in or near or otherwise functionally associated with that location. Thus the net effect of stimulation may be inhibitory instead of excitatory. An example of a circumstance in which an inhibition effect would be deemed to be undesirable would be when electrical stimulation inhibits a patient's motor cortex due to excitation of local inhibitory connections in direct cortical neurostimulation, where the direct cortical stimulation is being delivered to facilitate stroke rehabilitation. Thus using a drug or drugs that enhance the effect of stimulation on excitatory neurons and minimize the effect of stimulation on inhibitory neurons may be beneficial in order to facilitate stimulation therapy for stroke rehabilitation.

Referring again to FIG. 14, and as indicated by the flow chart block 1430, if a patient's treating physician decides after weighing the pros and especially the potential cons associated with a particular goal, that the risk associated with the potential cons can be mitigated, then the physician can select a drug or drugs in an effort to facilitate the particular goal and/or to prevent or inhibit the undesirable effect or effects of stimulation.

For example, a physician may select a medication in the class of drugs known as "ion channel blockers" in an effort to facilitate the effect of an electrical stimulation therapy associated with a "depolarization block" goal in the treatment of epilepsy or migraine.

In another example, a physician may select a medication with multiple mechanisms of action such as felbamate, which acts to both increase the response to inhibitory neurotransmitters and decrease the response to excitatory neurotransmitters in an effort to facilitate the effect of an electrical stimulation therapy which is associated with a goal of "increasing neurotransmitter release" for the treatment of epilepsy.

As mentioned above, this type of stimulation goal may result in the nonspecific increase of both excitatory and inhibitory neurotransmitters. If the intention of treatment is to increase inhibitory neurotransmitter release the stimulation induced increase of excitatory neurotransmitter release may be an undesired effect of stimulation. Since felbamate has multiple mechanisms of action and enhances the effect of the inhibitory neurotransmitter while reducing the response to excitatory neurotransmitters combining felbamate with this type of stimulation therapy would enhance the goal of stimulation and minimize the undesirable effect of stimulation. Thus combining stimulation to increase neurotransmitter release with a drug such as felbamate may produce the desired net inhibitory response for treating seizures at the epileptic focus.

By way of still further example, a physician may select a medication in the class of drugs known as "inhibitory neurotransmitter receptor positive modulators", such as a benzodiazepine, in an effort to facilitate the effect of an electrical stimulation therapy which is associated with a goal of "inhibition" to treat a patient with epilepsy.

In yet another example, a physician may select a medication in the class of drugs known as "serotonin reuptake inhibitors (SSRI)", in an effort to facilitate the effect of an electrical stimulation therapy which is associated with a goal of "excitation" to treat a patient suffering from Major Depressive Disorder ("MDD"). Excitation will increase neural activity which will result in increased neurotransmitter release, including increased serotonin release, which is desirable in treating depression. SSRIs would be expected to enhance the effect of stimulation by decreasing the rate at which serotonin is removed from the synapse.

In some embodiments, one or more of determining a goal of an electrical stimulation therapy (as indicated by the flow chart block 1410); evaluating the potential undesirable effects of particular electrical stimulation parameters or parameter values for the therapy relative to the goal (as indicated by the flow chart block 1420); choosing a drug regimen in light of the stimulation goal and the evaluation of the stimulation parameters (as indicated by the flow chart block 1430); and starting the patient on a drug regimen or adjusting the patient's drug regimen (as indicated by the flow chart block 1440), may be assisted or carried out in part or entirely by one or more of the external components (such as the programmer or patient remote monitor 362 or the data management system 360) and/or based at least in part on data acquired from a patient using an implantable medical device 100 and/or data associated with a condition or conditions of the implantable medical device 100 (e.g., a count of the number of "detections per day" or the instances of saturation of an amplifier of the implantable medical device 100).

Moreover, once a combination of an electrical stimulation therapy and a drug therapy has been decided upon, monitoring the subsequent response of the patient to the combination therapy may be accomplished using the implantable medical device 100 in conjunction with the sensing elements 342, sensing/stimulation elements 340, and stimulation elements 344 (such as the electrode-bearing leads 114, 116) together with one or more of the external components such as the programmer or patient remote monitor 362 and/or the data management system 360.

As a result of such monitoring, the physician or some component of a system automatically may adjust one or more parameters of a drug regimen (e.g., dosage adjusted, medication added, medication removed, etc.) in an effort to improve the patient's overall response or to react to a change in prioritization of one or more of the goals. The automatic adjustment may comprise an output defining the changed drug regimen and thus may require some action by the patient in order to be carried out, such as the patient taking a different pill. Alternatively, the automatic adjustment may comprise commanding an implanted drug delivery device to deliver a new drug or change the dose of a drug already in the patient's drug regimen. (A medication may be prescribed by a physician or and delivered to the patient using delivery methods such as tablets, capsules, injection, or drug-eluting or drug-releasing electrodes or implants.) Similarly, the parameters according to which electrical stimulation therapy is delivered also may be modified or adjusted automatically in whole or in part, for example reprogramming a set of stimulation parameters as commanded via a programmer 362 by a physician.

Figure 15:
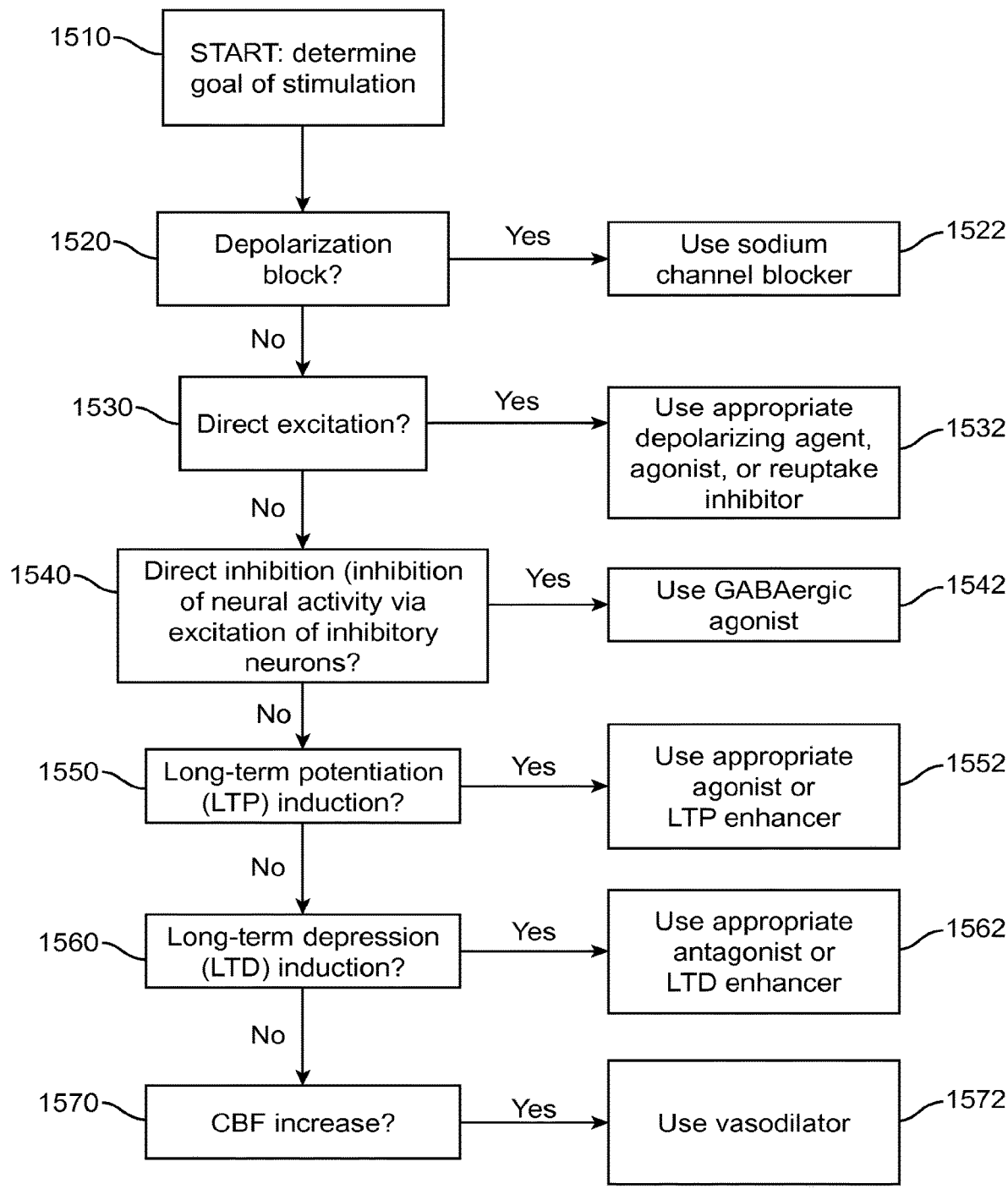
FIG. 15 is a further flow chart corresponding to embodiments.

FIG. 15 is a flowchart of a method according to embodiments for selecting one or more medications to facilitate the desirable effects of an electrical stimulation therapy generated by, for example, an implantable medical device 100 described elsewhere herein configured as a neurostimulator. The stimulation may be delivered to the patient through one or more stimulation pathways configured using the implantable medical device 100 and one or more of the stimulation element 344 and sensing/stimulation element 340.

A goal for an electrical stimulation therapy is determined (as indicated by the flow chart block 1510). Based on the goal, a class of drug is selected.

For example, and as is indicated by the flow chart block 1520, if the goal is "depolarization block", then a sodium channel blocker such as phenytoin or carbamazepine is selected (as is indicated by the flow chart block 1522).

If, and as is indicated by the flow chart block 1530, the goal is "excitation," then a drug in the class of any of a depolarizing agent, an agonist, or a reuptake inhibitor is selected (as indicated by the flow chart block 1532). More specifically, the medication may be one that tends to depolarize neural tissue such as cholecystekinine or a medication such as a serotonin reuptake inhibitor (SSRI) that tends to enhance effects of a neurotransmitter whose release is caused by neurostimulation is selected.

If, and as indicated by the flow chart block 1540, the goal is "inhibition", then a drug in the class of GABAergic agonist is selected (as indicated by the flow chart block 1542). For example, the medication selected may be a benzodiazepine that potentiates an inhibitory neurotransmitter such as GABA.

If, and as indicated by the flow chart block 1550, the goal is "long term potentiation (LTP) induction," then a drug in the class of any of an agonist or LTP enhancer is selected (as indicated by the flow chart block 1552). For example, the medication selected may be one that facilitates LTP by increasing BDNF (brain-derived neurotrophic factor) such as venlafaxine, or acts as a nicotinic acetylcholine receptor agonist such as galantamine is selected.

If, and is indicated by the flow chart block 1560, the goal is "long term depression (LTD) induction", then a drug in the class of any of an antagonist or an LTD enhancer is selected (as indicated by the flow chart block 1562). For example, the medication selected may be a D2 receptor blocker such as clozapine or a medication that inhibits glutamate uptake such as tamoxifen.

Finally, and as indicated in the flow chart block 1570, the goal is "cerebral blood flow (CBF) increase," then a drug in the class of vasodilators is selected (as indicated by the flow chart block 1572). For example, the medication selected may be a medication that causes an increase in CBF such as a diuretic, for example furosemide, or a xanthine derivative such as pentoxifylline.

Figure 16:
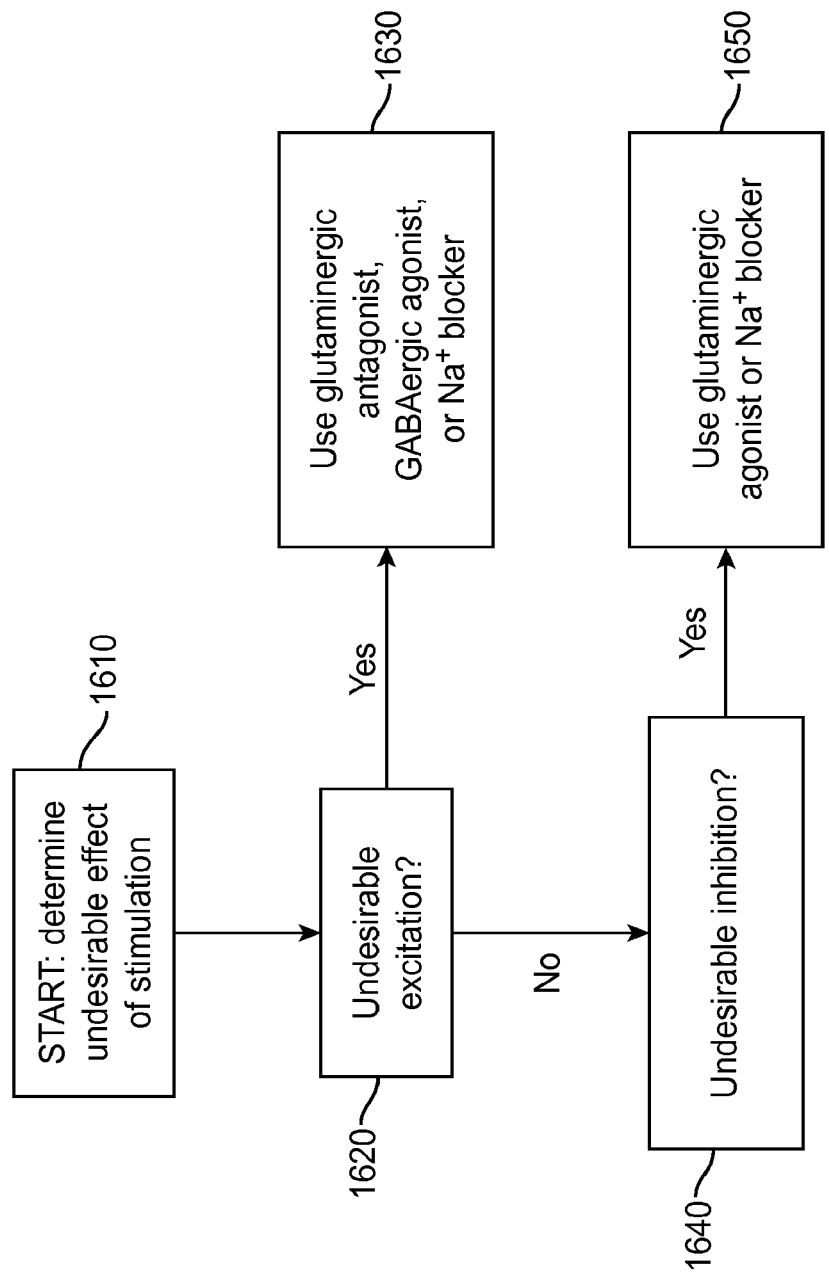
FIG. 16 is a still another flow chart corresponding to embodiments.

FIG. 16 is a flowchart of a method according to embodiments for selecting one or more medications to mitigate the risk that potential undesirable effects of a candidate electrical stimulation therapy will occur when the stimulation therapy is delivered to a patient using, for example, an implantable medical device 100 described elsewhere herein configured as a neurostimulator.

Referring initially to block 1610 of the flow chart of FIG. 16, the potential undesirable effect of a candidate electrical stimulation therapy is determined.

If the potential undesirable effect of the candidate electrical stimulation therapy is "undesirable excitation" as indicated in block 1620, then a drug in the class of any of a glutaminergic antagonist, a GABAergic agonist, and a sodium channel (Na+) blocker is selected (at block 1630). Drugs in these classes tend to reduce neural excitation or neural firing.

If the potential undesirable effect of the candidate electrical stimulation therapy is "undesirable inhibition" as indicated in block 1640, then a drug in the class of any of a glutaminergic agonist, a GABAergic agonist, and a sodium channel (Na+) blocker is selected (at block 1650). Drugs in these classes tend to decrease unwanted fast firing of inhibitory neural tissue.

In other embodiments where a combination of therapies is delivered to a patient and it is desirable to exploit synergies among the therapies and minimize antagonisms, systems and methods are described in which the fine tuning of the combinations of therapies is accomplished at least in part automatically, such as by using an implantable medical device 100, as will be described in more detail below.

More particularly some embodiments of a system and methods rely upon predictable and/or predetermined relationships between a patient's response to a drug regimen and the patient's response to electrical stimulation therapy, as is described below. For example, in the presence of specific medications, a patient's response to neurostimulation may be improved by adjusting specific stimulation parameters in a predictable and predetermined fashion.

More specifically, in the presence of sodium channel blockers such as phenytoin or carbamazepine, a patient's response to stimulation often may be improved by increasing the burst duration 536, 538, such as by 100 ms increments with a start point of 100 ms and not exceeding 1 second. Increasing the burst duration 536, 538 makes it more likely that depolarization and/or conduction blocks will be created, and might be expected to produce a neuronal response similar to and synergistic with that produced by sodium channel blockers (which sodium channel blockers inhibit high frequency repetitive neuronal firing).

Figure 17:
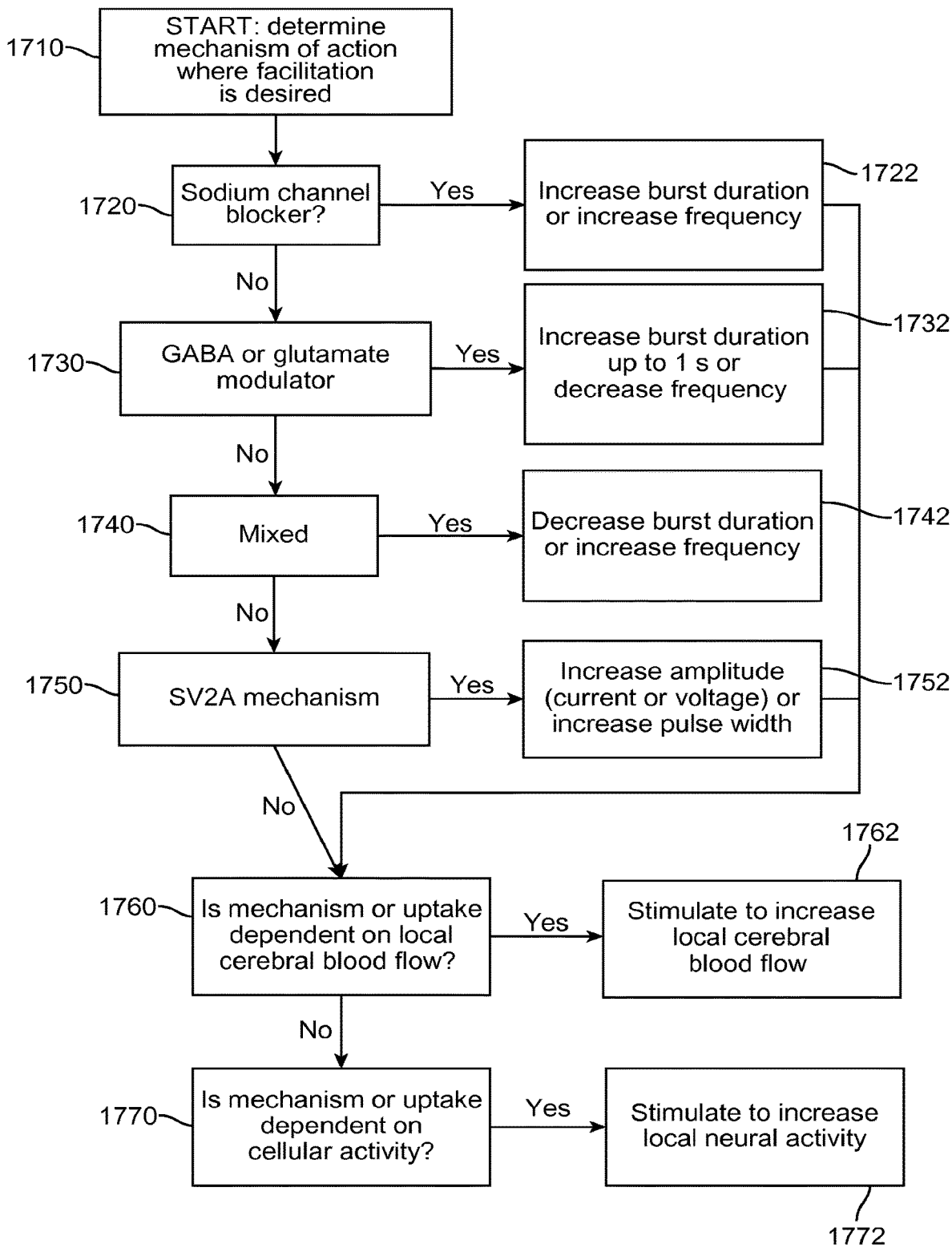
FIG. 17 is yet another flow chart corresponding to embodiments.

FIG. 17 is a flowchart of an embodiment for selecting neurostimulation parameters in treatment of partial onset epilepsy to maximize effectiveness of a combined therapy comprising the neurostimulation therapy and a drug therapy.

At the block 1710 in the flow chart of FIG. 17, a mechanism of action is determined (or assumed or predicted) for a medication that a patient either is already taking or which the physician is considering adding to a patient's drug regimen. By way of example and not by way of limitation, a drug may be characterizable by a primary mechanism of action, multiple mechanisms of action, or an SV2A mechanism of action.

Examples of a drug with a primary mechanism action of a drug include "sodium channel blockers" (the drugs phenytoin or carbamazepine are included in this class of drugs) and "GABA agonists" (barbiturates and benzodiazepines are included in this class of drugs). Drugs associated with multiple mechanisms of action include felbamate which acts as both a glutamate receptor antagonist and a GABA receptor positive modulator. Drugs with a mechanism of action that modulates the activity of synaptic vesicle protein 2A (SV2A) include levetiracetam.

Typically, where a drug is susceptible of more than one mechanism of action, embodiments of the system and method described herein will endeavor to encourage only one such mechanism of action at a time. Some antiepileptic medications in each class are set forth in Table 1.0 below.

| Antiepileptic Medication | Adult Daily Dose |
| --- | --- |
| GABA agonists | — |
| clonazepam | 1.5-20 mg |
| gabapentin | 900-3600 mg |
| phenobarbital | 60-200 mg |
| pregabalin | 150-600 mg |
| tiagabine | 36-56 mg |
| vigabatrin | 1-3 g |
| Sodium channel blockers | — |
| carbamazepine | 600-1400 mg |
| lacosamide | 200-600 mg |
| oxcarbazepine | 600-2400 mg |
| phenytoin | 200-400 mg |
| Multiple mechanisms | — |
| felbamate | 1200-3600 mg |
| lamotrigine | 100-500 mg |
| primidone | 250-1000 mg |
| topiramate | 200-400 mg |
| valproate/valproic acid | 1000-6500 mg |
| zonisamide | 100-600 mg |
| Other | — |
| levetiracetam | 1000-3000 mg |
| ethosuximide | 500-1500 mg |

Whether the medication is a sodium channel blocker is determined at the block 1720 in the flow chart of FIG. 17. If the medication is a sodium channel blocker, then a parameter in the set of stimulation parameters defining a burst duration 536, 538 may be increased (at block 1722). For example, the burst duration may be increase in 100 ms increments until a burst duration 536, 538 of one second is reached, and/or the burst duration parameter may be associated with a not-to-exceed limit of one second. Alternatively or additionally, the frequency of pulses 510 being delivered to the patient in a stimulation waveform may be increased (at block 1722), for example, in 5 Hz increments until a frequency of 250 Hz is reached, and/or the frequency parameter may be associated with a not-to-exceed upper limit of 250 Hz. It will be appreciated that, the patient's response to the incremental changes in the frequency parameters can be monitored by repeatedly measuring physiological data at the stimulation location in the brain as described in more detail above and as described with reference to FIGS. 7-12.

Whether the medication is a GABA or glutamate modulator is determined at the block 1730 in the flow chart of FIG. 17. If the medication is a GABA or glutamate modulator, then a parameter in the set of stimulation parameters defining a burst duration 536, 538 may be increased (at block 1732). For example, the burst duration may be increase in 200 ms increments until a burst duration 536, 538 of one second is reached, and/or the burst duration parameter may be associated with a not-to-exceed limit of one second. Alternatively or additionally, the frequency of pulses 510 being delivered to the patient in a stimulation waveform may be decreased (at block 1732), for example, in 5 Hz increments until a frequency of 1 Hz is reached, and/or the frequency parameter may be associated with a not to exceed lower limit of 1 Hz and to be below a lower limit of 50 Hz.

Whether the medication has a mixed mechanism of action is determined at the block 1740 in the flow chart of FIG. 17. If the medication has a mixed mechanism of action, then a parameter in the set of stimulation parameters defining a burst duration 536, 538 may be decreased (at block 1742). For example, the burst duration may be decreased in 50 ms increments until a lower burst duration 536, 538 threshold of 100 ms is reached, and/or the burst duration parameter may be associated with a not-to-fall-below limit of 100 ms. Alternatively or additionally, the frequency of pulses 510 being delivered to the patient in a stimulation waveform may be decreased (at block 1742), for example, in 5 Hz increments until a frequency of 100 Hz is reached, and/or the frequency parameter may be associated with a not-to-exceed lower limit of 100 Hz.

Whether the medication has the mechanism of action constituting modulating the activity of synaptic vesicle protein 2A (SV2A) is determined at the block 1750 in the flow chart of FIG. 17. If the medication has the "SV2A" mechanism of action, then a parameter in the set of stimulation parameters defining a stimulation amplitude 518 may be increased (at block 1752), such as by increasing a stimulation voltage in 0.1 mA increments. Alternatively or additionally, a phase width parameter (516, 518) may be increased (at block 1752), for example, in 40 μs increments.

After one or more of the stimulation parameters are adjusted according to any of the actions represented by the blocks 1722, 1732, 1742, 1752, further assessment of a medication may be undertaken (at the block 1760) to determine whether any mechanism of action of a drug is dependent on the cerebral blood flow (CBF) in a particular location(s) of interest of the patient's brain (for example, in the pathway defined by one or more stimulation elements 344 or at a sensing element 342). If a mechanism of action of a drug is dependent on CBF, then it may be inferred that the therapeutic efficacy will vary with the cerebral blood flow. For example, it may be inferred that the therapeutic efficacy of a given drug whose mechanism of action depends on local cerebral blood flow will decrease when the local cerebral blood flow decreases.

In circumstances where local cerebral blood flow is presumed to have an effect on the therapeutic efficacy of a drug, then rather than merely adjusting parameters according to which a given stimulation waveform is being delivered, embodiments may introduce a new stimulation waveform to the stimulation therapy. For example, the new stimulation waveform may be the same or different in kind (e.g., may be characterized by the same set of stimulation parameters as an existing stimulation waveform or waveforms, or it may be characterized by a different set of stimulation parameters as an existing waveform or waveforms). Alternatively or additionally, a new stimulation waveform may be generated and output by an implantable medical device 100 and delivered through a different stimulation element 344 or stimulation elements, so that a different location of interest of the brain or different functional circuit of the brain is stimulated. The new stimulation waveforms may be intended to encourage the local cerebral blood flow to increase so as to increase the therapeutic efficacy of a drug in the patient's drug regimen. In a particular example, a new stimulation waveform may be generated and output by an implanted medical device 100 configured as a neurostimulator with a frequency of 100 Hz stimulation delivered in 200 ms bursts separated by 800 ms elapsed time between bursts. Further, the implantable medical device 100 configured as a neurostimulator may be programmed or otherwise instructed to deliver the new stimulation waveform to a stimulation pathway (e.g., formed between one or more stimulation elements 344 or between one or more stimulation elements 344 and the neurostimulator) to treat a location in a patient's brain that is believed to constitute a seizure focus for that patient.

After any further assessments are made to determine information about local cerebral blood flow (i.e., the actions represented by the blocks 1760 and 1762 in FIG. 17) and after one or more of the stimulation parameters are adjusted according to any of the actions represented by the blocks 1722, 1732, 1742, 1752, then a still further assessment of a medication may be undertaken (at the block 1770) to determine whether any mechanism of action of a drug is dependent on local cellular activity (such as a level of neural activity). If a mechanism of action of a drug is dependent on local cellular activity, then it may be inferred that the therapeutic efficacy will vary with variations in the local cellular activity. For example, it may be inferred that the therapeutic efficacy of a given drug whose mechanism of action depends on local cellular activity will decrease when the local cellular activity decreases.

An example of a medication that is understood to have an effect on local cellular activity is 2-deoxy-D-glucose (2-DG).

In circumstances where local cellular activity is presumed to have an effect on the therapeutic efficacy of a drug, then (and as is the case when local cerebral blood flow is presumed to have an effect on the therapeutic efficacy of a drug) rather than merely adjusting parameters according to which a given stimulation waveform is being delivered, embodiments may introduce a new stimulation waveform to the stimulation therapy. The new stimulation waveform may be one of the stimulation waveforms described above in connection with the block 1760 and 1762 of FIG. 17.

In a particular example, a new stimulation waveform may be generated and output by an implanted medical device 100 configured as a neurostimulator with a frequency of 50 Hz stimulation delivered in one second bursts separated by 5000 ms or more elapsed time between bursts. Further, the implantable medical device 100 configured as a neurostimulator will be programmed or otherwise instructed to deliver the new stimulation waveform to a stimulation pathway (e.g., formed between one or more stimulation elements 344 or between one or more stimulation elements 344 and the neurostimulator) to treat a location in a patient's brain that is believed to constitute a seizure focus for that patient.

It should be appreciated that additional or further assessments of a mechanism of action of a drug (including but not limited to mechanisms of action that are affected by local cerebral blood flow or local cellular activity) may be made each time or on predetermined basis or otherwise scheduled after a change to one or more stimulation parameters has been made. Such additional or further assessments may be accomplished to monitor the effect of a change in the short or long term in an effort to maintain a beneficial overall response of the patient to the combination of therapies.

Similarly, assays of the concentrations of a drug in the patient and other physiological data (including neurochemical measurements) may be acquired from the patient from time to time, automatically through use, for example, of the implantable medical device 100, by a physician or laboratory worker in a clinical setting, or some combination of some or all of the implantable medical device 100, an external component such as the programmer or remote monitor 362 or the data management system 360, and the patient's physician. Of course, if the additional or further assessments or assay or other acquired physiological data suggest that a patient is no longer responding beneficially to a particular combination therapy, then appropriate changes to the patient's treatment may be made.

It should further be appreciated that embodiments including the general principles of making adjustments to stimulation parameters and stimulation waveforms while a patient is receiving a drug therapy may be applied in a wide variety of circumstances. For example, combination therapies and the adjustment thereof as described herein may be applied to many different disorders of the nervous system.

Referring now to FIGS. 18-21, described are embodiments of systems and methods in which one or more parameters of a combination therapy including at least a drug therapy and an electrical stimulation therapy may be adjusted in an effort to control the overall result of the combination therapy. The adjusting may be carried out automatically, such as autonomously by an implantable medical device 100 coupled to one or more sensing/stimulation elements 340, sensing elements 342 and stimulation elements 344 in part-time (including in real-time) communication with one or more host devices, including one or more external components such as the programmer or patient remote monitor 362 or the data management system 360. Alternatively or additionally, the adjusting may be carried out at least in part automatically by one or more implanted or external components operating alone or together with input from the patient's treating physician.

The adjusting may be based on variables including, but not limited to any of the following: (1) the parameters defining a drug regimen to which the patient is currently being subjected; (2) the patient's history of drug regimens and changes thereto; (3) the dosage of a drug that is might be toxic to the patient (either when taken alone or in combination with other drugs or in view of certain behaviors of the patient (e.g., smoking, alcohol consumption); (4) an electrical stimulation therapy the patient is currently receiving; (5) the patient's history of electrical stimulation therapies and changes thereto; (6) data concerning drug regimens and electrical stimulation therapy experience for patients falling within the same group or demographic as the patient; (7) physiological data (such as electrographic signals, neurochemical concentrations, oxygenation concentrations, pressure and temperature measurements, accelerometer measurements and so on and so forth); (8) conditions of a device that acquires the physiological data (such as the number of saturations or the length of a saturation of a sensing amplifier in an implantable medical device 100 configured to process and analyzed the physiological data sensed from the patient; the occurrences of predetermined "detected events" an implantable medical device is configured to recognize in the acquired physiological data, or the occurrences of some other identified characteristics the implantable medical device is configured to recognize in the acquired physiological data); and (9) a "goal" of stimulation therapy (as described above with reference to FIG. 14)

The adjusting may be accomplished in a feedback loop in order to maintain an output of a system relative to a target. The target may be a discrete value, a not-to-exceed value (such as a fixed or dynamic threshold), or a range of values.

Figure 18:
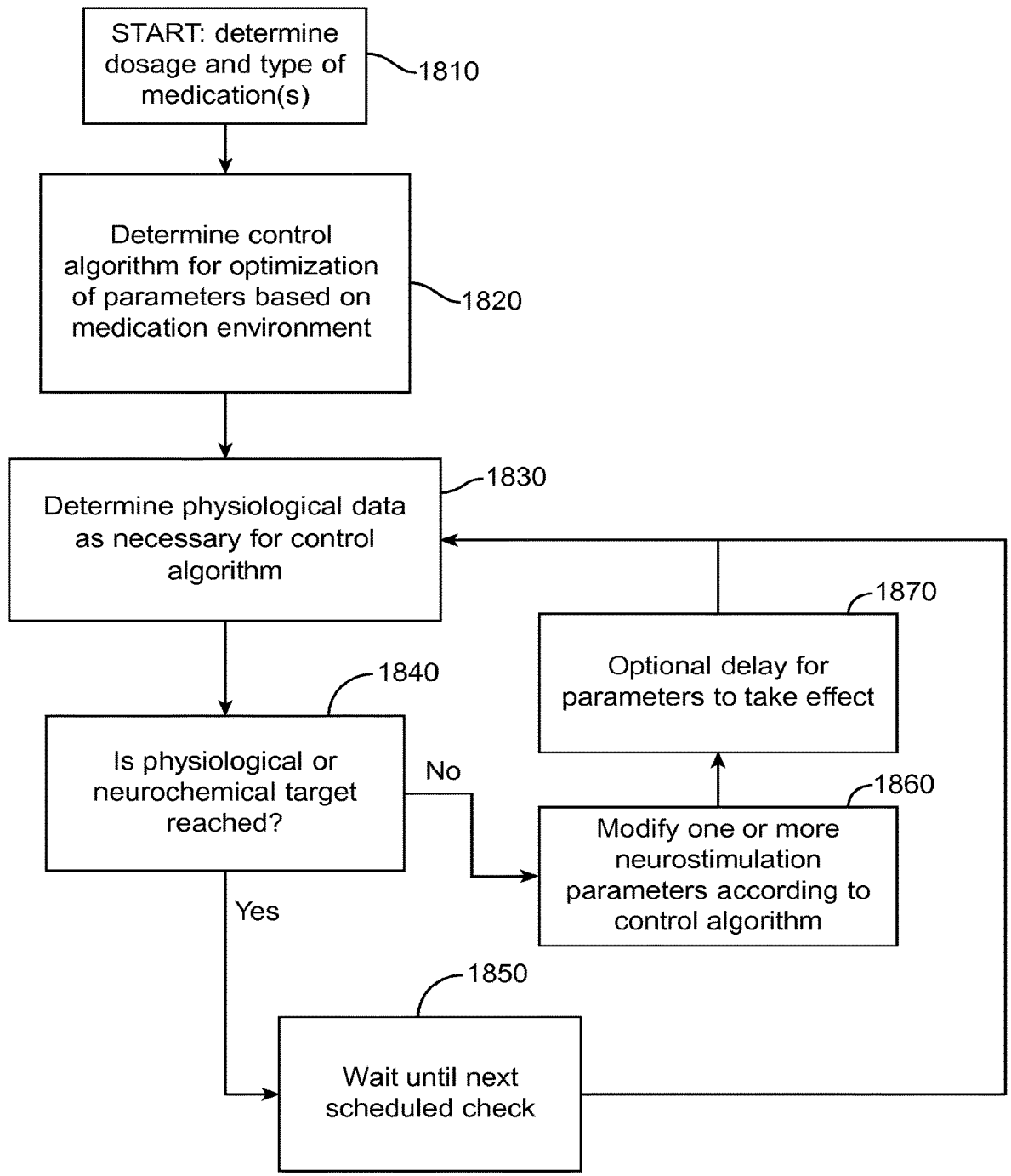
FIG. 18 is a flow chart corresponding to embodiments.

FIG. 18 is a flow chart for embodiments of a system and method for optimizing the parameters according to which electrical stimulation therapy is delivered to a patient in combination with a drug therapy, based on known information about the parameters of a drug regimen to which the patient is being subjected.

Preliminarily, it is assumed that a neurostimulator already has been configured for the patient receiving the drug regimen; preferably, an implantable medical device 100 configured as a neurostimulator according to a set of programmable and variable stimulation parameters. The set of stimulation parameters, for example, may govern the number and composition of the stimulation pathways (e.g., which stimulation electrodes are used) for delivering one or more stimulation waveforms, the timing for delivering of each stimulation waveform (e.g., continuously, periodically on a scheduled basis, or in response to the occurrence of a predetermined trigger), as well as the number and composition of the stimulation waveforms themselves and the timing for delivering of each stimulation waveform.

Typical parameters for stimulation waveforms include the type of waveform (e.g., pulsatile or sine wave or "near-DC"), whether the waveform is characterized by a duty cycle when the stimulation is "on" for a part of the duty cycle and "off" for another part of the duty cycle, the morphology of the waveform (e.g., shape of pulses or shape of bursts), the number of pulses, the pulse parameters (e.g., amplitude, phase width, inter-phase interval, inter-pulse interval (the inverse of which is frequency), the burst parameters (e.g., number of pulses in a burst, whether a burst has "ramp up" period and/or a "ramp down" period), etc.

In some embodiments, the parameters with which an implantable medical device 100 has been configured (e.g., the neurostimulator or another implantable medical device in operable communication with the neurostimulator) may include a set of detection parameters. For example, when the neurostimulator may be configured to deliver stimulation waveforms when certain predetermined features or elements are recognized in the physiological data sensed from one or more sensing elements 342 (i.e., in a "responsive neurostimulation" implementation of a neurostimulation system). The predetermined features or elements may be defined as characteristics to identify in a sensed signal or measurement or "events" to "detect" in the acquired physiological data.

The set of detection parameters or some other parameters that govern operation of the implantable neurostimulation system may cause portions of the acquired physiological data (or digital representations or other approximations thereof) to be recorded by the implantable medical device (e.g., in a recording module 320) and/or by some other component of the neurostimulation system, such as an external component comprising a programmer or patient remote monitor 362 or a data management system 360.

The set of detection parameters or some other parameters that govern operation of the implantable neurostimulation system also may cause data to be stored about one or more conditions of the implantable medical device whenever an identified characteristic or detected event occurs (such as in an event counting/logging module 322 of the implantable medical device 100 or in some other implantable or external component of a neurostimulation system). These device conditions may include but are not limited to data items such as the date and time when an identified condition or detected event occurs and whether the condition or event was associated with a change in the device (e.g., saturation of a sensing amplifier).

Referring now to block 1810 of FIG. 18, a patient's physician or other user provides information relating to the parameters of the current drug regimen of the patient as an input to embodiments of the system or method. The parameters of a drug regimen may include but are not limited to: the number and type of drugs being used (e.g., three drugs total the three drugs being carbamazepine, felbamate, and fluoxetine); the class or mechanism of action of each drug (e.g., sodium channel blocker (one mechanism of action), GABA receptor positive modulator and glutamate receptor antagonist (two mechanisms of action), selective serotonin reuptake inhibitor (SSRI) (one mechanism of action); the dosage of each drug; the timing according to which a total (e.g., daily) dose is achieved; and the method by which each drug is delivered (e.g., orally ingested, injected, delivered using an implanted drug delivery element or system, etc.). The drug regimen or drug regimens to which a patient is subjected may be referred to herein as a "medication environment."

As indicated in block 1820 of FIG. 18, one or more components determine one or more control algorithm to use for deciding whether and, if so, when to adjust parameters in a set of stimulation parameters, based in part on the medication environment. Also at block 1820, one or more components determine a target or targets to associate with the combination therapy.

The control algorithm may be selected from a set of previously defined control algorithms or the control algorithm may be developed according to one or more rules that the system and method may access (e.g., rules that are made available from a central processing unit of the implantable medical device 100, or from some other host, such as host configured as one of the external components (e.g., the programmer or patient remote monitor 362 or the data management system 360), a host configured as a different implantable medical device, or a host configured using a combination of implantable devices or components and external devices or components.

A target may be associated with, for example, one or more desired therapeutic outcomes, with some sort of calibration of the overall system, or with a safety limit or safety margin within which the system is intended to operate. A target may comprise a discrete value, a threshold (e.g., a fixed threshold or a dynamic threshold that varies based on a trend or a predetermined relationship with the value of some other variable in the system), a range of values (e.g., a range of about 50 Hz to about 250 Hz for a parameter corresponding to the frequency with which stimulation pulses 510 are delivered to a patient in a given stimulation waveform). Embodiments may be configured to determine targets based on a look up table or by using one or more algorithms or calculations based on, for instance, system knowledge of the medication environment and existing or historical stimulation parameter values.

After the medication environment is established (at block 1810), and the control algorithm(s) and target(s) are determined (at block 1820), the system and method acquire, process and analyze physiological data and compare the results of the analyses to the relevant target(s) in order to assess whether the target(s) is/are met. The system and method may acquire, process, and analyze the physiological data in any of the ways previously described herein. For example, the physiological data may comprise electrographic signals sensed from desired sensing locations in the patient's brain, and the processing may include filtering the signals to reduce noise and converting the signals from an analog form to a digital form, and the analyzing may include identifying how much of the power of the signal falls within a certain frequency band and when there is a predetermined amount of power in that frequency band, recognizing a "detected event." Alternatively or additionally, the physiological data may comprise a measure of the concentration of a neurochemical in the tissue at or near a sensing element 342.

If the system and method deem a target associated with the analyzed physiological data to have been met (at block 1840), then the system and method may wait a period of time corresponding to a "delay-after-target met" time, as indicated at block 1870 in FIG. 18, before the system and method again acquires, processes and analyzes the physiological data relevant to that target. In some embodiments, the "delay-after-target-met" time may be a variable that is programmable within a predetermined range. For example, the "delay-after-target-met" time may be programmable from one to 5 days. The "delay-after-target-met" time may be selected based on other criteria that affect operation of the system. In some circumstances where the acquiring, processing and analyzing of the physiological data relies on a power source contained within the implantable medical device 100 (e.g., a primary cell or rechargeable battery), how often the physiological data is re-analyzed after a given target has been met may be dictated in part by how much power a measurement consumes or what is the capacity of the power source. In a particular instance, the "delay-after-target-met" time may be three days.

If the system and method deem a target associated with the analyzed physiological data not to have been met (at block 1840), then the system and method may adjust one or more of the parameters according to which the electrical stimulation therapy is delivered. The control algorithm(s) developed at block 1820 may determine which stimulation parameters are adjusted and how they are adjusted. For a given adjustment at block 1860, a single one (e.g., burst duration) or multiple ones (e.g., amplitude and frequency) of the stimulation parameters may be modified.

Following any parameter adjustment at block 1860, the system and method may again, at block 1830, acquire, process, and analyze the physiological data and compare it again to the relevant target to assess whether the adjustment had the desired result (e.g., whether the adjustment does or does not result in targets being met). In some embodiments, following parameter adjustment at block 1860 and before again acquiring, processing and analyzing the physiological data at block 1830, the system will wait for a period of time corresponding to a "delay-after-parameter-adjustment" time, as indicated at block 1870 in FIG. 18. In some embodiments, the "delay-after-parameter-adjustment" time may be a variable that is programmable within a predetermined range. For example, the "delay-after-parameter-adjustment" time may be programmable from one to 24 hours. The "delay-after-parameter-adjustment" time may be selected based on other criteria that affect operation of the system. In some circumstances where the acquiring, processing, and analyzing of the physiological data relies on counting or logging a number of "detections per day", then the "delay-after-parameter-adjustment" time may be set for at least a day so that the effect an adjustment has on the "detections per day" can be appreciated by the system and method. Alternatively or additionally, a "delay-after-parameter-adjustment" time may be selected to allow the patient's nervous system to equilibrate or stabilize or otherwise become acclimated or accustomed to the combination therapy delivered according to the adjusted (e.g., new or modified) stimulation parameters.

In embodiments in which parameter adjustment is accomplished automatically by a host device while the host device is in communication with an implantable neurostimulator, such as a host device comprising or including an external component such as the programmer or patient remote monitor 362 or the data management system 360, the host device accomplishing the adjustment would first retrieve the information acquired, processed, and analyzed by the implantable medical device 100 from the implantable medical device or from a location where the information previously has been stored on an external device (such as in a memory of a programmer or patient remote monitor 362 or a database of the data management system 360), develop the control algorithm(s), test the physiological data information against the target(s), and identify (using the control algorithm(s) and targets) what, if any, adjustments to the stimulation parameters should be made, and then transmit (either immediately or whenever a communication link is next established with the implanted components) any parameter adjustments for the implantable neurostimulator system's use in generating, outputting, and delivering stimulation according to the relevant set of parameters, as adjusted.

In other embodiments, a data management system 360 may retrieve the information acquired, processed and analyzed by the implantable medical device, develop the control algorithm(s), test the physiological data information against the target(s), and identify (using the control algorithm(s) and targets) what, if any, adjustments to the stimulation parameters should be made, and then display (either immediately or whenever called upon to do so) the adjustments in the form of recommendations to a physician treating the patient. The physician can then decide whether to implement the adjustments. If the physician decides to implement the adjustment, the physician may accomplish this by, for example, using a programmer 362 and a part-time communication link with the implantable neurostimulator (e.g., inductive telemetry established using the inductive wand 364). Determining if any stimulation parameter adjustments need to be made can be done by the physician while said data management system is not in immediate communication with the neurostimulator.

Figure 19:
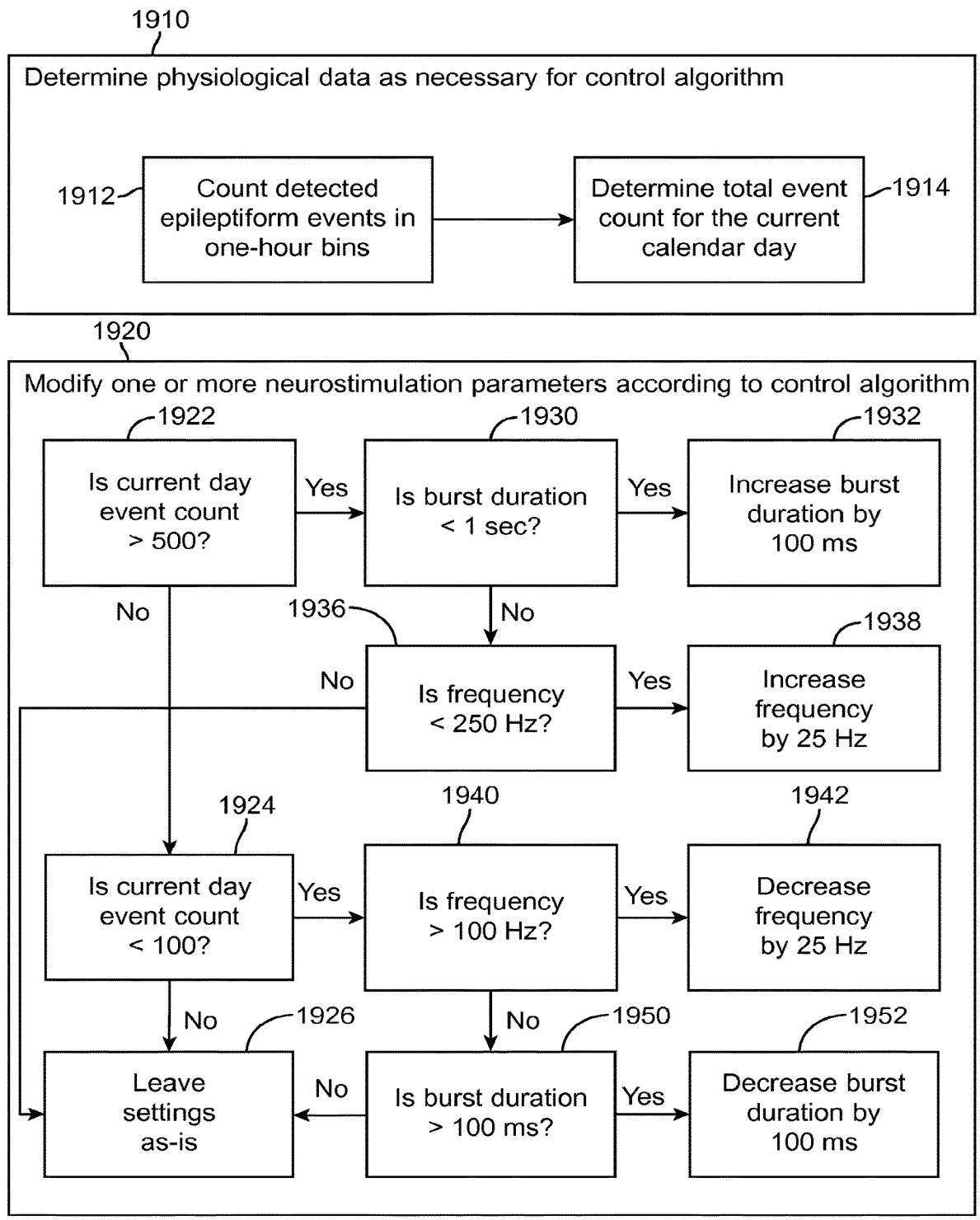
FIG. 19 is another flow chart corresponding to embodiments.

FIG. 19 is a flow chart of systems and methods in which one or more parameters of a combination therapy including at least a drug therapy and an electrical stimulation therapy may be adjusted in an effort to control the overall result of the combination therapy. In this embodiment, the drug therapy is a drug therapy including a medication the mechanism of action of which is as a sodium channel blocker, and the adjusting of the stimulation parameters is accomplished in an effort to optimize the therapeutic result for the patient.

In this embodiment, after the medication environment is established (see, e.g., block 1810 of FIG. 18), and the control algorithm(s) and target(s) are determined (see, e.g., at block 1820 of FIG. 18), the system and method acquire, process, and analyze physiological data and compare the results of the analyses to the relevant target(s) in order to assess whether the target(s) is/are met in block 1910. As indicated in block 1910, acquiring, processing and analyzing physiological data here includes, at block 1912, counting a number of "detected events" that relate to a particular type of epileptiform activity, and organizing the counts into one-hour bins, such that the number of times the detected event occurs in each of several one-hour periods is determined. The acquiring, processing, and analyzing physiological data further includes, at block 1914, determining a total number of "detected events" counted for a calendar day (i.e., the total count of the detected events corresponding to the sum of counts in each of 24 one-hour bins). This value may be designated a "current day event count." In this embodiment, the target associated with the control algorithm may be a target range for the total number of counts of the detected events per day. For example, the target may be to keep the total number of detected events counted per day to 300+/−200 counts per day.

If the system and method deem that the total number of counts of the detected events per day exceeds the target of 300+/−200, then the target will be deemed to not have been met, and, the system and method will determine which stimulation parameter, if any, to adjust at block 1920. The system and method will test how far away from the target is to the "current event day count." More particularly, at block 1922, the "current event day count" will be compared to a count of 500 (i.e., 300 counts+/−200 counts). If the "current event day count" is not greater than 500, then, at block 1924, the "current event day count" will be compared to a count of 100 (i.e., 300 counts+/−200 counts). If the "current event day count" is less than 100, then (at block 1926) the control algorithm may determine that the "current event day count" is below the target of 300 counts+/−200 counts, and that no adjustments need to be made to the set of stimulation parameters.

On the other hand, if at block 1922, the "current event day count" is greater than 500 then, at block 1930, the control algorithm may determine that another stimulation parameter should be checked in order to decide whether any adjustments to the stimulation parameters should be made. For example, at block 1930, the control algorithm tests whether the burst duration that characterizes the present stimulation waveform(s) is less than one second. If the burst duration is not less than one second, then the control algorithm may determine, at block 1932, to upwardly adjust (or to recommend adjustment of, as the case may be) the burst duration by an increment of 100 ms. If the burst duration is not less than one second, then rather than deciding to adjust the burst duration parameter, at block 1936, the control algorithm tests whether the frequency that characterizes the present stimulation waveform(s) is less than 250 Hz.

If the frequency is not less than 250 Hz, then the control algorithm may determine at block 1926 that, even though the "current event day count" is above the target of 300 counts+/−200 counts (i.e., at or above 500 counts), no adjustments should be made to the set of stimulation parameters given the values for the present set of stimulation parameters. On the other hand, if the frequency is less than 250 Hz, then the control algorithm may determine, at block 1938, to upwardly adjust (or to recommend adjustment of, as the case may be) the frequency by an increment of 25 Hz.

If the "current day event count" is less than 500 but equal or greater than 100, as tested by the control algorithm at block 1924, then at block 1940 the control algorithm tests whether the frequency that characterizes the present stimulation waveform(s) is greater than 100 Hz. If the frequency is not greater than 100 Hz, then at block 1950 the control algorithm tests whether the burst duration is greater than 100 ms. If the burst duration is greater than 100 ms, then the control algorithm may determine, at block 1952, to downwardly adjust (or to recommend adjustment of, as the case may be) the burst duration by a decrement of 100 ms. On the other hand, if the frequency is equal to or less than 100 Hz when tested at block 1940, the control algorithm may determine, at block 1942, to downwardly adjust (or to recommend adjustment of) the frequency by a decrement of 25 Hz.

The outcomes of embodiments according to FIG. 19 may correspond to a circumstance in which a low end of a target range can be set for reasons other than clinical effectiveness; there may be no treatment-related reason to adjust settings if fewer than 100 events are counted per day, but it is desirable to reduce stimulation frequency and burst duration when lower values may be acceptable in order to conserve neurostimulator power and extend battery life. In other embodiments, the target range may represent an upper bound, and no parameter adjustments will be made or recommended by the control algorithm for so long as the measured number of counts value falls within or below the target range.

Some or all of the results of execution of the control algorithm described with reference to FIG. 19 may be conveyed to a user via a report viewable on a display, for example, of a host device such as an external component (e.g., the programmer or remote monitor 362 or via a website interface with a data management system 360), and/or printable by a user. A display or report may be configurable to convey more or less information about the execution of the control algorithm (e.g., just the stimulation parameter changes, the date and time of each of the parameter changes, or the results of the analysis that led to each stimulation parameter change or change recommendation), as well as other information, such as information about the medication environment or other stimulation parameter the values of which are not changed (or not recommended to be changed) by the control algorithm.

Figure 20:
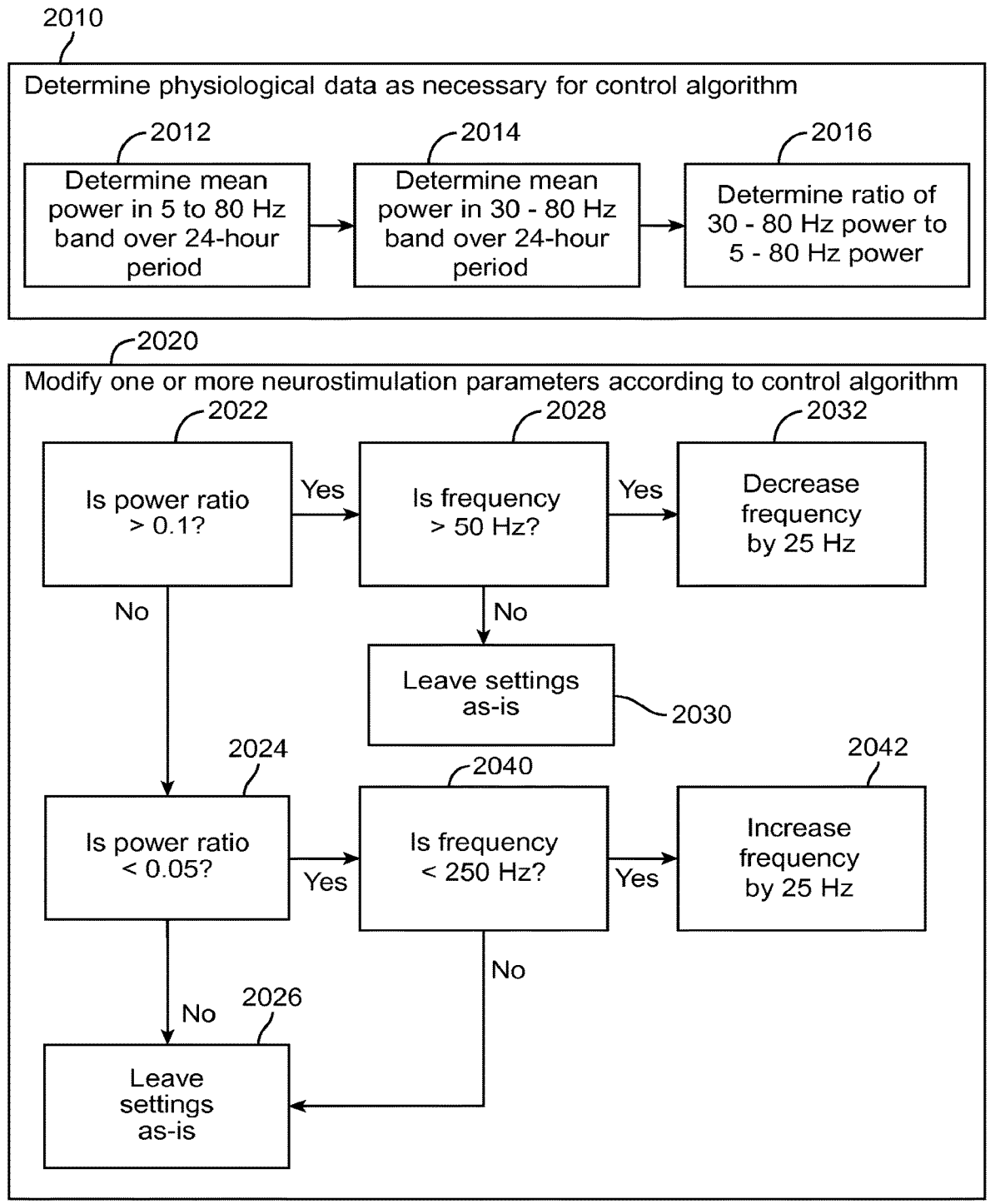
FIG. 20 is further flow chart corresponding to embodiments.

FIG. 20 is a flow chart for embodiments of a system and method for optimizing the parameters according to which electrical stimulation therapy is delivered to a patient in combination with a drug therapy, based on known information about the parameters of a drug regimen to which the patient is being subjected. More specifically, in FIG. 20, the drug regimen includes a medication that modulates the activity of a neurotransmitter such as a GABA receptor agonist.

In this embodiment, after the medication environment is established (see, e.g., block 1810 of FIG. 18), and the control algorithm(s) and target(s) are determined (see, e.g., at block 1820 of FIG. 18), the system and method acquire, process, and analyze physiological data and compare the results of the analyses to the relevant target(s) in order to assess whether the target(s) is/are met in block 2010. As indicated in block 2010, acquiring, processing and analyzing physiological data here includes, at block 2012, determining in an electrographic signal being monitored from the patient a mean power of the signal in a first frequency band, such as the band from about 5 to about 80 Hz, over a period of time such as 24 hours. As indicated in block 2010, acquiring, processing and analyzing physiological data here further includes, at block 2014, determining in an electrographic signal a mean power of the signal in a second frequency band, such as the band from about 30 to about 80 Hz, over the same 24-hour period of time as the power in the first band was measured. The acquiring, processing, and analyzing physiological data still further includes, at block 2016, determining a ratio of the power in the second band relative to the power in the first band. In this embodiment, the target associated with the control algorithm may be a target value of 0.075+/−0.025 for this power ratio. In other words, the target may be a ratio of the second band to the first between 0.1 and 0.05.

If the system and method deem that the power ratio exceeds the target (either by exceeding 0.1 or being less than 0.05), then the target will be deemed to not have been met, and, the system and method will determine whether to and, if so which, stimulation parameter, to adjust at block 2020. The system and method will test how far away from the target is the "power ratio." More particularly, at block 2022, the power ratio will be compared to a power ratio of 0.1. If the power ratio is not greater than 0.1, then, at block 2024, the power ratio will be tested to determine whether it is less than 0.05. If the power ratio is not less than 0.05, then (at block 2026) the control algorithm may determine that the power ratio is within the desired target range for the power ratio and consequently that no adjustments need to be made to the set of stimulation parameters.

On the other hand, if the power ratio is greater than 0.1, then at block 2028, the control algorithm tests whether the frequency that characterizes the present stimulation waveform(s) is greater than 50 Hz. If the frequency is not greater than 50 Hz, then at block 2030, the control algorithm may determine not to adjust any of the stimulation parameters notwithstanding the fact that the power ratio exceeds the upper limit of the target range for the power ratio. On the other hand, if the frequency is greater than 50 Hz, then at block 2032 the control algorithm may determine to downwardly adjust (or to recommend adjustment of, as the case may be) the frequency by an increment of 25 Hz.

If, at block 2024, the control algorithm determines the power ratio to be between 0.1 and 0.05, the control algorithm may then test whether the frequency that characterizes the present stimulation waveform(s) is less than 250 Hz. If the frequency is greater than or equal to 250 Hz, then the control algorithm may determine not to adjust any of the stimulation parameters (at block 2040). On the other hand, if the frequency is less than 250 Hz, the control algorithm may determine to upwardly adjust (or to recommend adjustment of, as the case may be) the frequency by an increment of 25 Hz (at block 2042).

Figure 21:
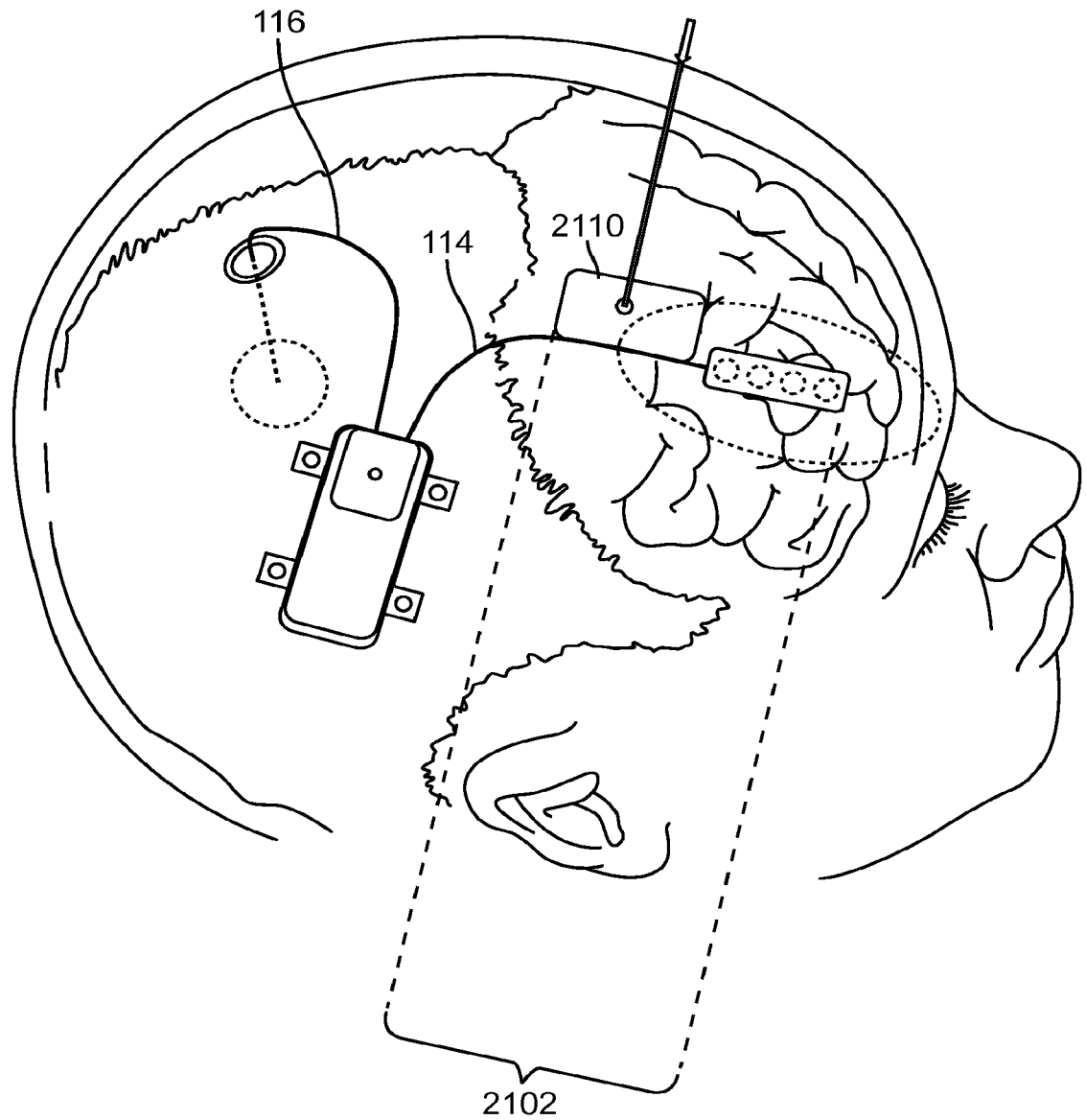
FIG. 21 is a schematic illustration of a patient's head in which a brain lead associated with a drug reservoir and another implantable medical device has been implanted.

FIG. 21 is a schematic illustration of a system for facilitation a combination therapy for a patient which combination therapy includes at least one drug therapy. In an embodiment, one or more leads 114, 116 are implanted in a patient's brain. Each lead 114, 116 may be provided with elements at a distal portion thereof that may be configured either for sensing physiological data from or delivering a form of stimulation (e.g., stimulation intended to modulate neural activity in one or more stimulation pathways through the neural tissue).

In FIG. 21, the lead 114 is a cortical strip lead 116 with a distal portion 2102. A reservoir 2110 is provided in the distal portion 2102. The reservoir 2110 is configured to be in fluid communication with a permeable or semi-permeable membrane that permits a drug in the reservoir to move into the neural tissue (for example, via a lumen in the lead or a wall in the lead or otherwise. It will be apparent that a similar reservoir 2101 may be provided for other types of leads, such as the depth lead 114 or any other lead configurable to be used with neuromodulation system. The reservoir may be filled with medication and, in some embodiments, can be refilled transcutaneously by injecting medication through a needle inserted through the patient's scalp and through a membrane provided on the reservoir. The permeable or semi-permeable membrane may be positioned so that medication diffuses from the reservoir into the neural tissue and so that the region of activity of neurostimulation is at least partially coincident with the region of activity of the delivered medication. U.S. Pat. No. 7,813,811 for "Refillable Reservoir Lead Systems" to Wingeier et al., issued Oct. 12, 2010 is directed to subject matter that includes implantable reservoirs for drugs. U.S. Pat. No. 7,813,811 is incorporated by reference in the entirety herein.

It will be apparent that other means for delivery of neurostimulation and medication therapy may be used beneficially with the embodiments described herein. These other means may include using medication delivery devices, such as drug pumps or drug-eluting devices, including devices combining the functions of drug pump or drug elution and neurostimulation in a single implanted device. U.S. Pat. No. 7,844,345 for "Drug-Eluting Lead Systems" to Boling et al., issued Nov. 30, 2010 is directed to subject matter that includes drug-eluting leads. U.S. Pat. No. 7,844,345 is incorporated by reference in the entirety herein. These other means also may include using systems where medication is delivered via conventional means such as injection or oral administration but is provided in a kit or on a subscription or recurring basis with a neurostimulator. Of course, the means may further include using conventional methods by which medication is delivered such as injection or oral administration.

Some examples of specific combinations therapies including a drug therapy and an electrical stimulation therapy are described below.

Example 1

A patient with mesial temporal lobe epilepsy may be treated with responsive electrical stimulation of the hippocampus, using frequencies such as 100 Hz or greater or phase widths such as 200 μs or greater, while delivering the antiepileptic medication levetiracetam at dosages such as 1000 to 3000 mg administered orally per day. In other embodiments, a drug therapy includes delivering levetiracetam using means such as a drug pump or drug-eluting device to maintain a plasma concentration known to have effectiveness, such as a plasma concentration greater than 11 μg/mL. In alternate embodiments, a drug therapy includes delivering levetiracetam to the patient in order to facilitate a patient's response to responsive neurostimulation at dosages below those known to yield effectiveness in medication-only treatment, such as 100 to 1000 mg administered orally per day, or at dosages that maintain a plasma concentration below that known to yield effectiveness in medication-only treatment, such as plasma concentration from 0.1 to 11 μg/mL. In another embodiment, a drug therapy is delivered to the seizure focus (in this case, the hippocampus) at concentrations that are higher than could be delivered systemically because similarly high concentrations throughout the brain or in the serum would cause unacceptable side effects or even toxicity.

Example 2

A patient with partial onset neocortical epilepsy is treated with responsive electrical stimulation delivered at or near a neocortical focus, using frequencies such as 100 Hz or greater or burst durations such as 200 ms or greater, while delivering a sodium channel blocker such as carbamazepine at dosages such as 800 to 1400 mg administered orally per day. In other embodiments, a drug therapy includes delivering carbamazepine to the patient using means such as a drug pump or drug-eluting device to maintain a plasma concentration known to have effectiveness, such as a plasma concentration greater than 5 µg/mL. In further embodiments, carbamazepine is delivered in order to facilitate a patient's response to responsive neurostimulation at dosages below those known to yield effectiveness in medication-only treatment, such as 100 to 800 mg administered orally per day, or at dosages that maintain a plasma concentration below that known to yield effectiveness in medication-only treatment, such as plasma concentration from 0.1 to 5 µg/mL. In another embodiment, a drug therapy is delivered to the seizure focus (in this case, the temporal neocortex) at concentrations that are higher than could be delivered systemically because similarly high concentrations throughout the brain or in the serum would cause unacceptable side effects or even toxicity.

Example 3

A patient with partial onset epilepsy is treated with responsive electrical stimulation, using frequencies such as 50 to 100 Hz and burst durations such as less than or equal to 500 ms, while delivering a mixed GABA receptor positive modulator and glutamate receptor antagonist such as felbamate at dosages such as 1200 to 3600 mg administered orally per day. In other embodiments, a drug therapy includes delivering felbamate to the patient using means such as a drug pump or drug-eluting device to maintain a plasma concentration known to have effectiveness, such as a plasma concentration greater than 45 µg/mL. In further embodiments, felbamate is delivered in order to facilitate a patient's response to responsive neurostimulation at dosages below those known to yield effectiveness in medication-only treatment, such as 100 to 1200 mg administered orally per day, or at dosages that maintain a plasma concentration below that known to yield effectiveness in medication-only treatment, such as plasma concentration from 0.1 to 45 µg/mL. In another embodiment, felbamate is delivered to the seizure focus at concentrations that are higher than could be delivered systemically because similarly high concentrations throughout the brain or in the serum would cause unacceptable side effects or even toxicity such as the well known life-threatening felbamate-associated toxicity of hepatic necrosis and aplastic anemia.

Example 4

A patient suffering from migraine headaches is treated with electrical stimulation of the trigeminal nerve or occipital nerve using frequencies such as 100 Hz or greater and burst durations such as 200 ms or greater, while delivering a triptan such as sumatriptan when acute symptoms of a migraine headache occur at a dose such as 25 to 100 mg administered orally. In other embodiments, a drug therapy includes delivering sumatriptan to the patient when acute symptoms of migraine headache occur in order to facilitate a patient's response to neurostimulation at dosages below those known to yield effectiveness in medication-only treatment, such as 1 to 25 mg administered orally.

Example 5

A patient with Major Depressive Disorder (MDD) is treated with electrical stimulation of the subgenual cingulate region using frequencies such as 100 Hz or greater and burst durations such as 500 ms or less, while delivering a selective serotonin reuptake inhibitor (SSRI) such as fluoxetine at dosages such as 30 to 60 mg administered orally per day. In other embodiments, a drug therapy includes delivering fluoxetine at dosages such as 30 to 60 mg administered orally to the patient per day. In other embodiments, fluoxetine is delivered to the patient in order to facilitate a patient's response to neurostimulation at dosages below those known to yield effectiveness in medication-only treatment, such as 1 to 30 mg administered orally per day. In another embodiment, the drug therapy is delivered to the subgenual cingulate region at concentrations that are higher than could be delivered systemically because similarly high concentrations throughout the brain or in the serum would cause unacceptable side effects such as sexual dysfunction and mania.

Example 6

A patient with Parkinson's disease is treated with electrical stimulation of the subthalamic nucleus or internal globus pallidus using frequencies such as 130 Hz, while delivering a dopamine agonist such as levodopa at dosages such as 400 to 800 mg administered orally per day. In other embodiments, a drug therapy includes delivering levodopa to the patient in order to facilitate a patient's response to neurostimulation at dosages below those known to yield effectiveness in medication-only treatment, such as 100 to 400 mg administered orally per day. In another embodiment, the drug therapy is delivered to the target at concentrations that are higher than could be delivered systemically because similarly high concentrations throughout the brain or in the serum would cause unacceptable side effects such as psychosis and disinhibition.

Example 7

A patient with Alzheimer's disease is treated with electrical stimulation of the fornix using frequencies such as 100 Hz or greater and burst durations such as 500 ms or less, while delivering a cholinergic agonist such as tacrine at dosages such as 80 to 160 mg administered orally per day. In other embodiments, a drug therapy including tacrine is delivered to the patient in order to facilitate a patient's response to neurostimulation at dosages below those known to yield effectiveness in medication-only treatment, such as 10 to 80 mg administered orally per day. In another embodiment, the drug therapy is delivered to the target at concentrations that are higher than could be delivered systemically because similarly high concentrations throughout the brain or in the serum would cause unacceptable side effects such as changes in vision, diarrhea and agitation.

While the foregoing is directed to certain embodiments, other and further embodiments may be implemented without departing from the scope of the present technology, and the scope thereof is determined by the claims that follow.

What is claimed is:
1. A method comprising:
  acquiring physiological data from a patient via one or more sensors associated with an implanted medical device;
  analyzing with the implanted medical device the acquired physiological data to obtain one or more results;
  determining with the implanted medical device that a drug therapy to which the patient is being subjected is either effective or not effective based on a comparison between at least one of the one or more results and a corresponding baseline or target;

in response to determining that the drug therapy is not effective, delivering with the implanted medical device to one or more locations of interest in the patient's central nervous system a form of neuromodulation therapy according to at least one set of programmable neuromodulation parameters, wherein the form of neuromodulation therapy is different from the drug therapy to which the patient is being subjected; and repeating the acquiring, analyzing, and determining steps with the implanted medical device, and in response to determining that the drug therapy is not effective, adjusting the at least one set of programmable neuromodulation parameters, wherein the form of neuromodulation therapy is electrical stimulation, the at least one set of programmable neuromodulation parameters comprises a set of electrical stimulation parameters, and adjusting the at least one set of programmable neuromodulation parameters comprises adjusting the set of electrical stimulation parameters based on a mechanism of action associated with the drug therapy.

2. The method of claim 1, wherein the adjusting is performed by the implanted medical device.

3. The method of claim 1, further comprising repeating the acquiring, analyzing, determining, delivering, and adjusting steps until the drug therapy is effective or until a predetermined time period has been reached or exceeded.

4. The method of claim 1, wherein the acquired physiological data includes one or more of: electrographic activity sensed from neural tissue, neurochemical levels, neurotransmitter levels, and extracellular levels of oxygen.

5. The method of claim 1, wherein the set of electrical stimulation parameters comprises one or more of a phase width, a pulse amplitude, an overall pulse morphology, an inter-phase interval, a number of pulses in a burst, a burst duration, a burst morphology, a duty cycle, and a stimulation pathway through the one or more locations of interest in the patient's central nervous system.

6. The method of claim 1, wherein the mechanism of action is sodium channel blocker and the adjusting comprises increasing one of a burst duration or a frequency of the set of electrical stimulation parameters.

7. The method of claim 1, wherein the mechanism of action is GABA or glutamate modulator and the adjusting comprises increasing a burst duration or decreasing a frequency of the set of electrical stimulation parameters.

8. The method of claim 1, wherein the mechanism of action is mixed and the adjusting comprises decreasing a burst duration or increasing a frequency of the set of electrical stimulation parameters.

9. The method of claim 1, wherein the mechanism of action is SV2A and the adjusting comprises increasing one of a current amplitude or a voltage amplitude of the set of electrical stimulation parameters, or increasing a pulse width of the set of electrical stimulation parameters.

10. The method of claim 1, wherein the mechanism of action is dependent on cerebral blood flow, and the adjusting the at least one set of programmable neuromodulation parameters comprises adjusting the set of electrical stimulation parameters to increase local cerebral blood flow.

11. The method of claim 1, wherein the mechanism of action is dependent on cellular activity, and the adjusting the at least one set of programmable neuromodulation parameters comprises adjusting the set of electrical stimulation parameters to increase local neural activity.

12. The method of claim 1, wherein the acquired physiological data comprises electrographic activity sensed from neural tissue, the implanted medical device is configured to detect an event in the electrographic activity based on a set of detection parameters, and the one or more results comprises at least one of:

a count of detected events during a time period,
a change in counts of detected events over a plurality of time periods,
a rate of detected events during a time period,
a change in rates of detected events over a plurality of time periods,
a statistical measure of durations of detected events during a time period, and
a change in statistical measures of durations of detected events over a plurality of time periods.

13. The method of claim 1, wherein the acquired physiological data comprises electrographic activity sensed from neural tissue, the implanted medical device is configured to note an occurrence of a device condition caused by the electrographic activity, and the one or more results comprises at least one of:

a count of occurrences of the device condition during a time period,
a change in counts of occurrences of the device condition over a plurality of time periods,
a rate of occurrences of the device condition during a time period,
a change in rates of occurrences of the device condition over a plurality of time periods,
a statistical measure of durations of occurrences of the device condition during a time period, and
a change in statistical measures of durations of occurrences of the device condition over a plurality of time periods.

14. The method of claim 13, wherein the device condition corresponds to a saturation of an amplifier of the implanted medical device.

15. The method of claim 1, wherein the acquired physiological data comprises electrographic activity sensed from neural tissue, the implanted medical device is configured to obtain a measure of power in a frequency band of the electrographic activity, and the one or more results comprises at least one of:

measures of power during a time period, and
a change in measures of power over a plurality of time periods.

16. The method of claim 1, wherein the acquired physiological data comprises electrographic activity sensed from neural tissue, the implanted medical device is configured to obtain a measure of evoked potential amplitude in the electrographic activity, and the one or more results comprises at least one of:

measures of evoked potential amplitude during a time period, and
a change in measures of evoked potential amplitude over a plurality of time periods.

17. The method of claim 1, wherein the acquired physiological data comprises extracellular levels of oxygen, the implanted medical device is configured to compare an extracellular level of oxygen to an oxygen threshold, and the one or more results comprises at least one of:

a count of occurrences of the extracellular level of oxygen being below the oxygen threshold during a time period,
a change in counts of the occurrences over a plurality of time periods,
a rate of counts of the occurrences during a time period, and a change in rates of counts of the occurrences over a plurality of time periods.

18. The method of claim 1, wherein the acquired physiological data comprises neurochemical levels, the implanted medical device is configured to compare a neurochemical level to a neurochemical threshold, and the one or more results comprises at least one of:
a count of occurrences of the neurochemical level being below the neurochemical threshold during a time period,
a change in counts of the occurrences over a plurality of time periods,
a rate of counts of the occurrences during a time period, and
a change in rates of counts of the occurrences over a plurality of time periods.

19. The method of claim 1, wherein the acquired physiological data comprises neurotransmitter levels, the implanted medical device is configured to compare a neurotransmitter level to a neurotransmitter threshold, and the one or more results comprises at least one of:
a count of occurrences of the neurotransmitter level being above the neurotransmitter threshold during a time period,
a change in counts of the occurrences over a plurality of time periods,
a rate of counts of the occurrences during a time period, and
a change in rates of counts of the occurrences over a plurality of time periods.

20. An implantable medical device comprising:
one or more sensors configured to acquire physiological data from a patient;
a neurostimulator configured to deliver a form of neuromodulation therapy to the patient through one or more stimulation elements; and
a processor coupled to the one or more sensors and the neurostimulator and configured to:
analyze the acquired physiological data to obtain one or more results;
determine that a drug therapy to which the patient is being subjected is either effective or not effective based on a comparison between at least one of the one or more results and a corresponding baseline or target;
in response to determining that the drug therapy is not effective, deliver through the neurostimulator to one or more locations of interest in the patient's central nervous system, the form of neuromodulation therapy according to at least one set of programmable neuromodulation parameters; and
repeat the acquiring, analyzing, and determining, and in response to determining that the drug therapy is not effective, adjust the at least one set of programmable neuromodulation parameters,
wherein the form of neuromodulation therapy is electrical stimulation, the at least one set of programmable neuromodulation parameters comprises a set of electrical stimulation parameters, and the processor is configured to adjust the at least one set of programmable neuromodulation parameters by adjusting the set of electrical stimulation parameters based on a mechanism of action associated with the drug therapy.

21. The device of claim 20, wherein the processor is further configured to repeat the acquiring, analyzing, determining, delivering, and adjusting until the drug therapy is effective or until a predetermined time period has been reached or exceeded.

22. The device of claim 20, wherein the set of electrical stimulation parameters comprises one or more of a phase width, a pulse amplitude, an overall pulse morphology, an inter-phase interval, a number of pulses in a burst, a burst duration, a burst morphology, a duty cycle, and a stimulation pathway through the one or more locations of interest in the patient's central nervous system.

23. The device of claim 20, wherein the acquired physiological data comprises electrographic activity sensed from neural tissue, the processor is configured to detect an event in the electrographic activity based on a set of detection parameters, and the one or more results comprises at least one of:
a count of detected events during a time period,
a change in counts of detected events over a plurality of time periods,
a rate of detected events during a time period,
a change in rates of detected events over a plurality of time periods,
a statistical measure of durations of detected events during a time period, and
a change in statistical measures of durations of detected events over a plurality of time periods.

24. The device of claim 20, wherein the acquired physiological data comprises electrographic activity sensed from neural tissue, the processor is configured to note an occurrence of a device condition caused by the electrographic activity, and the one or more results comprises at least one of:
a count of occurrences of the device condition during a time period,
a change in counts of occurrences of the device condition over a plurality of time periods,
a rate of occurrences of the device condition during a time period,
a change in rates of occurrences of the device condition over a plurality of time periods,
a statistical measure of durations of occurrences of the device condition during a time period, and
a change in statistical measures of durations of occurrences of the device condition over a plurality of time periods.

25. The device of claim 20, wherein the acquired physiological data comprises electrographic activity sensed from neural tissue, the processor is configured to obtain a measure of power in a frequency band of the electrographic activity, and the one or more results comprises at least one of:
measures of power during a time period, and
a change in measures of power over a plurality of time periods.

26. The device of claim 20, wherein the acquired physiological data comprises electrographic activity sensed from neural tissue, the processor is configured to obtain a measure of evoked potential amplitude in the electrographic activity, and the one or more results comprises at least one of:
measures of evoked potential amplitude during a time period, and
a change in measures of evoked potential amplitude over a plurality of time periods.

27. The device of claim 20, wherein the acquired physiological data comprises extracellular levels of oxygen, the processor is configured to compare an extracellular level of oxygen to an oxygen threshold, and the one or more results comprises at least one of:

a count of occurrences of the extracellular level of oxygen being below the oxygen threshold during a time period, a change in counts of the occurrences over a plurality of time periods, a rate of counts of the occurrences during a time period, and a change in rates of counts of the occurrences over a plurality of time periods.

28. The device of claim 20, wherein the acquired physiological data comprises neurochemical levels, the processor is configured to compare a neurochemical level to a neurochemical threshold, and the one or more results comprises at least one of:

a count of occurrences of the neurochemical level being below the neurochemical threshold during a time period, a change in counts of the occurrences over a plurality of time periods, a rate of counts of the occurrences during a time period, and a change in rates of counts of the occurrences over a plurality of time periods.

29. The device of claim 20, wherein the acquired physiological data comprises neurotransmitter levels, the processor is configured to compare a neurotransmitter level to a neurotransmitter threshold, and the one or more results comprises at least one of:

a count of occurrences of the neurotransmitter level being above the neurotransmitter threshold during a time period, a change in counts of the occurrences over a plurality of time periods, a rate of counts of the occurrences during a time period, and a change in rates of counts of the occurrences over a plurality of time periods.

* * * * *